(12) United States Patent
Kawashima et al.

(10) Patent No.: US 10,435,379 B2
(45) Date of Patent: *Oct. 8, 2019

(54) [4-(1,3,3-TRIMETHYL-2-OXO-3,4-DIHYDRO-1H-QUINOXALIN-7-YL)PHENOXY]ETHYLOXY COMPOUND OR SALT THEREOF

(71) Applicant: SANTEN PHARMACEUTICAL CO., LTD., Osaka-shi, Osaka (JP)

(72) Inventors: Kenji Kawashima, Osaka (JP); Yusuke Yamazaki, Ikoma (JP); Shinji Takaoka, Ikoma (JP); Daisuke Shii, Osaka (JP); Tomoko Oda, Ikoma (JP); Takahiro Matsuyama, Ikoma (JP)

(73) Assignee: SANTEN PHARMACEUTICAL CO., LTD., Osaka-Shi, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/210,163

(22) Filed: Dec. 5, 2018

(65) Prior Publication Data

US 2019/0106393 A1  Apr. 11, 2019

Related U.S. Application Data

(63) Continuation of application No. 15/753,410, filed as application No. PCT/JP2016/074863 on Aug. 25, 2016, now Pat. No. 10,189,796.

(30) Foreign Application Priority Data

Aug. 25, 2015 (JP) .................................. 2015-166247

(51) Int. Cl.
| | |
|---|---|
| *C07D 241/44* | (2006.01) |
| *C07D 403/12* | (2006.01) |
| *A61K 31/498* | (2006.01) |
| *A61K 31/5377* | (2006.01) |
| *A61K 31/675* | (2006.01) |
| *A61P 27/02* | (2006.01) |
| *A61P 29/00* | (2006.01) |
| *C07F 9/6509* | (2006.01) |

(52) U.S. Cl.
CPC .......... *C07D 241/44* (2013.01); *A61K 31/498* (2013.01); *A61K 31/5377* (2013.01); *A61K 31/675* (2013.01); *A61P 27/02* (2018.01); *A61P 29/00* (2018.01); *C07D 403/12* (2013.01); *C07F 9/650994* (2013.01)

(58) Field of Classification Search
CPC .................................................... C07D 241/44
See application file for complete search history.

(56) References Cited

U.S. PATENT DOCUMENTS

| | | |
|---|---|---|
| 2004/0014741 A1 | 1/2004 | Liu et al. |
| 2009/0111807 A1 | 4/2009 | Matsuda et al. |
| 2010/0137307 A1 | 6/2010 | Matsuda et al. |
| 2011/0118260 A1 | 5/2011 | Kato et al. |
| 2011/0166151 A1 | 7/2011 | Kato et al. |
| 2018/0244633 A1* | 8/2018 | Kawashima ......... C07D 403/12 |

FOREIGN PATENT DOCUMENTS

| | | |
|---|---|---|
| JP | 2002-193955 A | 7/2002 |
| JP | 2008-074829 A | 4/2008 |
| JP | 2009-084273 A | 4/2009 |
| JP | 2009-084274 A | 4/2009 |
| JP | 2009-298775 A | 12/2009 |

OTHER PUBLICATIONS

International Search Report (PCT/ISA/210) dated Sep. 27, 2016, by the Japanese Patent Office as the International Searching Authority for International Application No. PCT/JP2016/074863.
Written Opinion (PCT/ISA/237) dated Sep. 27, 2016, by the Japanese Patent Office as the International Searching Authority for International Application No. PCT/JP2016/074863.

* cited by examiner

*Primary Examiner* — Joseph R Kosack
(74) *Attorney, Agent, or Firm* — Buchanan, Ingersoll & Rooney PC

(57) ABSTRACT

The present invention relates to defined quinoxalin-2-one compounds or a pharmaceutically acceptable salt or a hydrate or a solvate thereof. The compounds, salts or hydrates have a glucocorticoid receptor agonist activity, and are useful as a medicine, in particular as a prophylactic or therapeutic agent for a glucocorticoid receptor related disease.

9 Claims, No Drawings

[4-(1,3,3-TRIMETHYL-2-OXO-3,4-DIHYDRO-1H-QUINOXALIN-7-YL)PHENOXY] ETHYLOXY COMPOUND OR SALT THEREOF

CROSS-REFERENCE TO RELATED APPLICATIONS

This application is a continuation of U.S. application Ser. No. 15/753,410, filed Feb. 19, 2018, which is a U.S. National Stage Application of PCT/JP2016/074863, filed Aug. 25, 2016, which claims priority to Japanese Patent Application No. 2015-166247, filed Aug. 25, 2015, the contents of all of which are hereby incorporated by reference.

TECHNICAL FIELD

The present invention relates to a novel [4-(1,3,3-trimethyl-2-oxo-3,4-dihydro-1H-quinoxalin-7-yl)phenoxy]ethyloxy compound or a salt thereof. The compound of the present invention or a salt thereof has a glucocorticoid receptor agonist activity, and useful as a medicament, in particular, as a prophylactic or therapeutic agent for a glucocorticoid receptor related disease.

BACKGROUND ART

A glucocorticoid receptor is a 94 kDa ligand-activated intracellular transcriptional factor that is a member of the nuclear receptor superfamily. This receptor is known to regulate the metabolism of carbohydrates, proteins, fats and the like, suppress the immune or inflammatory responses, activate the central nervous system, regulate cardiovascular function, and affect basal and stress-related homeostasis and the like due to its transcriptional regulatory action (Non-Patent Document 1, Patent Document 1).

Therefore, a compound having a glucocorticoid receptor binding activity, in particular, a compound having an agonist action to the glucocorticoid receptor (hereinafter also referred to as "the glucocorticoid receptor agonist") is considered to be useful as a prophylactic and/or therapeutic agent for these diseases.

Patent Document 2 discloses 1,2,3,4-tetrahydroquinoxalinone derivatives which are glucocorticoid receptor modulators.

Patent Document 3 discloses 1,3,3-trimethyl-7-phenyl-3,4-dihydro-1H-quinoxalin-2-one derivatives which are glucocorticoid receptor agonists.

However, the [4-(1,3,3-trimethyl-2-oxo-3,4-dihydro-1H-quinoxalin-7-yl)phenoxy]ethyloxy compound or a salt thereof is not specifically disclosed in any of the documents.

PRIOR ART DOCUMENT

Patent Document

Patent Document 1: JP 2002-193955A
Patent Document 2: JP 2008-74829A
Patent Document 3: JP 2009-84273A

Non-Patent Document

Non-Patent Document 1: Clinic All-Round, 54 (7), 1951-2076 (2005)

SUMMARY OF THE INVENTION

Problems to be Solved by the Invention

It is a very interesting subject to provide a novel [4-(1,3,3-trimethyl-2-oxo-3,4-dihydro-1H-quinoxalin-7-yl)phenoxy]ethyloxy compound or a salt thereof.

Means to Solve the Problems

The present inventors conducted studies of synthesis of [4-(1,3,3-trimethyl-2-oxo-3,4-dihydro-1H-quinoxalin-7-yl)phenoxy]ethyloxy compound or a salt thereof, and succeeded in producing a large number of novel compounds. Further, the present inventors studied the pharmacological actions of the compounds, and as a result, they found that the [4-(1,3,3-trimethyl-2-oxo-3,4-dihydro-1H-quinoxalin-7-yl)phenoxy]-ethyloxy compound or a salt thereof has a glucocorticoid receptor agonist activity and are useful as a medicament, and thus the present invention has been completed.

The present invention relates to a compound represented by the following general formula (1) or a salt thereof (hereinafter referred to as "the present compound") and a pharmaceutical composition comprising the same. Further, a preferred invention in its pharmaceutical use relates to a glucocorticoid receptor agonist, and its target diseases are glucocorticoid receptor related diseases, that is, endocrine diseases, collagen diseases, kidney diseases, heart diseases, allergic diseases, blood diseases, digestive system diseases, liver diseases, pulmonary diseases, severe infectious diseases, tuberculosis disease, nervous disease, malignant tumor, digestive organ symptoms accompanied by administration of an anti-malignant tumor agent, surgery related diseases, obstetrics and gynecology related diseases, urology related diseases, skin diseases, otolaryngology related diseases, oral surgery related diseases, glaucoma, rheumatic diseases, inflammatory diseases and the like. A particularly preferred invention is an invention relating to a prophylactic or a therapeutic agent for these diseases. In addition, the present invention also relates to use of the present compound for the prophylaxis or treatment of these diseases, use of the present compound for the manufacture of a medicament for the prophylaxis or treatment of these diseases, and a method for the prophylaxis or treatment of these diseases, which comprises administering an effective amount of the present compound.

(1)

[Formula 1]

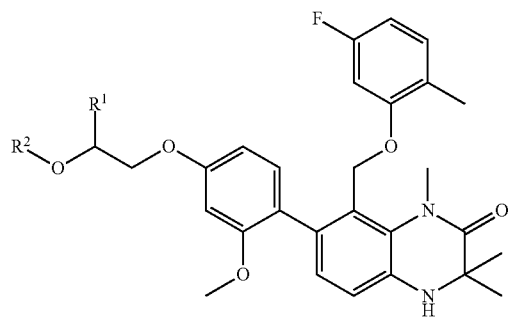

[wherein R¹ represents a hydrogen atom, a lower alkyl group which may have a substituent(s), a carboxyl group, an ester of a carboxyl group, an amide of a carboxyl group or a cyano group;

$R^2$ represents a hydrogen atom, a lower alkylcarbonyl group which may have a substituent(s), a lower cycloalkylcarbonyl group which may have a substituent(s), an arylcarbonyl group which may have a substituent(s), a heterocyclic carbonyl group which may have a substituent(s), an ester of a carboxyl group, an amide of a carboxyl group, a phosphate group or an ester of a phosphate group.]

That is, the present invention relates to the following.

Item 1. A compound represented by the following general formula (1) or a salt thereof.

(1)

[Formula 2]

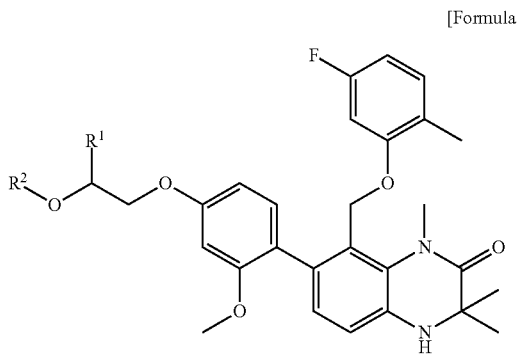

[wherein $R^1$ represents a hydrogen atom, a lower alkyl group which may have a substituent(s), a carboxyl group, an ester of a carboxyl group, an amide of a carboxyl group or a cyano group; and $R^2$ represents a hydrogen atom, a lower alkylcarbonyl group which may have a substituent(s), a lower cycloalkylcarbonyl group which may have a substituent(s), an arylcarbonyl group which may have a substituent(s), a heterocyclic carbonyl group which may have a substituent(s), an ester of a carboxyl group, an amide of a carboxyl group, a phosphate group or an ester of a phosphate group.]

Item 2. The compound or a salt thereof described in Item 1, wherein, in the general formula (1), $R^1$ represents a hydrogen atom, a lower alkyl group, a carboxyl group, an ester of a carboxyl group, an amide of a carboxyl group or a cyano group;

in the case where $R^1$ is a lower alkyl group, the lower alkyl group may have one or a plurality of groups selected from a halogen atom, a lower cycloalkyl group, an aryl group, a heterocyclic group, a hydroxyl group, an ester of a hydroxyl group, a lower alkoxyl group, a lower alkoxyl group substituted by a halogen atom(s), a lower cycloalkyloxy group, an aryloxy group, a heterocyclicoxy group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkylcarbonyl group, an arylcarbonyl group, a heterocyclic carbonyl group, a carboxyl group, an ester of a carboxyl group, an amide of a carboxyl group and a cyano group as a substituent(s);

$R^2$ represents a hydrogen atom, a lower alkylcarbonyl group, a lower cycloalkylcarbonyl group, an arylcarbonyl group, a heterocyclic carbonyl group, a carboxyl group, an ester of a carboxyl group, an amide of a carboxyl group, a phosphate group or an ester of a phosphate group; and in the case where $R^2$ is a lower alkylcarbonyl group, a lower cycloalkyl-carbonyl group, an arylcarbonyl group or a heterocyclic carbonyl group, the lower alkylcarbonyl group, the lower cycloalkylcarbonyl group, the arylcarbonyl group or the heterocyclic carbonyl group may have one or a plurality of groups selected from a halogen atom, a lower cycloalkyl group, an aryl group, a heterocyclic group, a hydroxyl group, an ester of a hydroxyl group, a lower alkoxyl group, a lower alkoxyl group substituted by a halogen atom(s), a lower cycloalkyloxy group, an aryloxy group, a heterocyclicoxy group, an amino group, a lower alkylamino group, a lower cycloalkyl-amino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkylcarbonyl group, an arylcarbonyl group, a heterocyclic carbonyl group, a carboxyl group, an ester of a carboxyl group, an amide of a carboxyl group and a cyano group as a substituent(s).

Item 3. The compound or a salt thereof described in Item 1, wherein, in the general formula (1), $R^1$ represents a hydrogen atom, a lower alkyl group, a carboxyl group or an ester of a carboxyl group;

in the case where $R^1$ is a lower alkyl group, the lower alkyl group may have one or a plurality of groups selected from a halogen atom, a hydroxyl group, a lower alkoxyl group, a lower alkylcarbonyl group, a carboxyl group, an ester of a carboxyl group, an amide of a carboxyl group and a cyano group as a substituent(s);

$R^2$ represents a hydrogen atom, a lower alkylcarbonyl group, a heterocyclic carbonyl group, a phosphate group or an ester of a phosphate group; and in the case where $R^2$ is a lower alkylcarbonyl group, the lower alkylcarbonyl group may have one or a plurality of groups selected from a halogen atom, a hydroxyl group, an ester of a hydroxyl group, a lower alkoxyl group, a lower alkoxyl group substituted by a halogen atom(s), an amino group, a lower alkylamino group, a lower alkylcarbonyl group, a carboxyl group, an ester of a carboxyl group, an amide of a carboxyl group and a cyano group as a substituent(s).

Item 4. The compound or a salt thereof described in Item 1, wherein in the general formula (1), $R^1$ represents a hydrogen atom, a lower alkyl group or an ester of a carboxyl group;

in the case where $R^1$ is a lower alkyl group, the lower alkyl group may have one or a plurality of groups selected from a halogen atom, a hydroxyl group, a carboxyl group, an ester of a carboxyl group, an amide of a carboxyl group and a cyano group as a substituent(s);

$R^2$ represents a hydrogen atom, a lower alkylcarbonyl group, a heterocyclic carbonyl group or a phosphate group; and in the case where $R^2$ is a lower alkylcarbonyl group, the lower alkylcarbonyl group may have one or a plurality of groups selected from a hydroxyl group, an amino group, a lower alkylamino group and a carboxyl group as a substituent(s).

Item 5. The compound or a salt thereof described in Item 1, wherein, in the general formula (1), $R^1$ represents a lower alkyl group;

the lower alkyl group may have one or a plurality of hydroxyl groups as a substituent(s);

$R^2$ represents a hydrogen atom or a lower alkylcarbonyl group; and in the case where R² is a lower alkylcarbonyl group, the lower alkylcarbonyl group may have one or a plurality of lower alkylamino groups as a substituent(s).

Item 6. The compound or a salt thereof described in Item 1, wherein in the general formula (1), R¹ represents methyl or 1-hydroxyethyl; and R² represents a hydrogen atom or dimethylaminomethylcarbonyl.

Item 7. A compound selected from the group consisting of
(S)-8-(5-fluoro-2-methylphenoxymethyl)-7-[4-(2-hydroxypropyl)oxy-2-methoxyphenyl]-1,3,3-trimethyl-3,4-dihydro-1H-quinoxalin-2-one,
8-(5-fluoro-2-methylphenoxymethyl)-7-[4-(2-hydroxy-3,3,3-trifluoropropyl)oxy-2-methoxyphenyl]-1,3,3-trimethyl-3,4-dihydro-1H-quinoxalin-2-one,
(R)-8-(5-fluoro-2-methylphenoxymethyl)-7-[4-(2-hydroxypropyl)oxy-2-methoxyphenyl]-1,3,3-trimethyl-3,4-dihydro-1H-quinoxalin-2-one,
(R)-8-(5-fluoro-2-methylphenoxymethyl)-7-[4-(2-hydroxybutyl)oxy-2-methoxyphenyl]-1,3,3-trimethyl-3,4-dihydro-1H-quinoxalin-2-one,
(S)-8-(5-fluoro-2-methylphenoxymethyl)-7-[4-(2-hydroxybutyl)oxy-2-methoxyphenyl]-1,3,3-trimethyl-3,4-dihydro-1H-quinoxalin-2-one,
(R)-7-[4-(2-ethoxycarbonyl-2-hydroxyethyl)oxy-2-methoxyphenyl]-8-(5-fluoro-2-methylphenoxymethyl)-1,3,3-trimethyl-3,4-dihydro-1H-quinoxalin-2-one,
(S)-7-[4-(2,4-dihydroxybutyl)oxy-2-methoxyphenyl]-8-(5-fluoro-2-methylphenoxymethyl)-1,3,3-trimethyl-3,4-dihydro-1H-quinoxalin-2-one,
(R)-7-[4-(2,4-dihydroxybutyl)oxy-2-methoxyphenyl]-8-(5-fluoro-2-methylphenoxymethyl)-1,3,3-trimethyl-3,4-dihydro-1H-quinoxalin-2-one,
(S)-8-(5-fluoro-2-methylphenoxymethyl)-7-[4-(2-hydroxyacetoxypropyl)oxy-2-methoxyphenyl]-1,3,3-trimethyl-3,4-dihydro-1H-quinoxalin-2-one,
8-(5-fluoro-2-methylphenoxymethyl)-7-[4-(2-hydroxyethyl)oxy-2-methoxyphenyl]-1,3,3-trimethyl-3,4-dihydro-1H-quinoxalin-2-one,
7-[4-(2,3-dihydroxypropyl)oxy-2-methoxyphenyl]-8-(5-fluoro-2-methylphenoxymethyl)-1,3,3-trimethyl-3,4-dihydro-1H-quinoxalin-2-one,
(S)-7-[4-(2,3-dihydroxypropyl)oxy-2-methoxyphenyl]-8-(5-fluoro-2-methylphenoxymethyl)-1,3,3-trimethyl-3,4-dihydro-1H-quinoxalin-2-one,
(R)-7-[4-(2,3-dihydroxypropyl)oxy-2-methoxyphenyl]-8-(5-fluoro-2-methylphenoxymethyl)-1,3,3-trimethyl-3,4-dihydro-1H-quinoxalin-2-one,
(R)-7-[4-(3-cyano-2-hydroxypropyl)oxy-2-methoxyphenyl]-8-(5-fluoro-2-methylphenoxymethyl)-1,3,3-trimethyl-3,4-dihydro-1H-quinoxalin-2-one,
(S)-7-[4-(3-cyano-2-hydroxypropyl)oxy-2-methoxyphenyl]-8-(5-fluoro-2-methylphenoxymethyl)-1,3,3-trimethyl-3,4-dihydro-1H-quinoxalin-2-one,
7-[4-(3-fluoro-2-hydroxypropyl)oxy-2-methoxyphenyl]-8-(5-fluoro-2-methylphenoxymethyl)-1,3,3-trimethyl-3,4-dihydro-1H-quinoxalin-2-one,
7-[4-(3-ethoxycarbonyl-2-hydroxypropyl)oxy-2-methoxyphenyl]-8-(5-fluoro-2-methylphenoxymethyl)-1,3,3-trimethyl-3,4-dihydro-1H-quinoxalin-2-one,
7-[4-(3-t-butoxycarbonyl-2-hydroxypropyl)oxy-2-methoxyphenyl]-8-(5-fluoro-2-methylphenoxymethyl)-1,3,3-trimethyl-3,4-dihydro-1H-quinoxalin-2-one,
7-[4-(3,3-dimethyl-2-hydroxybutyl)oxy-2-methoxyphenyl]-8-(5-fluoro-2-methylphenoxymethyl)-1,3,3-trimethyl-3,4-dihydro-1H-quinoxalin-2-one,
7-[4-(3-carboxy-2-hydroxypropyl)oxy-2-methoxyphenyl]-8-(5-fluoro-2-methylphenoxymethyl)-1,3,3-trimethyl-3,4-dihydro-1H-quinoxalin-2-one,
8-(5-fluoro-2-methylphenoxymethyl)-7-[4-[3-(N-pyrrolidylcarbonyl)-2-hydroxy-propyl]oxy-2-methoxyphenyl]-1,3,3-trimethyl-3,4-dihydro-1H-quinoxalin-2-one,
8-(5-fluoro-2-methylphenoxymethyl)-7-[4-[3-(N-morpholino)carbonyl-2-hydroxy-propyl]oxy-2-methoxyphenyl]-1,3,3-trimethyl-3,4-dihydro-1H-quinoxalin-2-one,
8-(5-fluoro-2-methylphenoxymethyl)-7-[4-[3-(N-piperidino)carbonyl-2-hydroxy-propyl]oxy-2-methoxyphenyl]-1,3,3-trimethyl-3,4-dihydro-1H-quinoxalin-2-one,
(S)-7-[4-[2-(N,N-dimethylaminoacetoxy)propyl]oxy-2-methoxyphenyl]-8-(5-fluoro-2-methylphenoxymethyl)-1,3,3-trimethyl-3,4-dihydro-1H-quinoxalin-2-one,
8-(5-fluoro-2-methylphenoxymethyl)-7-[4-[(2S)-[(2S)-pyrrolidylcarbonyloxy]-propyl]oxy-2-methoxyphenyl]-1,3,3-trimethyl-3,4-dihydro-1H-quinoxalin-2-one,
(R)-7-[4-[2-(N,N-dimethylaminoacetoxy)propyl]oxy-2-methoxyphenyl]-8-(5-fluoro-2-methylphenoxymethyl)-1,3,3-trimethyl-3,4-dihydro-1H-quinoxalin-2-one,
(S)-7-[4-(2-aminoacetoxypropyl)oxy-2-methoxyphenyl]-8-(5-fluoro-2-methyl-phenoxymethyl)-1,3,3-trimethyl-3,4-dihydro-1H-quinoxalin-2-one,
7-[4-[(2S)-[(2S)-amino-3-methylbutanoyloxy]propyl]oxy-2-methoxyphenyl]-8-(5-fluoro-2-methylphenoxymethyl)-1,3,3-trimethyl-3,4-dihydro-1H-quinoxalin-2-one,
(S)-7-[4-[2-(3-carboxypropanoyloxy)propyl]oxy-2-methoxyphenyl]-8-(5-fluoro-2-methylphenoxymethyl)-1,3,3-trimethyl-3,4-dihydro-1H-quinoxalin-2-one,
(S)-7-[4-[2-(2,3-dihydroxypropanoyl)oxypropyl]oxy-2-methoxyphenyl]-8-(5-fluoro-2-methylphenoxymethyl)-1,3,3-trimethyl-3,4-dihydro-1H-quinoxalin-2-one,
7-[4-[(2S)-[(2S)-amino-3-hydroxypropanoyloxy]propyl]oxy-2-methoxyphenyl]-8-(5-fluoro-2-methylphenoxymethyl)-1,3,3-trimethyl-3,4-dihydro-1H-quinoxalin-2-one,
(S)-8-(5-fluoro-2-methylphenoxymethyl)-7-[4-(2-phosphonohydroxypropyl)oxy-2-methoxyphenyl]-1,3,3-trimethyl-3,4-dihydro-1H-quinoxalin-2-one,
(S)-8-(5-fluoro-2-methylphenoxymethyl)-7-[4-(2-phosphonohydroxybutyl)oxy-2-methoxyphenyl]-1,3,3-trimethyl-3,4-dihydro-1H-quinoxalin-2-one and,
(S)-7-[4-(3-cyano-2-phosphonohydroxypropyl)oxy-2-methoxyphenyl]-8-(5-fluoro-2-methylphenoxymethyl)-1,3,3-trimethyl-3,4-dihydro-1H-quinoxalin-2-one or a salt thereof.

Item 8. A pharmaceutical composition comprising the compound or a salt thereof described in any one of Items 1 to 7.

Item 9. A glucocorticoid receptor agonist comprising the compound or a salt thereof described in any one of Items 1 to 7 as an active ingredient.

Item 10. A glucocorticoid receptor activator comprising the compound or a salt thereof described in any one of Items 1 to 7 as an active ingredient.

Item 11. A prophylactic or therapeutic agent for a glucocorticoid receptor related disease, which comprises the compound or a salt thereof described in any one of Items 1 to 7 as an active ingredient.

Item 12. The prophylactic or therapeutic agent described in Item 11, wherein the glucocorticoid receptor related disease is at least one selected from the group consisting of endocrine diseases, collagen diseases, kidney diseases, heart diseases, allergic diseases, blood diseases, digestive system diseases, liver diseases, pulmonary diseases, severe infectious diseases, tuberculosis disease, nervous disease, malignant tumor, digestive organ symptoms accompanied by administration of an anti-malignant tumor agent, surgery related diseases, obstetrics and gynecology related diseases, urology related diseases, skin diseases, otolaryngology related diseases, oral surgery related diseases, glaucoma, rheumatic diseases and inflammatory diseases.

Item 13. The prophylactic or therapeutic agent described in Item 12, wherein the inflammatory disease is at least one selected from the group consisting of inflammatory bone or joint disease, ocular inflammatory disease, asthma, bronchitis, rhinitis, dermatitis and inflammatory bowel disease.

Item 14. The prophylactic or therapeutic agent described in Item 13, wherein the inflammatory bone or joint disease is at least one selected from the group consisting of rheumatoid arthritis, juvenile rheumatoid arthritis, osteoarthritis, osteoporosis and spondylarthritis.

Item 15. The prophylactic or therapeutic agent described in Item 13, wherein the ocular inflammatory disease is an anterior eye inflammatory disease.

Item 16. The prophylactic or therapeutic agent described in Item 13, wherein the ocular inflammatory disease is a posterior eye inflammatory disease.

Item 17. The prophylactic or therapeutic agent described in Item 15, wherein the anterior eye inflammatory disease is at least one selected from the group consisting of keratitis, keratoconjunctivitis, conjunctivitis, blepharitis, dry eye syndrome, allergic conjunctivitis, uveitis, inflammation after anterior eye surgery and inflammation due to rejection of ocular tissue transplantation.

Item 18. The prophylactic or therapeutic agent described in Item 16, wherein the posterior eye inflammatory disease is at least one selected from the group consisting of age-related macular degeneration, diabetic retinopathy, diabetic macular edema, neovascular maculopathy, proliferative vitreoretinopathy, central retinal vein occlusion, central retinal artery occlusion, branch retinal vein occlusion, branch retinal artery occlusion, inflammation or degeneration of posterior eye caused by external injury, retinitis, uveitis, scleritis and optic neuritis.

Item 19. The compound or a salt thereof described in any one of Items 1 to 7 for use in the prophylaxis or treatment of a glucocorticoid receptor related disease.

Item 20. The compound or a salt thereof described in Item 19, wherein the glucocorticoid receptor related disease is at least one selected from the group consisting of endocrine diseases, collagen diseases, kidney diseases, heart diseases, allergic diseases, blood diseases, digestive system diseases, liver diseases, pulmonary diseases, severe infectious diseases, tuberculosis disease, nervous disease, malignant tumor, digestive organ symptoms accompanied by administration of an anti-malignant tumor agent, surgery related diseases, obstetrics and gynecology related diseases, urology related diseases, skin diseases, otolaryngology related diseases, oral surgery related diseases, glaucoma, rheumatic diseases and inflammatory diseases.

Item 21. The compound or a salt thereof described in Item 20, wherein the inflammatory disease is at least one selected from the group consisting of inflammatory bone or joint disease, ocular inflammatory diseases, asthma, bronchitis, rhinitis, dermatitis and inflammatory bowel disease.

Item 22. The compound or a salt thereof described in Item 21, wherein the inflammatory bone or joint disease is at least one selected from the group consisting of rheumatoid arthritis, juvenile rheumatoid arthritis, osteoarthritis, osteoporosis and spondylarthritis.

Item 23. The compound or a salt thereof described in Item 21, wherein the ocular inflammatory disease is an anterior eye inflammatory disease.

Item 24. The compound or a salt thereof described in Item 21, wherein the ocular inflammatory disease is a posterior eye inflammatory disease.

Item 25. The compound or a salt thereof described in Item 23, wherein the anterior eye inflammatory disease is at least one selected from the group consisting of keratitis, keratoconjunctivitis, conjunctivitis, blepharitis, dry eye syndrome, allergic conjunctivitis, uveitis, inflammation after anterior eye surgery and inflammation due to rejection of ocular tissue transplantation.

Item 26. The compound or a salt thereof described in Item 24, wherein the posterior eye inflammatory disease is at least one selected from the group consisting of age-related macular degeneration, diabetic retinopathy, diabetic macular edema, neovascular maculopathy, proliferative vitreoretinopathy, central retinal vein occlusion, central retinal artery occlusion, branch retinal vein occlusion, branch retinal artery occlusion, inflammation or degeneration of posterior eye caused by external injury, retinitis, uveitis, scleritis and optic neuritis.

Item 27. Use of the compound or a salt thereof described in any one of Items 1 to 7 for the use of the manufacture of a medicament for the prophylaxis or treatment of a glucocorticoid receptor related disease.

Item 28. The use of Item 27, wherein the glucocorticoid receptor related disease is at least one selected from the group consisting of endocrine diseases, collagen diseases, kidney diseases, heart diseases, allergic diseases, blood diseases, digestive system diseases, liver diseases, pulmonary diseases, severe infectious diseases, tuberculosis disease, nervous disease, malignant tumor, digestive organ symptoms accompanied by administration of an anti-malignant tumor agent, surgery related diseases, obstetrics and gynecology related diseases, urology related diseases, skin diseases, otolaryngology related diseases, oral surgery related diseases, glaucoma, rheumatic diseases and inflammatory diseases.

Item 29. The use described in Item 28, wherein the inflammatory disease is at least one selected from the group consisting of inflammatory bone or joint disease, ocular inflammatory disease, asthma, bronchitis, rhinitis, dermatitis and inflammatory bowel disease.

Item 30. The use described in Item 29, wherein the inflammatory bone or joint disease is at least one selected from the group consisting of rheumatoid arthritis, juvenile rheumatoid arthritis, osteoarthritis, osteoporosis and spondylarthritis.

Item 31. The use described in Item 29, wherein the ocular inflammatory disease is an anterior eye inflammatory disease.

Item 32. The use described in Item 29, wherein the ocular inflammatory disease is a posterior eye inflammatory disease.

Item 33. The use described in Item 31, wherein the anterior eye inflammatory disease is at least one selected from the group consisting of keratitis, keratoconjunctivitis, conjunctivitis, blepharitis, dry eye syndrome, allergic conjunctivitis, uveitis, inflammation after anterior eye surgery and inflammation due to rejection of ocular tissue transplantation.

Item 34. The use described in Item 32, wherein the posterior eye inflammatory disease is at least one selected from the group consisting of age-related macular degeneration, diabetic retinopathy, diabetic macular edema, neovascular maculopathy, proliferative vitreoretinopathy, central retinal vein occlusion, central retinal artery occlusion, branch retinal vein occlusion, branch retinal artery occlusion, inflammation or degeneration of posterior eye caused by external injury, retinitis, uveitis, scleritis and optic neuritis.

Item 35. A method for the prophylaxis or treatment of a glucocorticoid receptor related disease, which comprises administering an effective amount of the compound or a salt thereof described in any one of Items 1 to 7.

Item 36. The method for the prophylaxis or treatment described in Item 35, wherein the glucocorticoid receptor related disease is at least one selected from the group consisting of endocrine diseases, collagen diseases, kidney diseases, heart diseases, allergic diseases, blood diseases, digestive system diseases, liver diseases, pulmonary diseases, severe infectious diseases, tuberculosis disease, nervous disease, malignant tumor, digestive organ symptoms accompanied by administration of an anti-malignant tumor agent, surgery related diseases, obstetrics and gynecology related diseases, urology related diseases, skin diseases, otolaryngology related diseases, oral surgery related diseases, glaucoma, rheumatic diseases and inflammatory diseases.

Item 37. The method for the prophylaxis or treatment described in Item 36, wherein the inflammatory disease is at least one selected from the group consisting of inflammatory bone or joint disease, ocular inflammatory disease, asthma, bronchitis, rhinitis, dermatitis and inflammatory bowel disease.

Item 38. The method for the prophylaxis or treatment described in Item 37, wherein the inflammatory bone or joint disease is at least one selected from the group consisting of rheumatoid arthritis, juvenile rheumatoid arthritis, osteoarthritis, osteoporosis and spondylarthritis.

Item 39. The method for the prophylaxis or treatment described in Item 37, wherein the ocular inflammatory disease is an anterior eye inflammatory disease.

Item 40. The method for the prophylaxis or treatment described in Item 37, wherein the ocular inflammatory disease is a posterior eye inflammatory disease.

Item 41. The method for the prophylaxis or treatment described in Item 39, wherein the anterior eye inflammatory disease is at least one selected from the group consisting of keratitis, keratoconjunctivitis, conjunctivitis, blepharitis, dry eye syndrome, allergic conjunctivitis, uveitis, inflammation after anterior eye surgery and inflammation due to rejection of ocular tissue transplantation.

Item 42. The method for the prophylaxis or treatment described in Item 40, wherein the posterior eye inflammatory disease is at least one selected from the group consisting of age-related macular degeneration, diabetic retinopathy, diabetic macular edema, neovascular maculopathy, proliferative vitreoretinopathy, central retinal vein occlusion, central retinal artery occlusion, branch retinal vein occlusion, branch retinal artery occlusion, inflammation or degeneration of posterior eye caused by external injury, retinitis, uveitis, scleritis and optic neuritis.

Item 43. A pharmaceutical composition for the prophylaxis or treatment of a glucocorticoid receptor related disease, which comprises the compound or a salt thereof described in any one of Items 1 to 7 as an active ingredient.

Item 44. The pharmaceutical composition for the prophylaxis or treatment described in Item 43, wherein the glucocorticoid receptor related disease is at least one selected from the group consisting of endocrine diseases, collagen diseases, kidney diseases, heart diseases, allergic diseases, blood diseases, digestive system diseases, liver diseases, pulmonary diseases, severe infectious diseases, tuberculosis disease, nervous disease, malignant tumor, digestive organ symptoms accompanied by administration of an anti-malignant tumor agent, surgery related diseases, obstetrics and gynecology related diseases, urology related diseases, skin diseases, otolaryngology related diseases, oral surgery related diseases, glaucoma, rheumatic diseases and inflammatory diseases.

Item 45. The pharmaceutical composition for the prophylaxis or treatment described in Item 44, wherein the inflammatory disease is at least one selected from the group consisting of inflammatory bone or joint disease, ocular inflammatory disease, asthma, bronchitis, rhinitis, dermatitis and inflammatory bowel disease.

Item 46. The pharmaceutical composition for the prophylaxis or treatment described in Item 45, wherein the inflammatory bone or joint disease is at least one selected from the group consisting of rheumatoid arthritis, juvenile rheumatoid arthritis, osteoarthritis, osteoporosis and spondylarthritis.

Item 47. The pharmaceutical composition for the prophylaxis or treatment described in Item 45, wherein the ocular inflammatory disease is an anterior eye inflammatory disease.

Item 48. The pharmaceutical composition for the prophylaxis or treatment described in Item 45, wherein the ocular inflammatory disease is a posterior eye inflammatory disease.

Item 49. The pharmaceutical composition for the prophylaxis or treatment described in Item 47, wherein the anterior eye inflammatory disease is at least one selected from the group consisting of keratitis, keratoconjunctivitis, conjunctivitis, blepharitis, dry eye syndrome, allergic conjunctivitis, uveitis, inflammation after anterior eye surgery and inflammation due to rejection of ocular tissue transplantation.

Item 50. The pharmaceutical composition for the prophylaxis or treatment described in Item 48, wherein the posterior eye inflammatory disease is at least one selected from the group consisting of age-related macular degeneration, diabetic retinopathy, diabetic macular edema, neovascular maculopathy, proliferative vitreoretinopathy, central retinal vein occlusion, central retinal artery occlusion, branch retinal vein occlusion, branch retinal artery occlusion, inflammation or degeneration of posterior eye caused by external injury, retinitis, uveitis, scleritis and optic neuritis.

Effects of the Invention

The present invention can provide a novel [4-(1,3,3-trimethyl-2-oxo-3,4-dihydro-1H-quinoxalin-7-yl)phenoxy] ethyloxy compound or a salt thereof. The compound of the present invention has excellent glucocorticoid receptor agonist activity, and is useful as a medicament, in particular, as a prophylactic or therapeutic agent for glucocorticoid receptor related disease, i.e., endocrine diseases, collagen diseases, kidney diseases, heart diseases, allergic diseases, blood diseases, digestive system diseases, liver diseases, pulmonary diseases, severe infectious diseases, tuberculosis disease, nervous disease, malignant tumor, digestive organ symptoms accompanied by administration of an anti-malignant tumor agent, surgery related diseases, obstetrics and gynecology related diseases, urology related diseases, skin diseases, otolaryngology related diseases, oral surgery related diseases, glaucoma, rheumatic diseases, inflammatory diseases, etc.

EMBODIMENTS TO CARRY OUT THE INVENTION

Hereinafter, definitions of terms (atoms, groups, rings and the like) to be used in this specification will be described in detail.

The "halogen atom" refers to a fluorine, chlorine, bromine or iodine atom.

The "lower alkyl group" refers to a straight chain or branched alkyl group having 1 to 8, preferably 1 to 6, and particularly preferably 1 to 4 carbon atoms. Specific examples thereof include methyl, ethyl, n-propyl, n-butyl, n-pentyl, n-hexyl, n-heptyl, n-octyl, isopropyl, isobutyl, sec-butyl, tert-butyl and isopentyl groups and the like.

The "lower cycloalkyl group" refers to a cycloalkyl group having 3 to 8, preferably 3 to 6 carbon atoms. Specific examples thereof include cyclopropyl, cyclobutyl, cyclopentyl, cyclohexyl, cycloheptyl and cyclooctyl groups.

The "aryl group" refers to a residue formed by removing one hydrogen atom from a monocyclic aromatic hydrocarbon group, or bicyclic or tricyclic condensed polycyclic aromatic hydrocarbon having 6 to 14 carbon atoms. Specific examples thereof include phenyl, naphthyl, anthryl and phenanthryl groups and the like.

The "heterocyclic group" refers to a residue formed by removing one hydrogen atom from a saturated or unsaturated monocyclic heterocyclic ring (preferably, a saturated or unsaturated monocyclic hetero 5 or 6-membered ring having 3 to 5 carbon atoms, which has one or two heteroatoms in the ring), or a bicyclic or tricyclic condensed polycyclic heterocyclic ring (preferably, a bicyclic or tricyclic condensed polycyclic hetero ring having 7 to 13 carbon atoms, which has one or two heteroatoms in the ring) having one or a plurality of heteroatoms selected from a nitrogen atom, an oxygen atom and a sulfur atom in the ring.

Specific examples of the saturated monocyclic heterocyclic ring include pyrrolidine, pyrazolidine, imidazolidine, triazolidine, piperidine, hexahydropyridazine, hexahydropyrimidine, piperazine, homopiperidine and homopiperazine rings and the like having nitrogen atom in the ring, tetrahydrofuran and tetrahydropyran rings and the like having oxygen atom in the ring, tetrahydrothiophene and tetrahydrothiopyran rings and the like having a sulfur atom in the ring, oxazolidine, isoxazolidine and morpholine rings and the like having nitrogen atom and oxygen atom in the ring, and thiazolidine, isothiazolidine and thiomorpholine rings and the like having nitrogen atom and sulfur atom in the ring.

Further, such a saturated monocyclic heterocyclic ring can be condensed with a benzene ring or the like to form a bicyclic or tricyclic condensed polycyclic heterocyclic ring such as a dihydroindole, dihydroindazole, dihydrobenzimidazole, tetrahydro-quinoline, tetrahydroisoquinoline, tetrahydrocinnoline, tetrahydrophthalazine, tetrahydroquinazoline, tetrahydroquinoxaline, dihydrobenzofuran, dihydroisobenzo-furan, chromane, isochromane, dihydrobenzothiophene, dihydroi sobenzothiophene, thiochromane, isothiochromane, dihydrobenzoxazole, dihydrobenzisoxazole, dihydrobenzoxazine, dihydrobenzothiazole, dihydrobenzisothiazole, dihydrobenzo-thiazine, xanthene, 4a-carbazole, or perimidine ring.

Specific examples of the unsaturated monocyclic heterocyclic ring include dihydropyrrole, pyrrole, dihydropyrazole, pyrazole, dihydroimidazole, imidazole, dihydrotriazole, triazole, tetrahydropyridine, dihydropyridine, pyridine, tetrahydro-pyridazine, dihydropyridazine, pyridazine, tetrahydropyrimidine, dihydropyrimidine, pyrimidine, tetrahydropyrazine, dihydropyrazine and pyrazine rings and the like having nitrogen atom in the ring, dihydrofuran, furan, dihydropyran and pyran rings and the like having oxygen atom in the ring, dihydrothiophene, thiophene, dihydrothiopyran and thiopyran rings and the like having sulfur atom in the ring, dihydrooxazole, oxazole, dihydroisoxazole, isoxazole, dihydrooxazine and oxazine rings and the like having nitrogen atom and oxygen atom in the ring, dihydrothiazole, thiazole, dihydroisothiazole, isothiazole, dihydrothiazine and thiazine rings and the like having nitrogen atom and sulfur atom in the ring.

Further, such an unsaturated monocyclic heterocyclic ring can be condensed with a benzene ring or the like to form a bicyclic or tricyclic condensed polycyclic heterocyclic ring such as an indole, indazole, benzimidazole, benzotriazole, dihydroquinoline, quinoline, dihydroisoquinoline, isoquinoline, phenanthridine, dihydrocinnoline, cinnoline, dihydrophthalazine, phthalazine, dihydroquinazoline, quinazoline, dihydroquinoxaline, quinoxaline, benzofuran, isobenzofuran, chromene, isochromene, benzothiophene, isobenzothiophene, thiochromene, isothiochromene, benzoxazole, benzisoxazole, benzoxazine, benzothiazole, benzisothiazole, benzothiazine, phenoxanthin, carbazole, f3-carboline, phenanthridine, acridine, phenanthroline, phenazine, phenothiazine or phenoxazine ring.

The "lower alkoxy group" refers to a group formed by replacing the hydrogen atom of a hydroxyl group with a lower alkyl group. Specific examples thereof include methoxy, ethoxy, n-propoxy, n-butoxy, n-pentoxy, n-hexyloxy, n-heptyloxy, n-octyl-oxy, isopropoxy, isobutoxy, sec-butoxy, tert-butoxy and isopentoxy groups and the like.

The "lower cycloalkyloxy group" refers to a group formed by replacing the hydrogen atom of a hydroxyl group with a lower cycloalkyl group. Specific examples thereof include cyclopropyloxy, cyclobutyloxy, cyclopentyloxy, cyclohexyloxy, cycloheptyloxy and cyclooctyloxy groups and the like.

The "aryloxy group" refers to a group formed by replacing the hydrogen atom of a hydroxyl group with an aryl group. Specific examples thereof include phenoxy, naphthoxy, anthryloxy and phenanthryloxy groups and the like.

The "heterocyclic oxy group" refers to a group formed by replacing the hydrogen atom of a hydroxyl group with a heterocyclic group. Specific examples thereof include pyrrolidinyloxy, piperidinyloxy, piperazinyloxy, tetrahydrofuranyloxy, morpholinyloxy, pyrazolyloxy, imidazolyloxy, pyridinyloxy, pyrimidinyloxy, furanyloxy, thiazolyloxy, quinolyloxy, quinazolyloxy, benzofuranyloxy and benzothiazolyloxy groups and the like.

The "lower alkylamino group" refers to a group formed by replacing one or both of the hydrogen atoms of an amino group with a lower alkyl group(s). Specific examples thereof include methylamino, ethylamino, propylamino, dimethylamino, diethylamino and ethyl(methyl)amino groups and the like.

The "lower cycloalkylamino group" refers to a group formed by replacing one or both hydrogen atoms of an amino group with a lower cycloalkyl group(s), and in the case where the group represents one formed by replacing one of the hydrogen atoms of the amino group with a lower cycloalkyl group, the other represents a hydrogen atom or a group in which the hydrogen atom is replaced with a lower alkyl group. Specific examples thereof include cyclopropylamino, cyclobutylamino, cyclopentylamino, cyclohexylamino, cycloheptylamino, cyclooctylamino, dicyclohexylamino and cyclohexyl(methyl)amino groups and the like.

The "arylamino group" refers to a group formed by replacing one or both of the hydrogen atoms of amino group with aryl group(s), and in the case where the group represents one formed by replacing one of the hydrogen atoms of the amino group with an aryl group, the other represents a hydrogen atom or a group in which the hydrogen atom is replaced with a lower alkyl group or lower cycloalkyl group.

Specific examples thereof include phenylamino, naphthylamino, anthrylamino, phenanthryl-amino, diphenylamino, methyl (phenyl) amino, ethyl (phenyl) amino and cyclohexyl (phenyl) amino groups and the like.

The "heterocyclic amino group" refers to a group formed by replacing one or both of the hydrogen atoms of amino group with heterocyclic group(s), and in the case where the group represents one formed by replacing one of the hydrogen atoms of the amino group with a heterocyclic group, the other represents a hydrogen atom or a group in which the hydrogen atom is replaced with a lower alkyl group, lower cycloalkyl group or aryl group. Specific examples thereof include piperidinylamino, N-methyl-N-piperidinylamino, N-phenyl-N-piperidinylamino, piperazinylamino, morpholinylamino, N-methyl-N-morpholinyl amino, N-cyclopropyl-N-morpholinylamino, pyridinylamino and N-methyl-N-pyridinylamino groups and the like.

The "lower alkylcarbonyl group" refers to a group formed by replacing the hydrogen atom of a formyl group with a lower alkyl group. Specific examples thereof include methylcarbonyl, ethylcarbonyl, n-propylcarbonyl, n-butylcarbonyl, n-pentyl-carbonyl, n-hexylcarbonyl, n-heptylcarbonyl, n-octylcarbonyl, isopropylcarbonyl, isobutylcarbonyl, sec-butylcarbonyl, tert-butylcarbonyl and isopentylcarbonyl groups and the like.

The "lower cycloalkylcarbonyl group" refers to a group formed by replacing the hydrogen atom of a formyl group with a lower cycloalkyl group. Specific examples thereof include cyclopropylcarbonyl, cyclobutylcarbonyl, cyclopentyl-carbonyl, cyclohexylcarbonyl, cycloheptylcarbonyl and cyclooctylcarbonyl groups.

The "arylcarbonyl group" refers to a group formed by replacing the hydrogen atom of a formyl group with an aryl group. Specific examples thereof include phenylcarbonyl, naphthylcarbonyl, anthrylcarbonyl and phenanthrylcarbonyl groups and the like.

The "heterocyclic carbonyl group" refers to a group formed by replacing the hydrogen atom of a formyl group with a heterocyclic group. Specific examples thereof include pyrrolidinylcarbonyl, piperidinylcarbonyl, piperazinylcarbonyl, tetrahydrofuranylcarbonyl, morpholinylcarbonyl, pyrazolylcarbonyl, imidazolyl-carbonyl, pyridinylcarbonyl, pyrimidinylcarbonyl, furanylcarbonyl, thiazolylcarbonyl, quinolylcarbonyl, quinazolylcarbonyl, benzofuranylcarbonyl and benzothiazolyl-carbonyl group and the like.

The "phosphate group" refers to a group represented by —PO(OH)$_2$.

The "ester of a hydroxyl group" refers to a group represented by —OCO—R$^a$.

Here, "R$^a$" represents a lower alkyl group which may have a substituent(s), a lower cycloalkyl group which may have a substituent(s), an aryl group which may have a substituent(s), a heterocyclic group which may have a substituent(s), a lower alkoxy group which may have a substituent(s), a lower cycloalkyloxy group which may have a substituent(s), an aryloxy group which may have a substituent(s), a heterocyclicoxy group which may have a substituent(s), an amino group, a lower alkylamino group which may have a substituent(s), a lower cycloalkylamino group which may have a substituent(s), an arylamino group which may have a substituent(s) or a heterocyclic amino group which may have a substituent(s). In the following, "R$^a$" is the same.

The "amide of an amino group" refers to a group represented by —NHCO—R$^a$. Here, "R$^a$" is the same as mentioned above.

The "amide of a lower alkylamino group" refers to a group represented by —NR$^b$CO—R$^a$. Here, "R$^b$" represents a lower alkyl group which may have a substituent(s), and "R$^a$," is the same as mentioned above.

The "amide of a lower cycloalkylamino group" refers to a group represented by —NR$^c$CO—R$^a$. Here, "R$^c$" represents a lower cycloalkyl group which may have a substituent(s), and "R$^a$" is the same as mentioned above.

The "amide of an arylamino group" refers to a group represented by —NR$^d$CO—R$^a$. Here, "R$^d$" represents an aryl group which may have a substituent(s), and "R$^a$," is the same as mentioned above.

The "amide of a heterocyclic amino group" refers to a group represented by —NR$^e$CO—R$^a$. Here, "R$^e$" represents a heterocyclic group which may have a substituent(s), and "R$^a$" is the same as mentioned above.

The "ester of a carboxyl group" refers to a group represented by —COOR$^f$. Here, "R$^f$" represents a lower alkyl group which may have a substituent(s), a lower cycloalkyl group which may have a substituent(s), an aryl group which may have a substituent(s) or a heterocyclic group which may have a substituent(s).

The "amide of a carboxyl group" refers to a group represented by —CONR$^g$R$^h$. Here, "R$^g$" and "R$^h$" may be the same or different from each other, and each represent a hydrogen atom, a lower alkyl group which may have a substituent(s), a lower cycloalkyl group which may have a substituent(s), an aryl group which may have a substituent(s) or a heterocyclic group which may have a substituent(s), or "R$^g$" and "R$^h$" are combined to form a heterocyclic ring.

The "ester of a phosphate group" refers to a group represented by —PO(OR$^j$)$_2$. Here, "R$^j$" represents a lower alkyl group.

The "lower alkyl group which may have a substituent(s)", "lower alkylcarbonyl group which may have a substituent(s)", "lower alkoxy group which may have a substituent(s)", or "a lower alkylamino group which may have a substituent(s)" refer to a "lower alkyl group", a "lower alkylcarbonyl group", a "lower alkoxy group", or "a lower alkylamino group" in which the lower alkyl portion thereof may have one or a plurality of substituents selected from the following a group, respectively.

The "α group" refers to a halogen atom, a lower cycloalkyl group, an aryl group, a heterocyclic group, a hydroxyl group, an ester of a hydroxyl group, a lower alkoxyl group, a lower alkoxyl group substituted by a halogen atom(s), a lower cycloalkyloxy group, an aryloxy group, a heterocyclicoxy group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkyl-carbonyl group, an arylcarbonyl group, a heterocyclic carbonyl group, a carboxyl group, an ester of a carboxyl group, an amide of a carboxyl group, a nitro group and a cyano group.

The "lower cycloalkylcarbonyl group which may have a substituent(s)", the "arylcarbonyl group which may have a substituent(s)", the "heterocyclic carbonyl group which may have a substituent(s)", the "lower cycloalkyl group which may have a substituent(s)", the "aryl group which may have a substituent(s)", the "heterocyclic group which may have a substituent(s)", the "cycloalkyloxy group which may have a substituent(s)", the "aryloxy group which may have a substituent(s)", the "heterocyclic-oxy group which may have a substituent(s)", the "cycloalkylamino group which may have a substituent(s)" or the "arylamino group which may have a substituent(s)" refer to the "lower cycloalkylcarbonyl group which may have a substituent(s)", the "arylcarbon-yl group which may have a substituent(s)", the "heterocyclic carbonyl group which may have a substituent(s)", the "lower cycloalkyl group which may have a substituent(s)", the "aryl group which may have a substituent(s)", the "heterocyclic group which may have a substituent(s)", the "cycloalkyloxy group which may have a substituent(s)", the "aryloxy group which may have a substituent(s)", the "heterocyclicoxy group which may have a substituent(s)", the "cycloalkylamino group which may have a substi-tuent(s)" or the "arylamino group which may have a substituent(s)" in which the lower cycloalkyl portion thereof, the aryl portion, and the heterocyclic portion may have one or a plurality of substituents selected from the above-mentioned a group, respectively.

The term "a plurality of groups" as used in the present invention means that each group may be the same or different and the number of groups is two or more at the site to be substituted and the number of substitutable groups or less, and the number is preferably in the case of 2 or 3. Further, a hydrogen atom and a halogen atom are also included in the concept of the "group".

The "salt" of the present compound is not particularly limited as long as it is a pharmaceutically acceptable salt. There may be mentioned, for example, salts with an inorganic acid such as hydrochloric acid, hydrobromic acid, hydroiodic acid, nitric acid, sulfuric acid or phosphoric acid; salts with an organic acid such as acetic acid, fumalic acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate ester, methyl sulfate, naphthalenesulfonic acid or sulfosalicylic acid; quaternary ammonium salts with methyl bromide, methyl iodide or the like; salts with a halogen ion such as a bromine ion, a chlorine ion or an iodine ion; salts with an alkali metal such as lithium, sodium or potassium; salts with an alkaline earth metal such as calcium or magnesium; salts with a metal such as iron or zinc; salts with ammonia; salts with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine or N,N-bis(phenyl-methyl)-1,2-ethanediamine; and the like.

In the case where there are geometrical isomers and/or optical isomers in the present compound of the present invention, these isomers are also included in the scope of the present invention.

Further, in the case where there is proton tautomerism in the present compound, the tautomeric isomers thereof (keto isomer, enol isomer) are also included in the present invention.

In the case where there are hydrates and/or solvates in the present compound, these hydrates and/or solvates are also included in the scope of the present invention.

In the case where there are crystalline polymorphisms and/or crystal polymorphic group (crystal polymorphic system) in the present compound, the crystalline polymorphisms and/or crystal polymorphic group (crystal polymorphic system) thereof are also included in the present invention. Here, crystal polymorphic group (crystal polymorphic system) means crystal forms at the respective stages in the case where the crystal form changes variously and/or its entirety, depending on the conditions and/or the states (in this state, the formulated state is also included) such as manufacture thereof, crystallization, preservation or the like.

The present invention includes a pharmaceutically acceptable prodrug of the compound represented by the general formula (1) or a salt thereof. The pharma-ceutically acceptable prodrug is a compound having a group which can be converted to an amino group, a hydroxyl group, a carboxyl group or the like by solvolysis or under physiological conditions. The group which forms the prodrug may be mentioned a group described in, for example, Progress in Medicine, vol. 5, pp. 2157-2161, 1995 or "Development of Pharmaceuticals" (Hirokawa-Shoten, Limited, 1990) vol. 7, Molecular design, pp. 163-198.

In addition, the present compound can also play a role as a prodrug with the compound itself.

The "pharmaceutical composition" referred to in the present invention means a composition utilizable as a medicine. The pharmaceutical composition of the present invention may contain the present compound or a salt thereof and an additive(s) which is/are acceptable as a medicine (for example, an excipient, a binder, a disintegrant, a coating agent, a stabilizer, a corrigent (a sweetener, a sour agent or a flavor or the like), a tonicity agent, a buffer, a surfactant, a stabilizer, a preservative, a pH adjusting agent, a soothing agent), if necessary, by using a necessary amount, and can be prepared.

The "glucocorticoid receptor agonist" referred to in the present invention means a compound having an agonist action by bonding to the glucocorticoid receptor. The agonist action may be either the complete agonist action or a partial agonist action and include, for example, an IL-6 production inhibitory action, a TNFα production inhibitory action, an IL-2 production inhibitory action, an IL-4 production inhibitory action, and an MCP-1 production inhibitory action.

The glucocorticoid receptor related diseases are not specifically limited as it is a disease that can be prevented and/or treated with a glucocorticoid receptor agonist, and can be applied to a disease that can be usually prevented and/or treated with glucosteroids.

The "glucocorticoid receptor related disease" may be mentioned, for example, endocrine diseases such as chronic adrenal cortical insufficiency (primary, secondary, pituitary, iatrogenic), acute adrenal cortical insufficiency (adrenal crisis), adrenogenital syndrome, subacute thyroiditis, thyrotoxicosis [thyroid (toxic) crises], malignant exophthalmos accompanied by thyroid disease, isolated ACTH deficiency, idiopathic hypoglycemia or the like; collagen diseases such as erythematosus (systemic lupus and chronic discoid lupus), systemic lupus (including aortitis syndrome, periarteritis *nodosa*, polyarteritis, Wegener's granulomatosis), polymyositis (dermatomyositis), scleroderma, or the like; kidney diseases such as nephrosis, nephrosis syndrome, or the like; heart diseases such as congestive heart failure, or the like; allergic diseases such as bronchial asthma, asthmatic bronchitis (including infantile asthmatic bronchitis), allergy or intoxication by drugs or other chemical substances (including drug rash, intoxication dermatosis), serum sickness, or the like; blood diseases such as purpura (therombocytopenic and nonthrombocytopenic), aplastic anemia, leukemia (including acute leukemia, blastic crisis of chronic myelogenous leukemia, chronic lymphocytic leukemia, leukemia of skin), hemolytic anemia, agranulocytosis, or the like; digestive system diseases such as ulcerative colitis, regional enteritis, improvement in systemic conditions of severe degenerative disease (including cancer last stage, sprue), or the like; liver diseases such as acute hepatitis, cholestatic acute hepatitis, chronic hepatitis, hepatic cirrhosis, or the like; pulmonary diseases such as sarcoidosis, diffuse interstitial pneumonia (including pulmonary fibrosis, irradiation pneumonitis), or the like; severe infectious diseases; tuberculosis disease such as pulmonary tuberculosis, tuberculous meningitis, tuberculous pleurisy, tuberculous peritonitis, tuberculous pericarditis, or the like; nervous disease such as encephalo-myelitis (including encephalitis, myelitis), peripheral neuritis (including Guillain-Barre syndrome), myotonia congenita, myasthenia gravis, multiple sclerosis (including fasciculus opticus myelitis), chorea minor, facial paralysis, spinal retinitis, or the like; malignant tumor such as malignant lymphoma (lymphosarcomatosis, reticulosarcomatosis, Hodgkin's disease, cutaneous reticulosis, mycosis fungoides) and similar diseases (related diseases), eosinophilic granuloma, recurrence and transition of breast cancer, or the like; digestive symptoms (nausea, vomiting) resulting from administration of an anti-malignant tumor agent (cisplatin or the like); surgery related diseases such as adrenalectomy, surgical invasion of patients with adrenocortical insufficiency, pulmonary edema after invasion, organ or tissue transplantation, snake venom or insect venom (including severe insect bite), fever of unknown origin, or the like; obstetrics and gynecology related diseases such as prevention of adhesion after fallopian tube surgery, or the like; urology related diseases such as prostatic cancer, penile induration, or the like; skin diseases such as eczema and dermatitis group (acute eczema, subacute eczema, chronic eczema, contact dermatitis, nummular eczema, autosensitization dermatitis, atopic dermatitis, infantile eczema, lichen simplex chronicus Vidal, other neurodermatitis, seborrheic dermatitis, keratodermia tylodes palmaris progressiva, other dermatitis of hands and fingers, genital or anal eczema, auricular and ear canal eczema and dermatitis, nasal vestibule and nose wings peripheral eczema and dermatitis, or the like), prurigo group (including strophulus infantum, strophulus, urticaria perstans), urticaria, psoriasis and similar diseases (psoriasis vulgaris (serious cases), arthropathic psoriasis, psoriatic erythroderma, pustular psoriasis, acrodermatitis continua suppurativa hallopeau, herpetiform impetigo, Reiter syndrome), palmoplantar pustulosis, lichen planus, scleredema adultorum, erythema group (erythema exudativum multiforme, erythema nodosum), anaphylactoid purpura (simple type, Schonlein type, Henoch type), Weber Christian disease, mucocutaneous ocular syndrome (ectodermosis erosiva pluriorificialis, Stevens-Johnson disease, dermatostomatitis, Fuchs syndrome, Behcet's disease, Lipschutz' acute genital ulcer), Raynaud disease, alopecia areata, pemphigus group (pemphigus vulgaris, pemphigus foliaceus, Senear-Usher syndrome, pemphigus vegetans), dermatitis herpetiformis (Duhring) (including pemphigoid, gestational herpes), hereditary bullous epidermolysis, herpes zoster, erythrodermia (including *pityriasis rosea* (Hebra)), lupus miliaris disseminatus faciei, allergic vasculitis-Ruiter and similar diseases thereof (including parapsoriasis acuta), ulcerative chronic pyoderma, sclerema neonatorum, or the like; otolaryngology related diseases such as acute or chronic otitis media, secretory otitis media or stenosis of eustachian tube, Meniere disease and Meniere syndrome, acute sensorineural hearing loss, vasomotor (nervous) rhinitis, allergic rhinitis, pollinosis (hay fever), progressive gangrenous rhinitis, laryngitis or laryngeal edema, after-treatment after surgery in the field of otorhinolaryngology, olfactory disturbance, acute or chronic (repetitive) sialadenitis, or the like; oral surgery related diseases such as intractable stomatitis and glossitis, or the like; glaucoma; rheumatic diseases such as rheumatic fever (including rheumatic carditis), polymyalgia rheumatica, spondylarthritis ankylopoietica (rheumatoid spondylitis), or the like, further, and the following inflammatory diseases, or the like.

The "inflammatory diseases" referred to in the present invention is not particularly limited as long as it is a disease associated with inflammation.

For example, there may be mentioned inflammatory bone or joint diseases, ocular inflammatory diseases, asthma, bronchitis, rhinitis, dermatitis, inflammatory bowel disease or the like, preferably mentioned inflammatory bone or joint diseases and/or ocular inflammatory diseases.

Here, the "inflammatory bone or joint disease" is not particularly limited as long as it is a disease accompanied by inflammation at the joint portion, and examples thereof include, for example, rheumatoid arthritis, juvenile rheumatoid arthritis (including Still's disease), osteoarthritis, osteoporosis, spondylarthritis, or the like, preferably rheumatoid arthritis and/or osteoarthritis.

In addition, the "ocular inflammatory diseases" is not particularly limited as long as it is a disease accompanied by inflammation at eye part, and examples thereof include anterior eye inflammatory diseases and posterior eye inflammatory diseases.

The anterior eye inflammatory diseases include, for example, keratitis, keratoconjunctivitis, conjunctivitis, blepharitis, dry eye syndrome (hereinafter also referred to as "dry eye".), allergic conjunctivitis, uveitis, inflammation after anterior eye surgery, inflammation due to rejection of ocular tissue transplantation, or the like, preferably keratitis, keratoconjunctivitis, conjunctivitis, blepharitis, dry eye syndrome (dry eye), allergic conjunctivitis, uveitis, and inflammation after anterior eye surgery, particularly preferably keratitis, keratoconjunctivitis, conjunctivitis, dry eye syndrome (dry eye), and allergic conjunctivitis.

The posterior eye inflammatory diseases include age-related macular degeneration, diabetic retinopathy, diabetic macular edema, neovascular maculopathy, paroxysm epimacular membrane, proliferative vitreoretinopathy, pigmentary degeneration of the retina, central retinal vein occlusion, central retinal artery occlusion, branch retinal vein occlusion, branch retinal artery occlusion, inflammation or degeneration of posterior eye caused by retinal detachment or external injuries (including surgery of posterior eye), retinitis, uveitis, scleritis, optic neuritis, or the like, preferably retinal diseases such as age-related macular degeneration, diabetic retinopathy, diabetic macular edema, neovascular maculopathy, proliferative vitreoretinopathy, central retinal vein occlusion, central retinal artery occlusion, branch retinal vein occlusion, branch retinal artery occlusion, inflammation or degeneration caused by external injuries (including surgery of posterior eye), retinitis, uveitis, scleritis, optic neuritis, or the like, and particularly preferably age-related macular degeneration, diabetic macular edema, central retinal vein occlusion, and branch retinal vein occlusion.

The "theraputic agent" referred to in the present invention means a medicine to be used for treating diseases. Also, the "prophylactic agent" referred to in the present invention means a medicine to be used for the prophylaxis of diseases.
(A) Preferred examples of the present compound include compounds in which the respective groups are groups as defined below and salts thereof in the compounds represented by the general formula (1) and salts thereof.

(1)

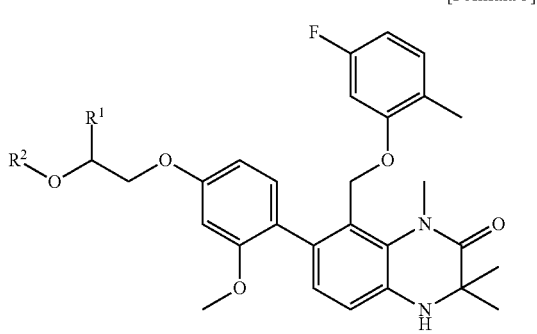

The compound or a salt thereof wherein, in the general formula (1),
(a1) R¹ represents a hydrogen atom, a lower alkyl group, a carboxyl group, an ester of a carboxyl group, an amide of a carboxyl group or a cyano group;
in the case where R¹ is a lower alkyl group, the lower alkyl group may have one or a plurality of groups selected from a halogen atom, a lower cycloalkyl group, an aryl group, a heterocyclic group, a hydroxyl group, an ester of a hydroxyl group, a lower alkoxyl group, a lower alkoxyl group substituted by a halogen atom(s), a lower cycloalkyloxy group, an aryloxy group, a heterocyclicoxy group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkylcarbonyl group, an arylcarbonyl group, a heterocyclic carbonyl group, a carboxyl group, an ester of a carboxyl group, an amide of a carboxyl group and a cyano group as a substituent(s); and/or,
(a2) R² represents a hydrogen atom, a lower alkylcarbonyl group, a lower cycloalkylcarbonyl group, an arylcarbonyl group, a heterocyclic carbonyl group, a carboxyl group, an ester of a carboxyl group, an amide of a carboxyl group, a phosphate group or an ester of a phosphate group;
in the case where R² is a lower alkylcarbonyl group, a lower cycloalkylcarbonyl group, an arylcarbonyl group or a heterocyclic carbonyl group, the lower alkylcarbonyl group, the lower cycloalkylcarbonyl group, the arylcarbonyl group or the heterocyclic carbonyl group may have one or a plurality of groups selected from a halogen atom, a lower cycloalkyl group, an aryl group, a heterocyclic group, a hydroxyl group, an ester of a hydroxyl group, a lower alkoxyl group, a lower alkoxyl group substituted by a halogen atom(s), a lower cycloalkyloxy group, an aryloxy group, a heterocyclicoxy group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkylcarbonyl group, an arylcarbonyl group, a heterocyclic carbonyl group, a carboxyl group, an ester of a carboxyl group, an amide of a carboxyl group and a cyano group as a substituent(s).
That is, in the compound represented by the formula (1), a compound or a salt thereof comprising the respective combination of the above-mentioned (a1) and (a2).
(B) More preferred examples of the present compound include compounds in which the respective groups are groups as defined below and salts thereof in the compounds represented by the general formula (1) and salts thereof.
The compound or a salt thereof wherein, in the general formula (1),
(b1) R¹ represents a hydrogen atom, a lower alkyl group, a carboxyl group or an ester of a carboxyl group;
in the case where R¹ is a lower alkyl group, the lower alkyl group may have one or a plurality of groups selected from a halogen atom, a hydroxyl group, a lower alkoxyl group, a lower alkylcarbonyl group, a carboxyl group, an ester of a carboxyl group, an amide of a carboxyl group and a cyano group as a substituent(s); and/or,
(b2) R² represents a hydrogen atom, a lower alkylcarbonyl group, a heterocyclic carbonyl group, a phosphate group or an ester of a phosphate group; and
in the case where R² is a lower alkylcarbonyl group, the lower alkylcarbonyl group may have one or a plurality of groups selected from a halogen atom, a hydroxyl group, an ester of a hydroxyl group, a lower alkoxyl group, a lower alkoxyl group substituted by a halogen atom(s), an amino group, a lower alkylamino group, a lower alkylcarbonyl group, a carboxyl group, an ester of a carboxyl group, an amide of a carboxyl group and a cyano group as a substituent(s).
That is, in the compound represented by the formula (1), a compound or a salt thereof comprising the respective combination of the above-mentioned (b1) and (b2).
(C) Further preferred examples of the present compound include compounds in which the respective groups are groups as defined below, and salts thereof in the compounds represented by the general formula (1) or salts thereof.
The compound or a salt thereof wherein, in the general formula (1),
(c1) R¹ represents a hydrogen atom, a lower alkyl group or an ester of a carboxyl group;
in the case where R¹ is a lower alkyl group, the lower alkyl group may have one or a plurality of groups selected from a halogen atom, a hydroxyl group, a carboxyl group, an ester of a carboxyl group, an amide of a carboxyl group and a cyano group as a substituent(s); and/or
(c2) R² represents a hydrogen atom, a lower alkylcarbonyl group, a heterocyclic carbonyl group or a phosphate group;
in the case where R² is a lower alkylcarbonyl group, the lower alkylcarbonyl group may have one or a plurality of groups selected from a hydroxyl group, an amino group, a lower alkylamino group and a carboxyl group as a substituent(s).
That is, in the compound represented by the formula (1), a compound or a salt thereof comprising the respective combination of the above-mentioned (c1) and (c2).
(D) Further preferred examples of the present compound include compounds in which the respective groups are groups as defined below, and salts thereof in the compounds represented by the general formula (1) or salts thereof.
The compound or a salt thereof wherein, in the general formula (1),
(d1) R¹ represents a lower alkyl group; the lower alkyl group may have one or a plurality of hydroxyl groups as a substituent(s); and/or,
(d2) R² represents a hydrogen atom or a lower alkylcarbonyl group;
in the case where R² is a lower alkylcarbonyl group, the lower alkylcarbonyl group may have one or a plurality of lower alkylamino groups as a substituent(s).
That is, in the compound represented by the formula (1), a compound or a salt thereof comprising the respective combination of the above-mentioned (d1) and (d2).
(E) Further preferred examples of the present compound include compounds in which the respective groups are groups as defined below, and salts thereof in the compounds represented by the general formula (1) or salts thereof.

The compound or a salt thereof wherein, in the general formula (1), (e1) $R^1$ represents methyl or 1-hydroxyethyl; and/or,
(e2) $R^2$ represents a hydrogen atom or dimethylaminomethylcarbonyl.

That is, in the compound represented by the formula (1), a compound or a salt thereof comprising the respective combination of the above-mentioned (e1) and (e2).

(F) Particularly preferred specific examples of the present compound include the following compounds and salts thereof.

(S)-8-(5-fluoro-2-methylphenoxymethyl)-7-[4-(2-hydroxypropyl)oxy-2-methoxy-phenyl]-1,3,3-trimethyl-3,4-dihydro-1H-quinoxalin-2-one,
8-(5-fluoro-2-methylphenoxymethyl)-7-[4-(2-hydroxy-3,3,3-trifluoropropyl)oxy-2-methoxyphenyl]-1,3,3-trimethyl-3,4-dihydro-1H-quinoxalin-2-one,
(R)-8-(5-fluoro-2-methylphenoxymethyl)-7-[4-(2-hydroxypropyl)oxy-2-methoxy-phenyl]-1,3,3-trimethyl-3,4-dihydro-1H-quinoxalin-2-one,
(R)-8-(5-fluoro-2-methylphenoxymethyl)-7-[4-(2-hydroxybutyl)oxy-2-methoxy-phenyl]-1,3,3-trimethyl-3,4-dihydro-1H-quinoxalin-2-one,
(S)-8-(5-fluoro-2-methylphenoxymethyl)-7-[4-(2-hydroxybutyl)oxy-2-methoxy-phenyl]-1,3,3-trimethyl-3,4-dihydro-1H-quinoxalin-2-one,
(R)-7-[4-(2-ethoxycarbonyl-2-hydroxyethyl)oxy-2-methoxyphenyl]-8-(5-fluoro-2-methylphenoxymethyl)-1,3,3-trimethyl-3,4-dihydro-1H-quinoxalin-2-one,
(S)-7-[4-(2,4-dihydroxybutyl)oxy-2-methoxyphenyl]-8-(5-fluoro-2-methyl-phenoxymethyl)-1,3,3-trimethyl-3,4-dihydro-1H-quinoxalin-2-one,
(R)-7-[4-(2,4-dihydroxybutyl)oxy-2-methoxyphenyl]-8-(5-fluoro-2-methyl-phenoxymethyl)-1,3,3-trimethyl-3,4-dihydro-1H-quinoxalin-2-one,
(S)-8-(5-fluoro-2-methylphenoxymethyl)-7-[4-(2-hydroxyacetoxypropyl)oxy-2-methoxyphenyl]-1,3,3-trimethyl-3,4-dihydro-1H-quinoxalin-2-one,
8-(5-fluoro-2-methylphenoxymethyl)-7-[4-(2-hydroxyethyl)oxy-2-methoxyphenyl]-1,3,3-trimethyl-3,4-dihydro-1H-quinoxalin-2-one,
7-[4-(2,3-dihydroxypropyl)oxy-2-methoxyphenyl]-8-(5-fluoro-2-methylphenoxy-methyl)-1,3,3-trimethyl-3,4-dihydro-1H-quinoxalin-2-one,
(S)-7-[4-(2,3-dihydroxypropyl)oxy-2-methoxyphenyl]-8-(5-fluoro-2-methyl-phenoxymethyl)-1,3,3-trimethyl-3,4-dihydro-1H-quinoxalin-2-one,
(R)-7-[4-(2,3-dihydroxypropyl)oxy-2-methoxyphenyl]-8-(5-fluoro-2-methyl-phenoxymethyl)-1,3,3-trimethyl-3,4-dihydro-1H-quinoxalin-2-one,
(R)-7-[4-(3-cyano-2-hydroxypropyl)oxy-2-methoxyphenyl]-8-(5-fluoro-2-methylphenoxymethyl)-1,3,3-trimethyl-3,4-dihydro-1H-quinoxalin-2-one,
(S)-7-[4-(3-cyano-2-hydroxypropyl)oxy-2-methoxyphenyl]-8-(5-fluoro-2-methylphenoxymethyl)-1,3,3-trimethyl-3,4-dihydro-1H-quinoxalin-2-one,
7-[4-(3-fluoro-2-hydroxypropyl)oxy-2-methoxyphenyl]-8-(5-fluoro-2-methylphenoxymethyl)-1,3,3-trimethyl-3,4-dihydro-1H-quinoxalin-2-one,
7-[4-(3-ethoxycarbonyl-2-hydroxypropyl)oxy-2-methoxyphenyl]-8-(5-fluoro-2-methylphenoxymethyl)-1,3,3-trimethyl-3,4-dihydro-1H-quinoxalin-2-one,
7-[4-(3-t-butoxycarbonyl-2-hydroxypropyl)oxy-2-methoxyphenyl]-8-(5-fluoro-2-methylphenoxymethyl)-1,3,3-trimethyl-3,4-dihydro-1H-quinoxalin-2-one,
7-[4-(3,3-dimethyl-2-hydroxybutyl)oxy-2-methoxyphenyl]-8-(5-fluoro-2-methylphenoxymethyl)-1,3,3-trimethyl-3,4-dihydro-1H-quinoxalin-2-one,
7-[4-(3-carboxy-2-hydroxypropyl)oxy-2-methoxyphenyl]-8-(5-fluoro-2-methylphenoxymethyl)-1,3,3-trimethyl-3,4-dihydro-1H-quinoxalin-2-one,
8-(5-fluoro-2-methylphenoxymethyl)-7-[4-[3-(N-pyrrolidylcarbonyl)-2-hydroxy-propyl]oxy-2-methoxyphenyl]-1,3,3-trimethyl-3,4-dihydro-1H-quinoxalin-2-one,
8-(5-fluoro-2-methylphenoxymethyl)-7-[4-[3-(N-morpholino)carbonyl-2-hydroxy-propyl]oxy-2-methoxyphenyl]-1,3,3-trimethyl-3,4-dihydro-1H-quinoxalin-2-one,
8-(5-fluoro-2-methylphenoxymethyl)-7-[4-[3-(N-piperidino)carbonyl-2-hydroxy-propyl]oxy-2-methoxyphenyl]-1,3,3-trimethyl-3,4-dihydro-1H-quinoxalin-2-one,
(S)-7-[4-[2-(N,N-dimethylaminoacetoxy)propyl]oxy-2-methoxyphenyl]-8-(5-fluoro-2-methylphenoxymethyl)-1,3,3-trimethyl-3,4-dihydro-1H-quinoxalin-2-one,
8-(5-fluoro-2-methylphenoxymethyl)-7-[4-[(2S)-[(2S)-pyrrolidylcarbonyloxy]-propyl]oxy-2-methoxyphenyl]-1,3,3-trimethyl-3,4-dihydro-1H-quinoxalin-2-one,
(R)-7-[4-[2-(N,N-dimethylaminoacetoxy)propyl]oxy-2-methoxyphenyl]-8-(5-fluoro-2-methylphenoxymethyl)-1,3,3-trimethyl-3,4-dihydro-1H-quinoxalin-2-one,
(S)-7-[4-(2-aminoacetoxypropyl)oxy-2-methoxyphenyl]-8-(5-fluoro-2-methyl-phenoxymethyl)-1,3,3-trimethyl-3,4-dihydro-1H-quinoxalin-2-one,
7-[4-[(2S)-[(2S)-amino-3-methylbutanoyloxy]propyl]oxy-2-methoxyphenyl]-8-(5-fluoro-2-methylphenoxymethyl)-1,3,3-trimethyl-3,4-dihydro-1H-quinoxalin-2-one,
(S)-7-[4-[2-(3-carboxypropanoyloxy)propyl]oxy-2-methoxyphenyl]-8-(5-fluoro-2-methylphenoxymethyl)-1,3,3-trimethyl-3,4-dihydro-1H-quinoxalin-2-one,
(S)-7-[4-[2-(2,3-dihydroxypropanoyl)oxypropyl]oxy-2-methoxyphenyl]-8-(5-fluoro-2-methylphenoxymethyl)-1,3,3-trimethyl-3,4-dihydro-1H-quinoxalin-2-one,
7-[4-[(2S)-[(2S)-amino-3-hydroxypropanoyloxy]propyl]oxy-2-methoxyphenyl]-8-(5-fluoro-2-methylphenoxymethyl)-1,3,3-trimethyl-3,4-dihydro-1H-quinoxalin-2-one,
(S)-8-(5-fluoro-2-methylphenoxymethyl)-7-[4-(2-phosphonohydroxypropyl)oxy-2-methoxyphenyl]-1,3,3-trimethyl-3,4-dihydro-1H-quinoxalin-2-one,
(S)-8-(5-fluoro-2-methylphenoxymethyl)-7-[4-(2-phosphonohydroxybutyl)oxy-2-methoxyphenyl]-1,3,3-trimethyl-3,4-dihydro-1H-quinoxalin-2-one,
(S)-7-[4-(3-cyano-2-phosphonohydroxypropyl)oxy-2-methoxyphenyl]-8-(5-fluoro-2-methylphenoxymethyl)-1,3,3-trimethyl-3,4-dihydro-1H-quinoxalin-2-one.

The producing method of the present compound can be roughly classified by the methods shown below, and the method can be optionally selected depending on the kind of the substituents. In addition, with regard to the respective specific producing methods, these are explained in detail in the item of Production Examples in Examples mentioned later. These examples are intended to make the present invention more clearly understandable, and do not limit the scope of the present invention. "PG" used in the following Synthetic Routes means a protective group and "LG" a leaving group.

The present compound (I)-(a) (the compound that $R^2$ is a hydrogen atom in the general formula (1).) can be produced according to Synthetic Route 1. Namely, the present compound (I)-(a) can be given by the reaction of the compound (A) (produced with reference to the above-mentioned Patent Document 2.) with the compound (II) or the compound (III) in an organic solvent such as ethanol and N,N-dimethylformamide (hereinafter also referred to as "DMF".) in the presence of a base such as potassium carbonate and cesium carbonate at 0° C. to 120° C. for 1 hour to 24 hours. Or else, the compound (VI) can be given by the reaction of the compound (A) and the compound (IV) under the same conditions as mentioned above, or of the compound (A) with the compound (V) in an organic solvent such as tetrahydrofuran (hereinafter also referred to as "THF".) and methylene chloride in the presence of tributylphosphine and 1,1'-(azodicarbonyl)dipiperidine at 0° C. to 80° C. for 1 hour to 24 hours. The present compound (I)-(a) can be given by the reaction of the obtained compound (VI) under general deprotection conditions of a hydroxyl group, i.e., in an organic solvent such as methanol in the presence of an acid or a base, or under catalytic hydrogenation conditions at 0° C. to 100° C. for 1 hour to 24 hours.

Synthetic Route 1

[Formula 4]

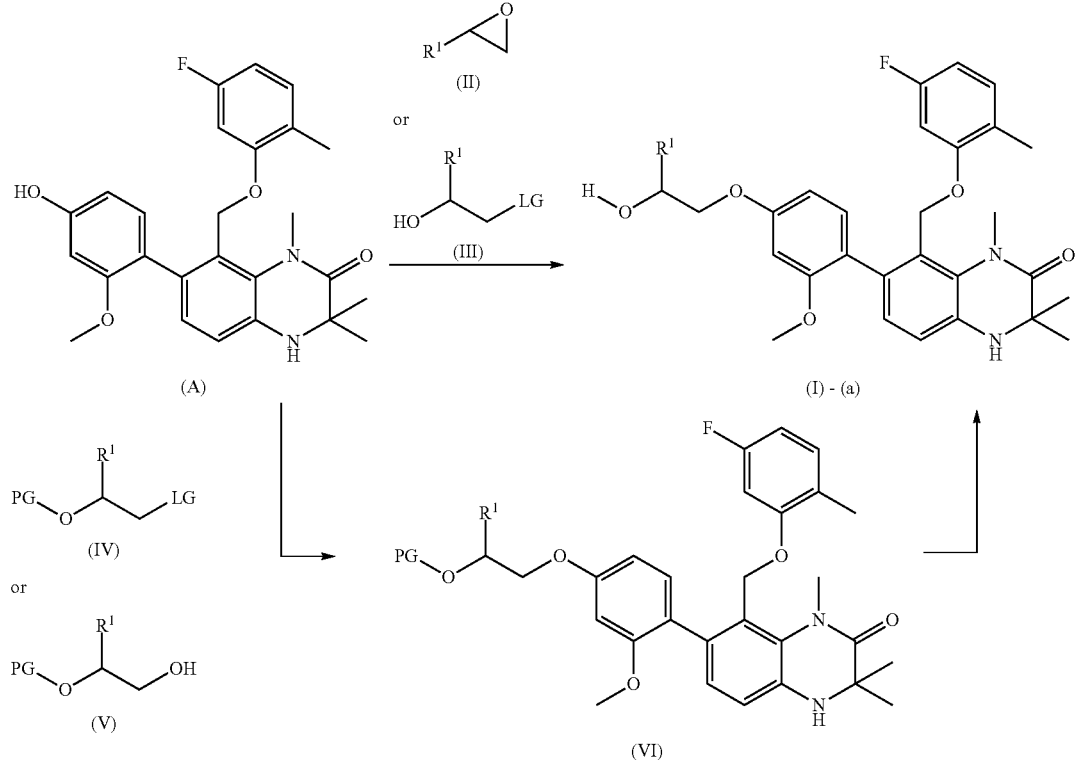

Also, the present compound (I)-(a) (the compound in which $R^2$ is a hydrogen atom in the general formula (1).) can be produced according to Synthetic Route 2. Namely, the compound (VIII) can be given by the reaction of the compound (A) and the compound (VII) in an organic solvent such as ethanol and DMF in the presence of a base such as potassium carbonate and cesium carbonate at 0° C. to 120° C. for 1 hour to 24 hours. Further, the present compound (I)-(a) can be given by the reaction of the obtained compound (VIII) and a reducing agent such as sodium borohydride and lithium aluminum hydride in an organic solvent such as methanol and methylene chloride at 0° C. to 50° C. for 30 minutes to 24 hours.

Synthetic Route 2

[Formula 5]

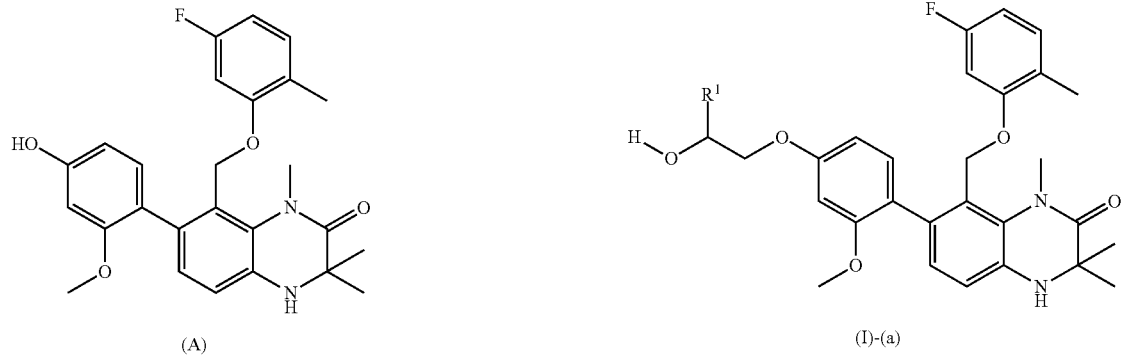

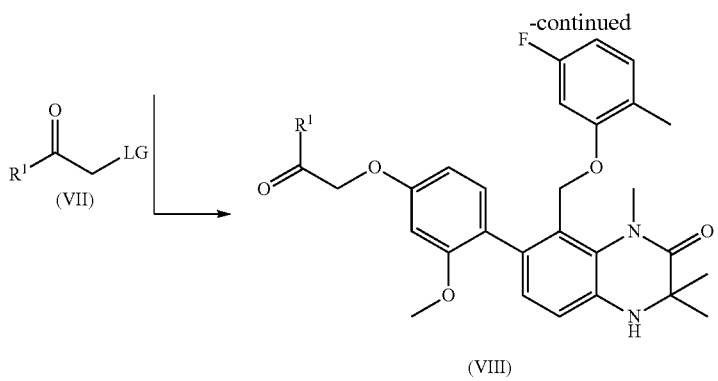

(VII) → (VIII)

The present compound (I)-(b) (the compound that $R^1$ is a lower alkyl group which may have a substituent(s), and $R^2$ is a hydrogen atom in the general formula (1).) can be produced according to Synthetic Route 3. Namely, the compound (X) can be given by the reaction of the compound (A) and the compound (IX) in an organic solvent such as ethanol and DMF in the presence of a base such as potassium carbonate and cesium carbonate at 0° C. to 120° C. for 1 hour to 24 hours. Further, the present compound (I)-(b) can be given by the reaction of can be given by the reaction of the obtained compound (X) and a nucleophilic reagent in an organic solvent such as DMF and methylene chloride at 0° C. to 100° C. for 1 hour to 24 hours.

Synthetic Route 3

[Formula 6]

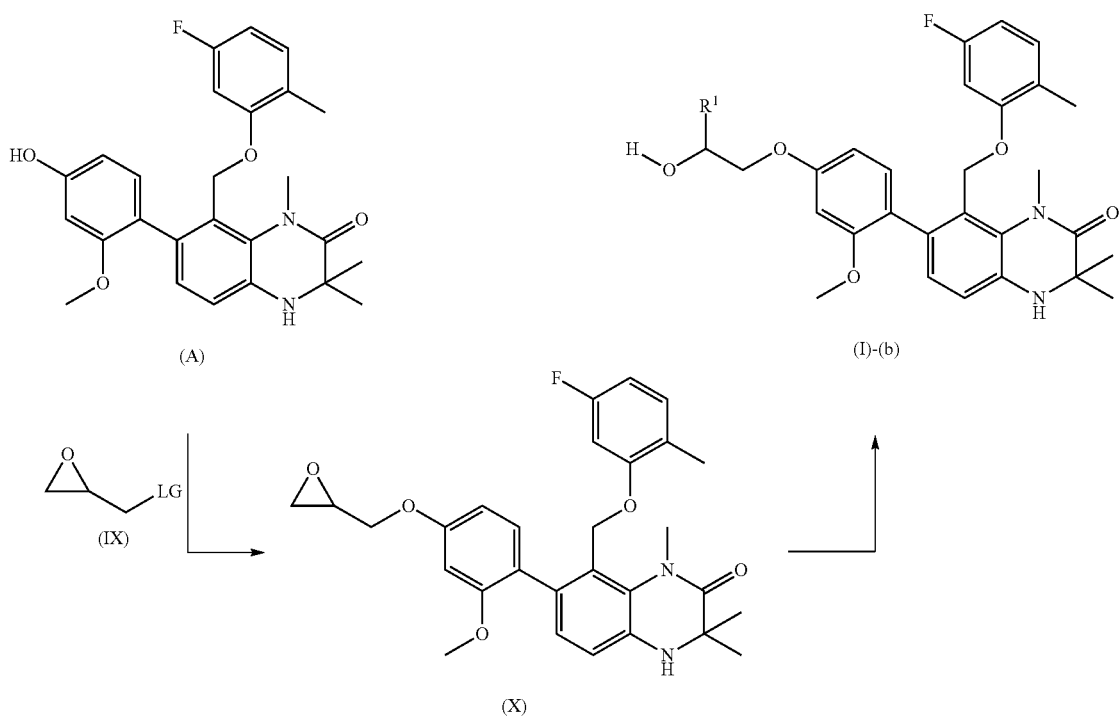

The present compound (I)-(c) (the compound that $R^1$ is a lower alkyl group having a hydroxyl group, and $R^2$ is a hydrogen atom in the general formula (1). Also, n in Synthetic Route 4 represents an integer of 1 or more.) can be produced according to Synthetic Route 4. Namely, the present compound (I)-(c) can be given by the reaction of can be given by the reaction of the compound (XIII)-(a) or the compound (XIII)-(b) which can be given by the reaction of the compound (A) with the compound (XI) or the compound (XII) in an organic solvent such as ethanol and DMF in the presence of a base such as potassium carbonate and cesium carbonate at 0° C. to 120° C. for 1 hour to 24 hours, under general deprotection conditions of a hydroxyl group, i.e., in an organic solvent such as methanol in the presence of an acid or a base, or under catalytic hydrogenation conditions at 0° C. to 100° C. for 1 hour to 24 hours.

Synthetic Route 4

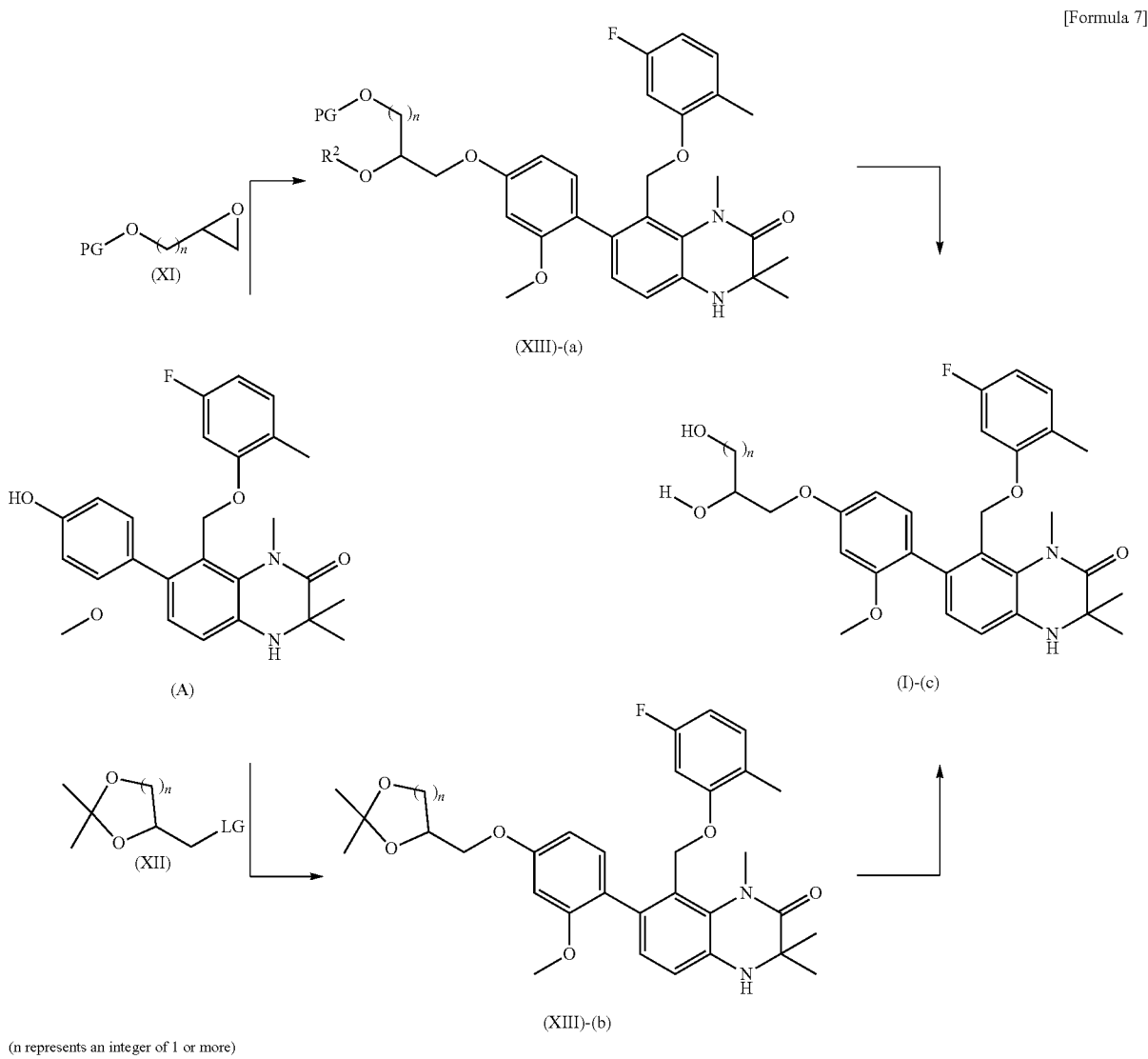

(n represents an integer of 1 or more)

The compound (XI) (n represents an integer of 1 or more) can be produced according to Synthetic Route 5. Namely, the compound (XV) (the compound that LG is a mesyl group or a tosyl group) can be given by the reaction of the compound (XIV) with methanesulfonyl chloride, or p-toluenesulfonyl chloride in an organic solvent such as methylene chloride in the presence of a base such as pyridine and 2,6-lutidine, etc. at −40° C. to room temperature for 30 minutes to 24 hours. Further, the compound (XI) can be given by the reaction of the obtained compound (XV) in an organic solvent such as methanol in the presence of a base such as potassium carbonate at room temperature to 80° C. for 30 minutes to 6 hours.

Synthetic Route 5

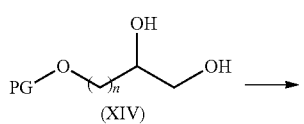

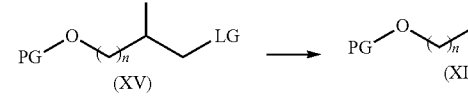

The present compound (I)-(d) (the compound that $R^1$ is —$CH_2COOR^m$, and $R^2$ is a hydrogen atom in the general formula (1). $R^m$ represents a lower alkyl group.), the present compound (I)-(e) (the compound that $R^1$ is —$CH_2COOH$, and $R^2$ is a hydrogen atom in the general formula (1).) and the present compound (I)-(f) (the compound that $R^1$ is —$CH_2$—$R^n$, and $R^2$ is a hydrogen atom in the general formula (1). $R^n$ represents an ester of a carboxyl group —$COOR^f$ or an amide of a carboxyl group —$CONR^gR^h$. $R^f$, $R^g$ and $R^h$ are the same as mentioned above.) can be produced according to Synthetic Route 6. Namely, the compound (XVII) can be given by the reaction of the compound (A) with methyl bromoacetate (XVI) in an organic solvent such as acetonitrile and DMF in the presence of a base such as potassium carbonate and cesium carbonate at 0° C. to 120° C. for 1 hour to 24 hours. Further, the present compound (I)-(d) can be given by the reaction of the obtained compound (XVII) with an acetic acid ester (XVIII) (R'" are the same as mentioned above.) in an organic solvent such as diethyl ether and THF in the presence of a base such as sodium hydride and lithium diisopropylamide at −80° C. to 0° C. for 15 minutes to 8 hours, and then, by the reaction with a reducing agent such as sodium borohydride and lithium aluminum hydride in an organic solvent such as methanol and methylene chloride at 0° C. to 50° C. for 30 minutes to 24 hours.

In addition, the present compound (I)-(e) can be given by the reaction of the compound (I)-(d) in an organic solvent such as methanol and ethanol in the presence of a base such as sodium hydroxide at 0° C. to 80° C. for 30 minutes to 24 hours.

Further, the present compound (I)-(f) can be given by the reaction of the compound (I)-(e) with an alcohol (XIX) or an amine (XX) in an organic solvent such as THF and DMF in the presence of a condensing agent such as 1-ethyl-3-(3-dimethylaminopropyl)carbodiimide hydrochloride (hereinafter also referred to as "EDC") and O-(7-azabenzotriazol-1-yl)-N,N,N'N'-tetramethyluronium hexafluorophosphate (hereinafter also referred to as "HATU") and a base such as 4-dimethylaminopyridine and triethylamine at 0° C. to 80° C. for 1 hour to 24 hours.

Synthetic Route 6

[Formula 9]

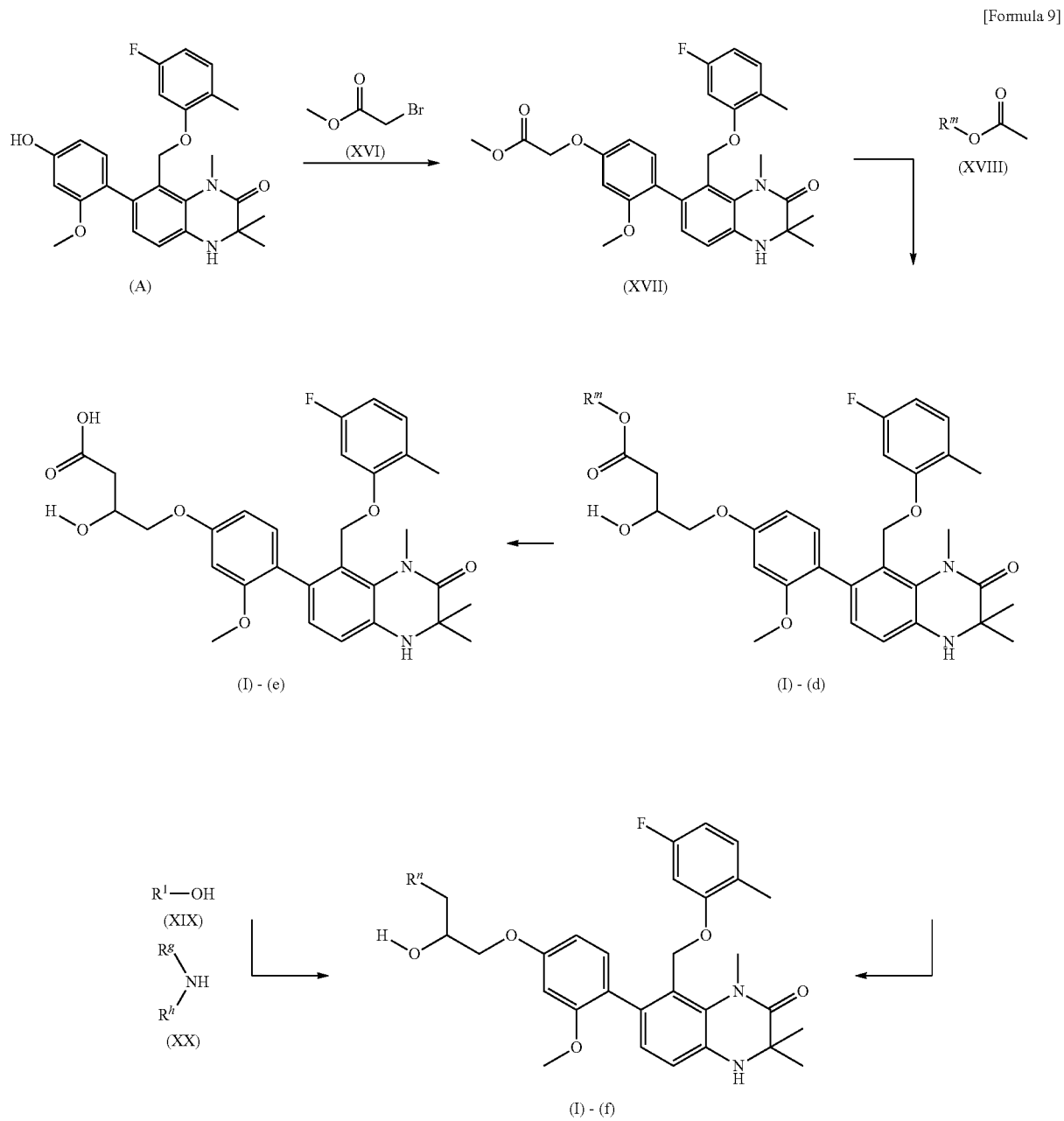

The present compound (I)-(g) (the compound that $R^2$ is a lower alkylcarbonyl group which may have a substituent(s), a lower cycloalkylcarbonyl group which may have a substituent(s), an arylcarbonyl group which may have a substituent(s) or a heterocyclic carbonyl group which may have a substituent(s) in the general formula (1).) can be produced according to Synthetic Route 7. Namely, the present compound (I)-(g) can be given by the reaction of the present compound (I)-(a) with carboxylic acid (XXI) in an organic solvent such as THF and DMF in the presence of a condensing agent such as EDC and HATU, and a base such as 4-dimethylaminopyridine and triethylamine at 0° C. to 80° C. for 1 hour to 24 hours, or of the present compound (I)-(a) with an acid anhydride (XXII) in an organic solvent such as THF and pyridine in the presence of a base such as 4-dimethylaminopyridine at 0° C. to 80° C. for 1 hour to 24 hours.

Synthetic Route 7

[Formula 10]

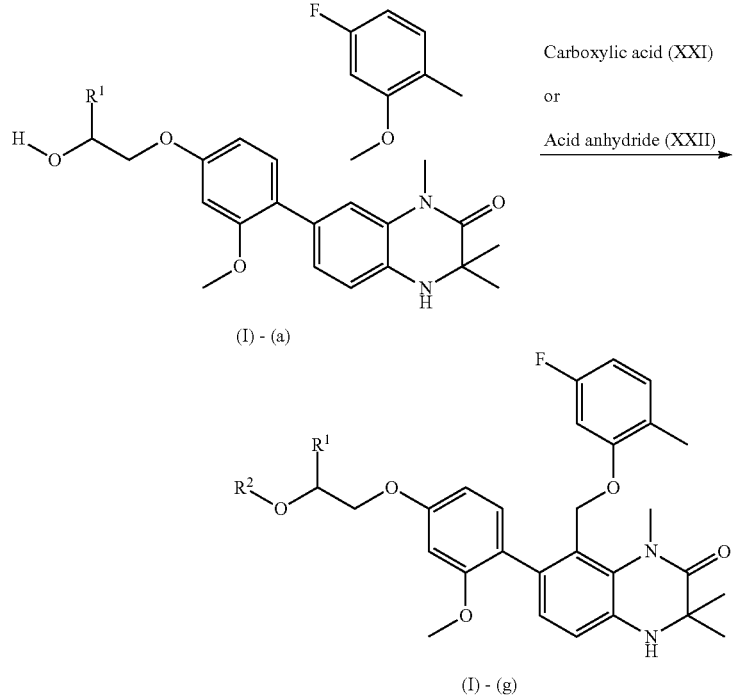

The present compound (I)-(h) (the compound that $R^2$ is a phosphate group in the general formula (1).) can be produced according to Synthetic Route 8. Namely, the present compound (I)-(i) (the compound that $R^2$ is an ester of a phosphate group —PO(OR)$_2$ in the general formula (1).) can be given by the reaction of the present compound (I)-(a) with dialkoxy(diisopropylamino)phosphine (XXIII) ($R'$ represents a lower alkyl group.) in an organic solvent such as DMF in the presence of 1H-tetrazole and m-chlorobenzoic acid at 0° C. to 50° C. for 10 minutes to 3 hours. Further, the present compound (I)-(h) can be given by the reaction of the obtained present compound (I)-(i) with trifluoroacetic acid in an organic solvent such as methylene chloride at 0° C. to 50° C. for 10 minutes to 3 hours.

Synthetic Route 8

[Formula 11]

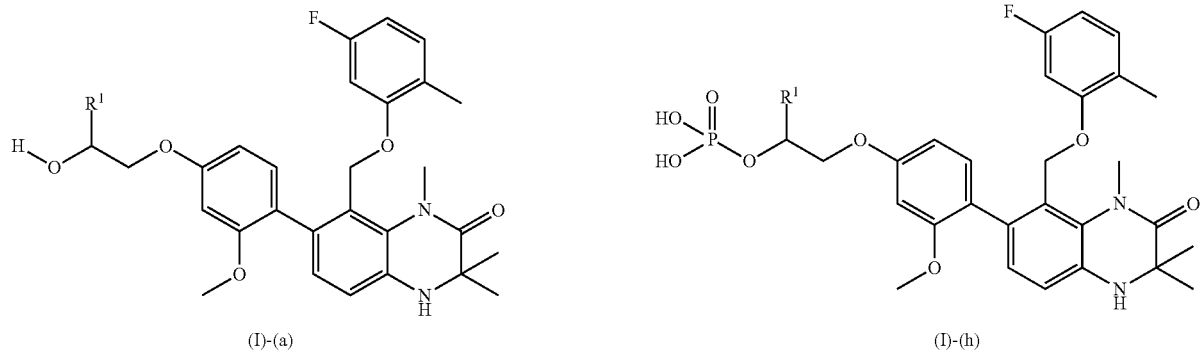

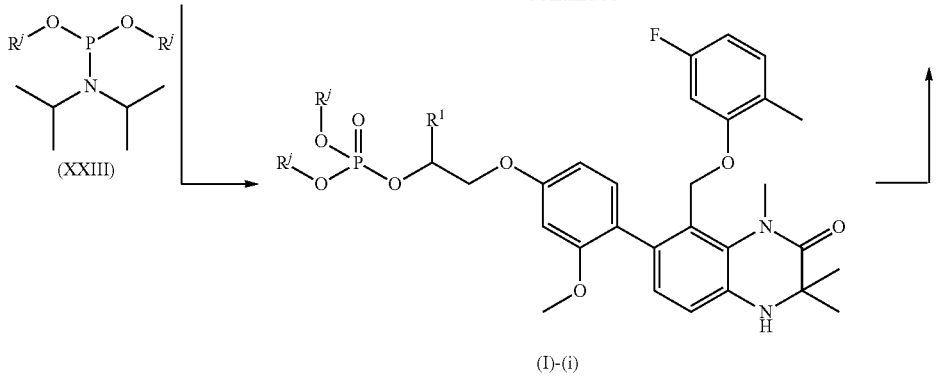

(I)-(i)

The compounds of the present invention produced by the Synthetic Routes described above can be also in the form of a salt, a hydrate or a solvate as described above, using commonly used techniques.

In order to find the usefulness of the present compound as a medicine, Pharmacological Tests mentioned later were carried out. Incidentally, it was confirmed that the present compound is particularly useful as a medicine by carrying out the same assay for the compound conventionally known from the literature and comparing it with the test results of the present compound.

By using the glucocorticoid receptor (hereinafter also referred to as "GR".) competitive assay kit, GR competitive assay by fluorescence polarization was carried out. As a result, the present compounds showed excellent GR binding activity.

Also, an IL-6 production inhibitory action in a human corneal epithelium cell line after stimulation by lipopolysaccharide (hereinafter also referred to as "LPS".) was investigated. As a result, the present compounds showed an excellent IL-6 production inhibitory action, i.e., an action as a GR agonist.

Further, a TNFα production inhibitory action in rat whole blood after stimulation by LPS was investigated. As a result, the present compounds showed an excellent TNFα production inhibitory action, i.e., an action as a GR agonist.

Moreover, an IL-2 production inhibitory action in a normal human CD4+T cell after stimulation by an anti-CD3/CD28 antibody was investigated. As a result, the present compounds showed an excellent IL-2 production inhibitory action, i.e., an action as a GR agonist.

Furthermore, an IL-4 production inhibitory action in a normal human CD4+T cell after stimulation by an anti-CD3/CD28 antibody was investigated. As a result, the present compounds showed an excellent IL-4 production inhibitory action, i.e., an action as a GR agonist.

Also, an MCP-1 production inhibitory action in a human monocyte cell after stimulation by LPS was investigated. As a result, the present compounds showed an excellent MCP-1 production inhibitory action, i.e., an action as a GR agonist.

From the above, the present compounds have a production inhibitory action of a plurality of cytokines, i.e., the above-mentioned IL-6, TNFα, IL-2, IL-4 and MCP-1, so that, in particular, these are useful as a GR agonist, and confirmed that these are useful as a prophylactic or therapeutic agent for diseases to which a GR agonist such as steroids are effective, in particular, for inflammatory diseases (bone and joint diseases, ocular inflammatory diseases, or the like). In addition, the present compounds are further useful as a GR agonist since, for example, these have a production inhibitory action to a number of cytokines as compared with the conventionally known compounds as disclosed in Patent Document 2.

In addition, in order to evaluate the possibility of the present compounds for a treatment agent of anterior eye inflammatory diseases, an inhibitory effect of the present compounds on edema formation in a carrageenin-caused conjunctivitis model of a rat, an inhibitory effect of the present compounds on a number of infiltrated cells into aqueous humor in an anterior chamber tap ocular inflammation model of a rabbit, a treatment effect of the present compounds on corneal disorder in exorbital lachrymal gland-extracted dry eye model of a rat and an inhibitory effect of the present compounds on hyperemia in ovalbumin actively sensitized allergic conjunctivitis model of a rabbit were investigated. As a result, the present compounds showed an edema formation inhibitory effect, a number of infiltrated cells into aqueous humor inhibitory effect, a corneal disorder treatment effect and a hyperemia inhibitory effect.

Accordingly, the present compound is confirmed to be useful as an anterior eye inflammatory diseases treatment agent, in particular, as a prophylactic or therapeutic agent for keratitis, keratoconjunctivitis, conjunctivitis, blepharitis, dry eye syndrome (dry eye), allergic conjunctivitis, uveitis, inflammation after surgery and inflammation due to rejection of ocular tissue transplantation, or the like, more preferably as a prophylactic or therapeutic agent for the ocular inflammatory diseases such as keratitis, keratoconjunc-tivitis, conjunctivitis, dry eye syndrome (dry eye), allergic conjunctivitis, uveitis, inflammation after surgery, or the like.

Further, in order to evaluate the possibility of the present compounds as a treatment agent for posterior eye inflammatory diseases, an inhibitory effect of the present compounds on a leaked amount of the fluorescent dye into a vitreous body in a VEGF-induced retinal elevated vascular permeability model of a rabbit was investigated. As a result, the present compounds showed a retinal elevated vascular permeability inhibitory action.

Accordingly, the present compound is confirmed to be useful as an posterior eye inflammatory diseases treatment agent, in particular, as a prophylactic or therapeutic agent for age-related macular degeneration, diabetic retinopathy, diabetic macular edema, neovascular maculopathy, proliferative vitreoretinopathy, central retinal vein occlusion, central retinal artery occlusion, branch retinal vein occlusion, branch retinal artery occlusion, inflammation or degeneration of posterior eye caused by external injury, retinitis, uveitis, scleritis, optic neuritis, or the like, more preferably as a prophylactic or therapeutic agent for the ocular inflammatory diseases such as age-related macular degeneration, diabetic macular edema, central retinal vein occlusion, branch retinal vein occlusion, or the like.

In addition, during the above-mentioned Pharmacological Test was carried out, no serious adverse side effect due to administration of the present compound was observed, and it was confirmed that it is useful as a prophylactic or therapeutic agent for ocular inflammatory diseases.

A detailed explanation of this matter will be more specifically described in the section of "Pharmacological Test" in Examples described below.

The present compound can be administered either orally or parenterally. The administration form may include oral administration, local administration to eyes (instillation administration, administration into the interior of the conjunctival sac, administration into the vitreous body, subconjunctival administration, subtenon administration, or the like), intravenous administration, intramuscular administration, intraarticular administration, pernasality administration, inhalation administration, percutaneous administration, or the like. It is preferably a parenteral administration form, and may include local administration to eyes (instillation administration, administration into the interior of the conjunctival sac, administration into the vitreous body, subconjunctival administration, subtenon administration, or the like), intravenous administration, intramuscular administration, intraarticular administration, pernasality administration, inhalation administration, percutaneous administration, or the like. It is particularly preferably local administration to eyes (instillation administration, administration into the interior of the conjunctival sac, administration into the vitreous body, subconjunctival administration, subtenon administration, or the like).

Examples of the dosage form of the present compound include a tablet, a capsule, a granule, a powder, an enteric tablet, an injection, an eye drop, a suppository, a percutaneous absorbent, an ointment, aerosols (including an inhalant) and the like. Such a preparation can be prepared using a commonly used technique. A preferable dosage form to be used when it is local administered to eyes may include an ophthalmic agent, in particular, as a prophylactic or therapeutic agent for a dissolution type ophthalmic agent, a suspension type ophthalmic agent, an emulsion type ophthalmic agent or a gel type ophthalmic agent, or the like, an ophthalmic ointment, in particular, a coating agent for the interior of the conjunctival sac or a coating agent for eyelid, or the like, or an injection, in particular, a subconjunctival administration agent, a Tenon capsule administration agent or an administration agent into the vitreous body, or the like.

For example, an oral preparation such as a tablet, a capsule, a granule or a powder can be prepared by optionally adding a necessary amount of an excipient such as lactose, mannitol, starch, crystalline cellulose, light silicic anhydride, calcium carbonate or calcium hydrogen phosphate; a lubricant such as stearic acid, magnesium stearate or talc; a binder such as starch, hydroxypropyl cellulose, hydroxypropylmethyl cellulose or polyvinylpyrrolidone; a disintegrant such as carboxymethyl cellulose, low-substituted hydroxypropylmethyl cellulose or calcium citrate; a coating agent such as hydroxypropylmethyl cellulose, macrogol or a silicone resin; a stabilizer such as ethyl p-hydroxybenzoate or benzyl alcohol; a corrigent such as a sweetener, a sour agent or a flavor, or the like.

A parenteral preparation such as an injection or an eye drop can be prepared by optionally adding a necessary amount of a tonicity agent such as sodium chloride, concentrated glycerin, propylene glycol, polyethylene glycol, potassium chloride, sorbitol or mannitol; a buffer such as sodium phosphate, sodium hydrogen phosphate, sodium acetate, citric acid, glacial acetic acid or trometamol; a surfactant such as Polysorbate 80, polyoxy 40 stearate or polyoxyethylene hydrogenated castor oil 60; a stabilizer such as sodium citrate or sodium edetate; a preservative such as benzalkonium chloride, paraben, benzothonium chloride, p-hydroxybenzoate ester, sodium benzoate or chlorobutanol; a pH adjusting agent such as hydrochloric acid, citric acid, phosphoric acid, glacial acetic acid, sodium hydroxide, sodium carbonate or sodium hydrogen carbonate; a soothing agent such as benzyl alcohol, or the like.

The dose of the present compound can be appropriately selected depending on the symptoms, age, dosage form or the like. For example, in the case of an oral preparation, it can be administered in an amount of generally 0.01 to 1,000 mg, preferably 1 to 100 mg per day in a single dose or several divided doses. Further, in the case of an eye drop, a preparation comprising the present compound at a concentration of generally 0.0001% to 10% (w/v), preferably 0.01% to 5% (w/v) can be administered in a single dose or several divided doses.

Hereinafter, Production Examples of the present compound, Preparation Examples and results of Pharmacological Test will be described. However, these examples are described for the purpose of understanding the present invention better and are not meant to limit the scope of the present invention.

PRODUCTION EXAMPLES

Reference Example 1

(S)-4-benzyloxy-2-hydroxybutyl methanesulfonate (the Reference Compound 1-1)

A methylene chloride (50 mL) solution of methanesulfonyl chloride (4.1 mL, 53.0 mmol) was added dropwise to a methylene chloride (200 mL) solution of (S)-4-benzyloxy-1,2-butanediol (10.0 g, 51.0 mmol) and 2,6-lutidine (59 mL, 507 mmol) at −20° C. over 30 minutes, and the mixture was stirred at room temperature for 24 hours. Further, a methylene chloride (30 mL) solution of methanesulfonyl chloride (1.3 mL, 16.8 mmol) was added dropwise to the above mixture at room temperature over 30 minutes, and the mixture was stirred for 1.5 hours. The mixture was washed with 0.5N hydrochloric acid (200 mL×4), a saturated aqueous sodium hydrogen carbonate solution (100 mL×3), and a saturated saline solution (100 mL). The organic layer was dried over anhydrous magnesium sulfate and filtered. The filtrate was concentrated under reduced pressure and the obtained residue was purified by silica gel column chromatography (chloroform/methanol) to give the titled reference compound (12.3 g) (Yield: 88%).

TABLE 1

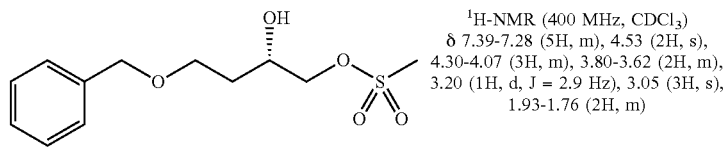

Reference compound 1-1

$^1$H-NMR (400 MHz, CDCl$_3$)
δ 7.39-7.28 (5H, m), 4.53 (2H, s), 4.30-4.07 (3H, m), 3.80-3.62 (2H, m), 3.20 (1H, d, J = 2.9 Hz), 3.05 (3H, s), 1.93-1.76 (2H, m)

Reference Example 2

(S)-4-benzyloxy-1,2-epoxybutane (the Reference Compound 2-1)

A mixture of (S)-4-benzyloxy-2-hydroxybutyl methanesulfonate (the reference compound 1-1, 12.3 g, 44.8 mmol), potassium carbonate (12.3 g, 89.0 mmol) and methanol (100 mL) was stirred at room temperature for 75 minutes. After removing the solvent under reduced pressure, 0.5N sodium hydroxide (450 mL) and ethyl acetate (200 mL) were added to the residue. The mixture was distributed, and the aqueous layer was extracted with ethyl acetate (100 mL×2). The organic layers were combined, and washed with a saturated saline solution (100 mL). The organic layer was dried over anhydrous magnesium sulfate and filtered. The filtrate was concentrated under reduced pressure to give the titled reference compound (8.0 g) (quantitative).

TABLE 2

| Reference compound 2-1 | $^1$H-NMR (400 MHz, CDCl$_3$) δ 7.41-7.27 (5H, m), 4.53 (2H, s), 3.69-3.58 (2H, m), 3.12-3.04 (1H, m), 2.79 (1H, dd, J = 5.1, 4.0 Hz), 2.53 (1H, dd, J = 5.1, 2.7 Hz), 1.98-1.86 (1H, m), 1.84-1.72 (1H, m) |
|---|---|

(R)-4-benzyloxy-1,2-epoxybutane (the Reference Compound 2-2)

Under ice-cooling, p-toluenesulfonyl chloride (1.45 g, 7.6 mmol) was added to a pyridine (25 mL) solution of (R)-4-benzyloxy-1,2-butanediol (1.24 g, 6.3 mmol) and after stirring for 5 hours, the mixture was stirred at room temperature overnight. The mixture was diluted with ethyl acetate (100 mL), and washed with 1N hydrochloric acid (50 mL, 30 mL) and a saturated saline solution (50 mL). The organic layer was dried over anhydrous magnesium sulfate and filtered, and the filtrate was concentrated under reduced pressure. The obtained residue was dissolved in tetrahydrofuran (60 mL), sodium hydride (0.38 g, 9.5 mmol) was added thereto at room temperature, and the resulting mixture was stirred at 50° C. overnight. After allowing to cool at room temperature, water (200 mL) was added to the mixture and the mixture was extracted with ethyl acetate (200 mL), and the organic layer was washed with a saturated saline solution (100 mL). The organic layer was dried over anhydrous magnesium sulfate and filtered, and the filtrate was concentrated under reduced pressure. The obtained residue was purified by silica gel column chromatography (hexane/ethyl acetate) to give the titled reference compound (0.99 g) (Yield: 89%).

TABLE 3

| Reference compound 2-2 | $^1$H-NMR (400 MHz, CDCl$_3$) δ 7.38-7.27 (5H, m), 4.53 (2H, s), 3.69-3.57 (2H, m), 3.12-3.03 (1H, m), 2.79 (1H, dd, J = 4.9, 4.0 Hz), 2.53 (1H, dd, J = 4.9, 2.7 Hz), 1.98-1.87 (1H, m), 1.84-1.73 (1H, m) |
|---|---|

Reference Example 3

(S)-7-[4-(4-benzyloxy-2-hydroxybutyl)oxy-2-methoxyphenyl]-8-(5-fluoro-2-methylphenoxymethyl)-1,3,3-trimethyl-3,4-dihydro-1H-quinoxalin-2-one (the reference compound 3-1)

A mixture of 8-(5-fluoro-2-methylphenoxymethyl)-7-(4-hydroxy-2-methoxyphenyl)-1,3,3-trimethyl-3,4-dihydro-1H-quinoxalin-2-one (the compound A (produced with reference to the above-mentioned Patent Document 2, hereinafter the same), 500 mg, 1.11 mmol), (S)-4-benzyloxy-1,2-epoxybutane (the Reference Compound 2-1, 500 mg, 2.81 mmol), potassium carbonate (600 mg, 4.34 mmol) and ethanol (5 mL) was stirred at 60° C. for 7 hours. To the mixture was added water (30 mL), and the mixture was extracted with ethyl acetate (30 mL×2). The organic layer was washed with a saturated saline solution (30 mL), dried over anhydrous magnesium sulfate and filtered. The filtrate was concentrated under reduced pressure and the obtained residue was purified by silica gel column chromatography (hexane/ethyl acetate) to give the titled reference compound (420 mg) as white amorphous (Yield: 60%).

TABLE 4

| Reference compound 3-1 | $^1$H-NMR (400 MHz, CDCl$_3$) δ 7.39-7.28 (5H, m), 7.21 (1H, dd, J = 6.6, 2.2 Hz), 6.92-6.84 (2H, m), 6.70 (1H, d, J = 7.8 Hz), 6.61-6.54 (2H, m), 6.38 (1H, td, J = 8.3, 2.4 Hz), 6.04 (1H, dd, J = 11.2, 2.4 Hz), 5.21 (1H, d, J = 13.7 Hz), 4.84 (1H, d, J = 13.7 Hz), 4.56 (2H, s), 4.30-4.21 (1H, m), 4.04-3.95 (2H, m), 3.79 (3H, s), 3.79-3.66 (2H, m), 3.46 (3H, s), 3.08 (1H, t, J = 3.0 Hz), 2.01 (3H, s), 1.99-1.92 (2H, m), 1.54-1.50 (1H, m), 1.28 (3H, s), 0.90 (3H, s) |
|---|---|

Reference Example 4

8-(5-fluoro-2-methylphenoxymethyl)-7-[4-(2-tetrahydropyran-2-yloxyethyl)oxy-2-methoxyphenyl]-1,3,3-trimethyl-3,4-dihydro-1H-quinoxalin-2-one (the reference compound 4-1)

A tetrahydrofuran (5 mL) suspension of 8-(5-fluoro-2-methylphenoxymethyl)-7-(4-hydroxy-2-methoxyphenyl)-1,3,3-trimethyl-3,4-dihydro-1H-quinoxalin-2-one (the compound A, 100 mg, 0.22 mmol), 2-(tetrahydropyran-2-yloxy) ethanol (65 μL, 0.48 mmol), tri-n-butylphosphine (115 μL, 0.48 mmol) and 1,1'-(azodicarbonyl)dipiperidine (115 mg, 0.46 mmol) was stirred at room temperature overnight. The mixture was diluted with ethyl acetate (30 mL), and the organic layer was washed with a saturated saline solution (30 mL×2). The organic layer was dried over anhydrous magnesium sulfate, and filtered. The filtrate was concentrated under reduced pressure and the obtained residue was purified by silica gel column chromatography (hexane/ethyl acetate) to give the titled reference compound (150 mg) as a yellow oily product (quantitative).

TABLE 5

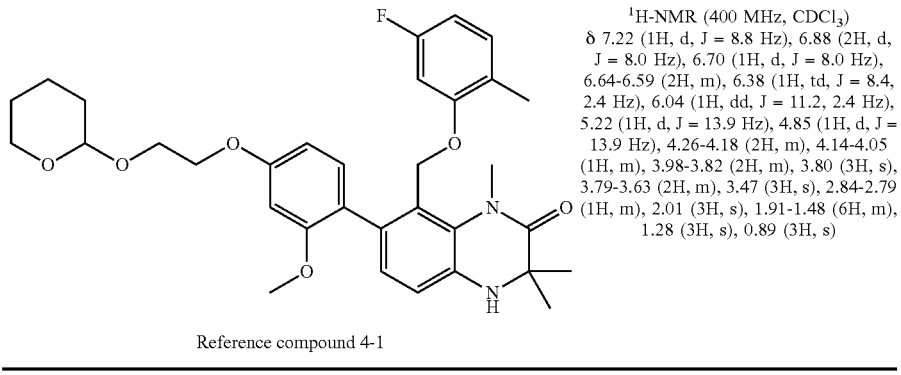

Reference compound 4-1

¹H-NMR (400 MHz, CDCl₃)
δ 7.22 (1H, d, J = 8.8 Hz), 6.88 (2H, d, J = 8.0 Hz), 6.70 (1H, d, J = 8.0 Hz), 6.64-6.59 (2H, m), 6.38 (1H, td, J = 8.4, 2.4 Hz), 6.04 (1H, dd, J = 11.2, 2.4 Hz), 5.22 (1H, d, J = 13.9 Hz), 4.85 (1H, d, J = 13.9 Hz), 4.26-4.18 (2H, m), 4.14-4.05 (1H, m), 3.98-3.82 (2H, m), 3.80 (3H, s), 3.79-3.63 (2H, m), 3.47 (3H, s), 2.84-2.79 (1H, m), 2.01 (3H, s), 1.91-1.48 (6H, m), 1.28 (3H, s), 0.89 (3H, s)

Reference Example 5

7-[4-(2,2-dimethyl-1,3-dioxolan-4-ylmethyl)oxy-2-methoxyphenyl]-8-(5-fluoro-2-methylphenoxymethyl)-1,3,3-trimethyl-3,4-dihydro-1H-quinoxalin-2-one (the reference compound 5-1)

A mixture of 8-(5-fluoro-2-methylphenoxymethyl)-7-(4-hydroxy-2-methoxyphenyl)-1,3,3-trimethyl-3,4-dihydro-1H-quinoxalin-2-one (the compound A, 600 mg, 1.3 mmol), p-toluenesulfonic acid (2,2-dimethyl-1,3-dioxolan-4-yl) methyl ester (572 mg, 2.0 mmol), cesium carbonate (868 mg, 2.7 mmol) and N,N-dimethylformamide (5.0 mL) was stirred at 80° C. overnight. After allowing to cool at room temperature, water (150 mL) was added to the mixture and the mixture was extracted with ethyl acetate (150 mL). The organic layer was washed with a saturated saline solution (150 mL), dried over anhydrous magnesium sulfate and filtered. The filtrate was concentrated under reduced pressure and the obtained residue was purified by silica gel column chromatography (hexane/ethyl acetate) to give the titled reference compound (710 mg) as white amorphous (Yield: 95%).

TABLE 6

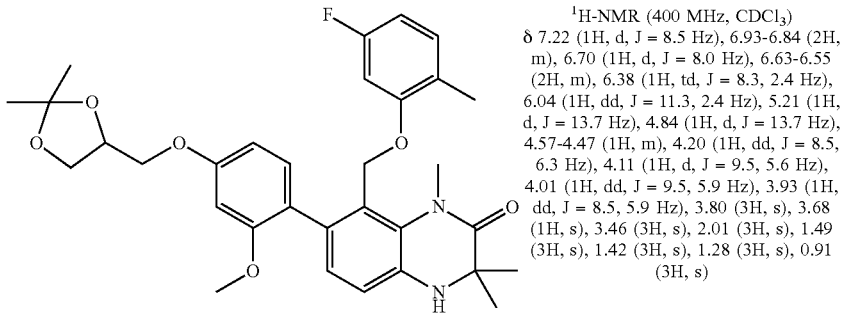

Reference compound 5-1

¹H-NMR (400 MHz, CDCl₃)
δ 7.22 (1H, d, J = 8.5 Hz), 6.93-6.84 (2H, m), 6.70 (1H, d, J = 8.0 Hz), 6.63-6.55 (2H, m), 6.38 (1H, td, J = 8.3, 2.4 Hz), 6.04 (1H, dd, J = 11.3, 2.4 Hz), 5.21 (1H, d, J = 13.7 Hz), 4.84 (1H, d, J = 13.7 Hz), 4.57-4.47 (1H, m), 4.20 (1H, dd, J = 8.5, 6.3 Hz), 4.11 (1H, d, J = 9.5, 5.6 Hz), 4.01 (1H, dd, J = 9.5, 5.9 Hz), 3.93 (1H, dd, J = 8.5, 5.9 Hz), 3.80 (3H, s), 3.68 (1H, s), 3.46 (3H, s), 2.01 (3H, s), 1.49 (3H, s), 1.42 (3H, s), 1.28 (3H, s), 0.91 (3H, s)

Reference compounds 5-2 to 5-6 were obtained by using the compound A and a commercially available compound in accordance with the production process of Reference compound 5-1.

(R)-7-[4-(2,2-dimethyl-1,3-dioxolan-4-ylmethyl)oxy-2-methoxyphenyl]-8-(5-fluoro-2-methylphenoxymethyl)-1,3,3-trimethyl-3,4-dihydro-1H-quinoxalin-2-one (the reference compound 5-2)

TABLE 7

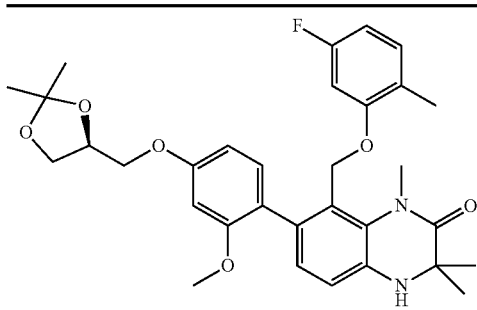

Reference compound 5-2

¹H-NMR (400 MHz, CDCl₃)
δ 7.22 (1H, d, J = 8.3 Hz), 6.92-6.84 (2H, m), 6.70 (1H, d, J = 8.0 Hz), 6.63-6.56 (2H, m), 6.38 (1H, td, J = 8.3, 2.3 Hz), 6.04 (1H, dd, J = 11.3, 2.3 Hz), 5.21 (1H, d, J = 13.4 Hz), 4.84 (1H, d, J = 13.4 Hz), 4.57-4.47 (1H, m), 4.20 (1H, dd, J = 8.7, 6.5 Hz), 4.11 (1H, dd, J = 9.4, 5.7 Hz), 4.01 (1H, dd, J = 9.4, 5.7 Hz), 3.93 (1H, dd, J = 8.4, 5.7 Hz), 3.80 (3H, s), 3.68 (1H, s), 3.46 (3H, s), 2.01 (3H, s), 1.49 (3H, s), 1.42 (3H, s), 1.28 (3H, s), 0.91 (3H, s)

(S)-7-[4-(2,2-dimethyl-1,3-dioxolan-4-ylmethyl)oxy-2-methoxyphenyl]-8-(5-fluoro-2-methylphenoxymethyl)-1,3,3-trimethyl-3,4-dihydro-H-quinoxalin-2-one (the reference compound 5-3)

TABLE 8

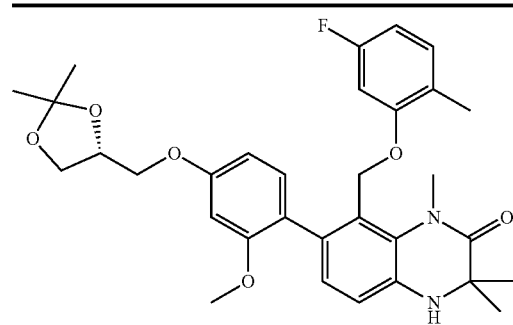

Reference compound 5-3

¹H-NMR (400 MHz, CDCl₃)
δ 7.22 (1H, d, J = 8.5 Hz), 6.93-6.85 (2H, m), 6.70 (1H, d, J = 8.1 Hz), 6.63-6.55 (2H, m), 6.38 (1H, td, J = 8.3, 2.4 Hz), 6.04 (1H, dd, J = 11.2, 2.4 Hz), 5.21 (1H, d, J = 13.7 Hz), 4.84 (1H, d, J = 13.7 Hz), 4.57-4.47 (1H, m), 4.20 (1H, dd, J = 8.5, 6.3 Hz), 4.13-4.09 (1H, m), 4.01 (1H, dd, J = 9.4, 5.7 Hz), 3.93 (1H, dd, J = 8.4, 5.7 Hz), 3.80 (3H, s), 3.68 (1H, s), 3.46 (3H, s), 2.01 (3H, s), 1.49 (3H, s), 1.42 (3H, s), 1.28 (3H, s), 0.91 (3H, s)

(R)-7-[4-(2,3-epoxypropyl)oxy-2-methoxyphenyl]-8-(5-fluoro-2-methylphenoxymethyl)-1,3,3-trimethyl-3,4-dihydro-1H-quinoxalin-2-one (the reference compound 5-4)

TABLE 9

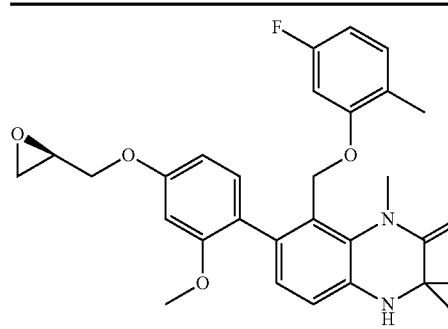

Reference compound 5-4

¹H-NMR (400 MHz, CDCl₃)
δ 7.22 (1H, d, J = 8.0 Hz), 6.93-6.84 (2H, m), 6.70 (1H, d, J = 8.0 Hz), 6.65-6.56 (2H, m), 6.38 (1H, td, J = 8.3, 2.4 Hz), 6.04 (1H, dd, J = 11.2, 2.4 Hz), 5.21 (1H, d, J = 13.7 Hz), 4.84 (1H, d, J = 13.7 Hz), 4.30 (1H, dd, J = 11.1, 3.0 Hz), 4.06-3.97 (1H, m), 3.81 (3H, s), 3.68 (1H, s), 3.46 (3H, s), 3.42-3.36 (1H, m), 2.94 (1H, t, J = 4.5 Hz), 2.83-2.76 (1H, m), 2.01 (3H, s), 1.28 (3H, s), 0.91 (3H, s)

(S)-7-[4-(2,3-epoxypropyl)oxy-2-methoxyphenyl]-8-(5-fluoro-2-methylphenoxymethyl)-1,3,3-trimethyl-3,4-dihydro-1H-quinoxalin-2-one (the reference compound 5-5)

TABLE 10

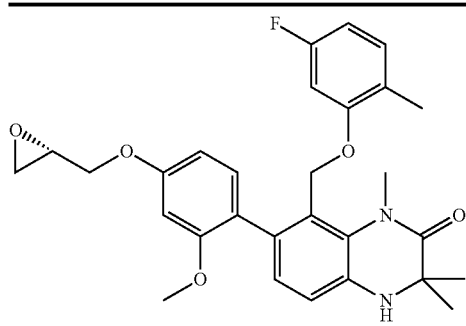

¹H-NMR (400 MHz, CDCl₃)
δ 7.22 (1H, d, J = 8.3 Hz), 6.93-6.84 (2H, m), 6.70 (1H, d, J = 8.0 Hz), 6.64-6.56 (2H, m), 6.38 (1H, td, J = 8.3, 2.4 Hz), 6.04 (1H, dd, J = 11.3, 2.4 Hz), 5.21 (1H, d, J = 13.7 Hz), 4.84 (1H, d, J = 13.7 Hz), 4.30 (1H, dd, J = 11.1, 3.0 Hz), 4.07-3.96 (1H, m), 3.81 (3H, s), 3.68 (1H, s), 3.46 (3H, s), 3.43-3.35 (1H, m), 2.94 (1H, t, J = 4.5 Hz), 2.84-2.76 (1H, m), 2.01 (3H, s), 1.28 (3H, s), 0.91 (3H, s)

Reference compound 5-5

7-[4-(3,3-dimethyl-2-oxobutyl)oxy-2-methoxyphenyl]-8-(5-fluoro-2-methylphenoxy-methyl)-1,3,3-trimethyl-3,4-dihydro-1H-quinoxalin-2-one (the Reference Compound 5-6)

TABLE 11

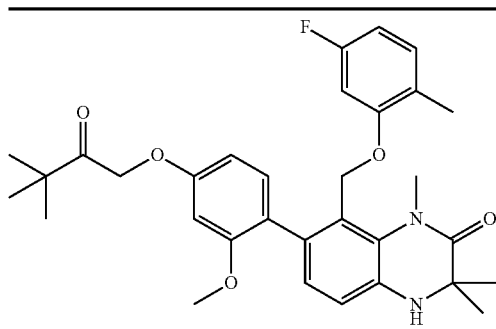

¹H-NMR (400 MHz, CDCl₃)
δ 7.20 (1H, d, J = 8.3 Hz), 6.93-6.83 (2H, m), 6.70 (1H, d, J = 8.0 Hz), 6.64 (1H, d, J = 2.4 Hz), 6.47 (1H, dd, J = 8.3, 2.4 Hz), 6.38 (1H, td, J = 8.3, 2.4 Hz), 6.03 (1H, dd, J = 11.5, 2.4 Hz), 5.21 (1H, d, J = 13.7 Hz), 4.93 (2H, s), 4.84 (1H, d, J = 13.7 Hz), 3.80 (3H, s), 3.69 (1H, s), 3.46 (3H, s), 2.01 (3H, s), 1.28 (12H, s), 0.89 (3H, s)

Reference compound 5-6

Reference Example 6

8-(5-fluoro-2-methylphenoxymethyl)-7-[4-(methoxycarbonylmethyl)oxy-2-methoxyphenyl]-1,3,3-trimethyl-3,4-dihydro-1H-quinoxalin-2-one (the reference compound 6-1)

A mixture of 8-(5-fluoro-2-methylphenoxymethyl)-7-(4-hydroxy-2-methoxy-phenyl)-1,3,3-trimethyl-3,4-dihydro-1H-quinoxalin-2-one (the compound A, 2.0 g, 4.4 mmol), methyl bromoacetate (0.64 mL, 6.8 mmol), potassium carbonate (0.95 g, 6.9 mmol) and dehydrated acetonitrile (45 mL) was refluxed at 100° C. overnight. After allowing to cool at room temperature, water (100 mL) was added to the mixture and the mixture was extracted with ethyl acetate (100 mL). The organic layer was washed with a saturated saline solution (100 mL) and concentrated under reduced pressure, and the obtained residue was purified by silica gel column chromatography (hexane/ethyl acetate) to give the titled reference compound (2.4 g) as pale orange amorphous (quantitative).

TABLE 12

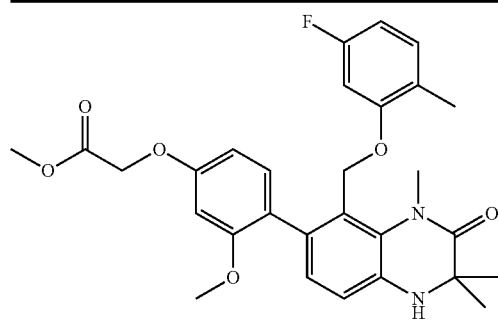

Reference compound 6-1

1H-NMR (400 MHz, DMSO-$d_6$)
δ 7.17 (1H, d, J = 8.3 Hz), 6.99 (1H, t, J = 7.6 Hz), 6.78 (2H, s), 6.71 (1H, d, J = 2.4 Hz), 6.61 (1H, dd, J = 8.3, 2.4 Hz), 6.48 (1H, td, J = 8.3, 2.4 Hz), 6.12-6.03 (2H, m), 5.22 (1H, d, J = 14.1 Hz), 4.86 (2H, s), 4.82 (1H, d, J = 14.1 Hz), 3.79 (3H, s), 3.72 (3H, s), 3.32 (3H, s), 1.92 (3H, s), 1.07 (3H, s), 0.75 (3H, s)

Reference Example 7

2,2-dimethyl-1,3-dioxolane-4-carboxylic acid (the Reference Compound 7-1)

Under ice-cooling, an aqueous (30 mL) solution of potassium permanganate (1.8 g, 11.3 mmol) was added dropwise to an aqueous (50 mL) solution of 2,2-dimethyl-1,3-dioxolane-4-methanol (1.0 g, 7.6 mmol) and potassium hydroxide (1.0 g, 15 mmol), and the mixture was stirred for 2 hours. The mixture was filtered on celite, and the filtrate was concentrated under reduced pressure. A saturated aqueous potassium hydrogen sulfate solution was added to the resulting filtrate until a pH thereof became 4. The mixture was extracted with ethyl acetate (200 mL×2), and the organic layer was dried over anhydrous sodium sulfate and filtered. The filtrate was concentrated under reduced pressure to give the titled reference compound (0.33 g) as a colorless oily product (Yield: 30%).

TABLE 13

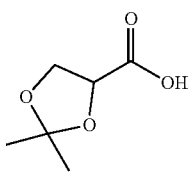

Reference compound 7-1

$^1$H-NMR (500 MHz, CDCl$_3$)
δ 4.62 (1H, dd, J = 7.6, 4.8 Hz), 4.31 (1H, dd, J = 8.9, 7.6 Hz), 4.20 (1H, dd, J = 8.9, 4.8 Hz), 1.54 (3H, s), 1.42 (3H, s)

The reference compound 7-2 was obtained by using a commercially available compound in accordance with the production process of the reference compound 7-1.

(S)-(−)-N-t-butylcarbonyl-2,2-dimethyl-1,3-dioxazolidine-4-carboxylic acid (the reference compound 7-2)

TABLE 14

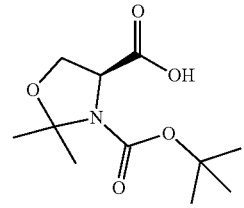

Reference compound 7-2

$^1$H-NMR (400 MHz, CDCl$_3$)
δ 4.54-4.04 (3H, m), 1.52 (12H, s), 1.43 (3H, s)

Reference Example 8

(S)-7-[4-(2-benzyloxyacetoxypropyl)oxy-2-methoxyphenyl]-8-(5-fluoro-2-methyl-phenoxymethyl)-1,3,3-trimethyl-3,4-dihydro-1H-quinoxalin-2-one (the reference compound 8-1)

A mixture of (S)-8-(5-fluoro-2-methylphenoxymethyl)-7-[4-(2-hydroxypropyl)oxy-2-methoxyphenyl]-1,3,3-trimethyl-3,4-dihydro-1H-quinoxalin-2-one (the compound 1-1, 60 mg, 0.12 mmol), benzyloxyacetic acid (4 mg, 0.24 mmol), 1-ethyl-3-(3-dimethyl-aminopropyl)carbodiimide hydrochloride (45 mg, 0.24 mmol), 4-dimethylamino-pyridine (2.9 mg, 0.024 mmol) and anhydrous methylene chloride (3.0 mL) was stirred at room temperature overnight. Water (10 mL) was added to the mixture and the resulting mixture was extracted with ethyl acetate (10 mL×2). The organic layer was washed with a saturated saline solution (10 mL), dried over anhydrous sodium sulfate and filtered. The filtrate was concentrated under reduced pressure and the obtained residue was purified by silica gel column chromatography (hexane/ethyl acetate) to give the titled reference compound (62 mg) as a white solid (Yield: 81%).

TABLE 15

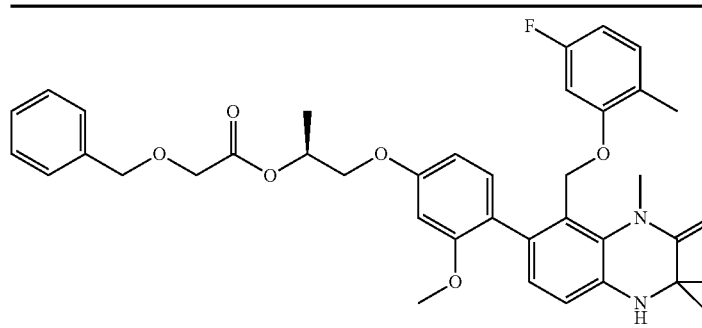

Reference compound 8-1

¹H-NMR (400 MHz, CDCl₃)
δ 7.41-7.27 (5H, m), 7.22 (1H, d, J = 8.8 Hz), 6.93-6.82 (2H, m), 6.70 (1H, d, J = 8.1 Hz), 6.60-6.53 (2H, m), 6.38 (1H, td, J = 8.4, 2.5 Hz), 6.03 (1H, dd, J = 11.2, 2.4 Hz), 5.47-5.37 (1H, m), 5.21 (1H, d, J = 13.7 Hz), 4.83 (1H, d, J = 13.7 Hz), 4.65 (2H, s), 4.17-4.01 (4H, m), 3.79 (3H, s), 3.46 (3H, s), 2.01 (3H, s), 1.43 (3H, d, J = 6.3 Hz), 1.28 (3H, s), 0.90 (3H, s)

The reference compounds 8-2 and 8-3 were obtained by using the compound 1-1, and the reference compounds 7-1 and 7-2 in accordance with the producing process of the reference compound 8-1.

(S)-7-[4-[2-(2,2-dimethyl-1,3-dioxolan-4-ylcarbonyloxy)propyl]oxy-2-methoxyphenyl]-8-(5-fluoro-2-methylphenoxymethyl)-1,3,3-trimethyl-3,4-dihydro-1H-quinoxalin-2-one (the reference compound 8-2)

TABLE 16

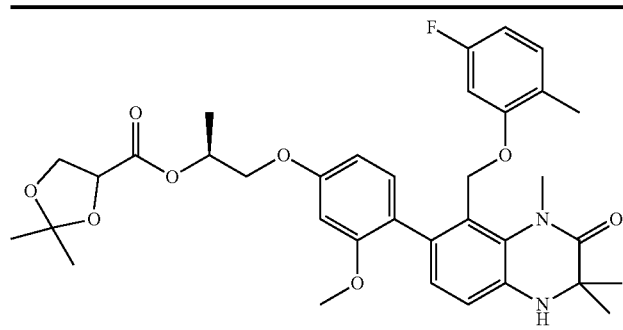

Reference compound 8-2

¹H-NMR (400 MHz, CDCl₃)
δ 7.22 (1H, dd, J = 8.8, 1.5 Hz), 6.93-6.84 (2H, m), 6.70 (1H, d, J = 7.8 Hz), 6.60-6.52 (2H, m), 6.38 (1H, td, J = 8.4, 2.4 Hz), 6.04 (1H, d, J = 11.2 Hz), 5.44-5.35 (1H, m), 5.21 (1H, d, J = 13.9 Hz), 4.84 (1H, d, J = 13.9 Hz), 4.65-4.57 (1H, m), 4.30-4.20 (1H, m), 4.17-4.03 (3H, m), 3.81 (3H, s), 3.68 (1H, s), 3.46 (3H, s), 2.01 (3H, s), 1.52 (3H, d, J = 11.2 Hz), 1.43 (3H, d, J = 6.6 Hz), 1.40 (3H, s), 1.28 (3H, s), 0.90 (3H, s)

(S)-7-[4-[2-(N-t-butoxycarbonyl-2,2-dimethyl-1,3-dioxazolidin-4-ylcarbonyl oxy)-propyl]oxy-2-methoxyphenyl]-8-(5-fluoro-2-methylphenoxymethyl)-1,3,3-trimethyl-3,4-dihydro-1H-quinoxalin-2-one (the Reference Compound 8-3)

TABLE 17

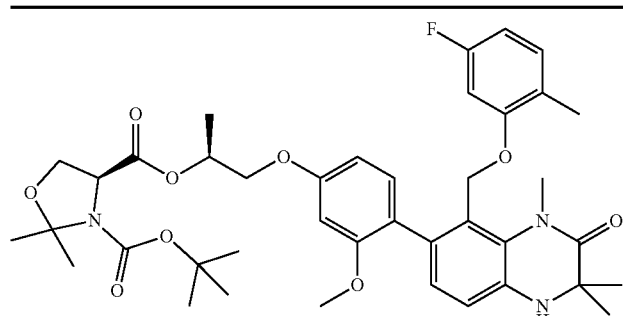

Reference compound 8-3

¹H-NMR (400 MHz, DMSO-d₆)
δ 7.17 (1H, d, J = 8.1 Hz), 6.99 (1H, t, J = 7.7 Hz), 6.78 (2H, s), 6.70-6.59 (2H, m), 6.48 (1H, td, J = 8.5, 2.1 Hz), 6.12-6.02 (2H, m), 5.30-5.16 (2H, m), 4.82 (1H, d, J = 12.8 Hz), 4.44-4.37 (1H, m), 4.22-4.06 (3H, m), 3.97-3.89 (1H, m), 3.78 (3H, s), 3.33 (3H, s), 1.92 (3H, s), 1.56 (3H, s), 1.44-1.27 (15H, m), 1.07 (3H, s), 0.75 (3H, s)

Example 1

(S)-8-(5-fluoro-2-methylphenoxymethyl)-7-[4-(2-hydroxypropyl)oxy-2-methoxy-phenyl]-1,3,3-trimethyl-3,4-dihydro-1H-quinoxalin-2-one (the compound 1-1)

In two pressure resistant reaction tubes with a volume of 200 mL were charged 8-(5-fluoro-2-methylphenoxymethyl)-7-(4-hydroxy-2-methoxyphenyl)-1,3,3-trimethyl-3,4-dihydro-1H-quinoxalin-2-one (the compound A, 7.5 g, 16.7 mmol), dehydrated ethanol (113 mL), potassium carbonate (11.5 g, 83.2 mmol) and (S)-(–)-propylene oxide (5.8 mL, 82.9 mmol), respectively, and sealed, and stirred at 100° C. overnight. After allowing to cool, two reaction mixtures were combined and concentrated under reduced pressure. Ethyl acetate (150 mL) was added to the residue, and the mixture was washed with water (150 mL×2 times) and a saturated saline solution (150 mL). The organic layer was dried over magnesium sulfate, and filtered. After the filtrate was concentrated under reduced pressure, 2-propanol (90 mL) was added to the residue and the resulting mixture was stirred at room temperature overnight. The precipitated solid was collected by filtration, and washed with 2-propanol (7.5 mL). The solid was dried at 60° C. under reduced pressure to give the title compound (11.5 g) as a white solid (Yield: 68%).

TABLE 18

| Compound 1-1 | $^1$H-NMR (400 MHz, CDCl$_3$) |
|---|---|
| (structure) | δ 7.23 (1H, d, J = 8.8 Hz), 6.93-6.84 (2H, m), 6.71 (1H, d, J = 7.7 Hz), 6.62-6.56 (2H, m), 6.38 (1H, td, J = 8.3, 2.2 Hz), 6.04 (1H, dd, J = 11.4, 2.2 Hz), 5.22 (1H, d, J = 13.6 Hz), 4.84 (1H, d, J = 13.6 Hz), 4.29-4.19 (1H, m), 4.05-3.97 (1H, m), 3.91-3.83 (1H, m), 3.81 (3H, s), 3.69 (1H, s), 3.47 (3H, s), 2.31 (1H, d, J = 3.3 Hz), 2.02 (3H, s), 1.32 (3H, d, J = 6.6 Hz), 1.28 (3H, s), 0.91 (3H, s) |

8-(5-Fluoro-2-methylphenoxymethyl)-7-[4-(2-hydroxy-3,3,3-trifluoro-propyl)oxy-2-methoxyphenyl]-1,3,3-trimethyl-3,4-dihydro-1H-quinoxalin-2-one (the compound 1-2)

A mixture of 8-(5-fluoro-2-methylphenoxymethyl)-7-(4-hydroxy-2-methoxyphenyl)-1,3,3-trimethyl-3,4-dihydro-1H-quinoxalin-2-one (the compound A, 100 mg, 0.22 mmol), 3-bromo-1,1,1-trifluoromethyl-2-propanol (46.0 μL, 0.44 mmol), cesium carbonate (145 mg, 44 mmol) and N,N-dimethylformamide (1.5 mL) was stirred at 50° C. overnight. After allowing to cool at room temperature, water (50 mL) was added to the mixture and the resulting mixture was extracted with ethyl acetate (50 mL). The organic layer was washed with a saturated saline solution (50 mL×2), dried over anhydrous magnesium sulfate, and filtered. The filtrate was concentrated under reduced pressure and the obtained residue was purified by silica gel column chromatography (hexane/ethyl acetate) to give the title compound (114 mg) as a white solid (Yield: 91%).

TABLE 19

| Compound 1-2 | $^1$H-NMR (400 MHz, CDCl$_3$) |
|---|---|
| (structure) | δ 7.29-7.21 (1H, m), 6.94-6.84 (2H, m), 6.71 (1H, d, J = 8.0 Hz), 6.63-6.58 (2H, m), 6.39 (1H, td, J = 8.3, 2.4 Hz), 6.04 (1H, dd, J = 11.2, 2.4 Hz), 5.20 (1H, d, J = 13.7 Hz), 4.82 (1H, d, J = 13.7 Hz), 4.45-4.36 (1H, m), 4.32 (1H, dd, J = 9.9, 3.3 Hz), 4.23 (1H, dd, J = 9.9, 6.2 Hz), 3.82 (3H, s), 3.70 (1H, s), 3.46 (3H, s), 2.84 (1H, d, J = 6.6 Hz), 2.02 (3H, s), 1.28 (3H, s), 0.93 (3H, s) |

The compounds 1-3 to 1-6 were obtained by using the compound A and a commercially available compound in accordance with the production process of the compound 1-1 or 1-2.

(R)-8-(5-fluoro-2-methylphenoxymethyl)-7-[4-(2-hydroxypropyl)oxy-2-methoxy-phenyl]-1,3,3-trimethyl-3,4-dihydro-1H-quinoxalin-2-one (the compound 1-3)

TABLE 20

Compound 1-3

$^1$H-NMR (400 MHz, CDCl$_3$)
δ 7.22 (1H, d, J = 9.0 Hz), 6.94-6.84 (2H, m), 6.70 (1H, d, J = 7.8 Hz), 6.63-6.55 (2H, m), 6.38 (1H, td, J = 8.4, 2.4 Hz), 6.05 (1H, dd, J = 11.2, 2.4 Hz), 5.21 (1H, d, J = 13.7 Hz), 4.84 (1H, d, J = 13.7 Hz), 4.30-4.17 (1H, m), 4.04-3.98 (1H, m), 3.91-3.83 (1H, m), 3.81 (3H, s), 3.77-3.64 (1H, m), 3.46 (3H, s), 2.31 (1H, d, J = 3.4 Hz), 2.01 (3H, s), 1.32 (3H, d, J = 6.3 Hz), 1.28 (3H, s), 0.91 (3H, s)

(R)-8-(5-fluoro-2-methylphenoxymethyl)-7-[4-(2-hydroxybutyl)oxy-2-methoxyphenyl]-1,3,3-trimethyl-3,4-dihydro-1H-quinoxalin-2-one (the compound 1-4)

TABLE 21

Compound 1-4

$^1$H-NMR (400 MHz, CDCl$_3$)
δ 7.22 (1H, d, J = 9.0 Hz), 6.93-6.85 (2H, m), 6.70 (1H, d, J = 8.0 Hz), 6.62-6.57 (2H, m), 6.38 (1H, td, J = 8.3, 2.5 Hz), 6.04 (1H, dd, J = 11.3, 2.5 Hz), 5.21 (1H, d, J = 13.7 Hz), 4.85 (1H, d, J = 13.7 Hz), 4.05 (1H, dd, J = 8.5, 2.7 Hz), 4.01-3.87 (2H, m), 3.81 (3H, s), 3.68 (1H, s), 3.47 (3H, s), 2.25 (1H, d, J = 2.7 Hz), 2.01 (3H, s), 1.72-1.60 (2H, m), 1.28 (3H, s), 1.06 (3H, t, J = 7.4 Hz), 0.91(3H, s)

(S)-8-(5-fluoro-2-methylphenoxymethyl)-7-[4-(2-hydroxybutyl)oxy-2-methoxyphenyl]-1,3,3-trimethyl-3,4-dihydro-1H-quinoxalin-2-one (the compound 1-5)

TABLE 22

Compound 1-5

$^1$H-NMR (400 MHz, CDCl$_3$)
δ 7.22 (1H, d, J = 8.8 Hz), 6.93-6.84 (2H, m), 6.70 (1H, d, J = 8.0 Hz), 6.62-6.56 (2H, m), 6.38 (1H, td, J = 8.4, 2.6 Hz), 6.04 (1H, dd, J = 11.5, 2.6 Hz), 5.21 (1H, d, J = 13.6 Hz), 4.84 (1H, d, J = 13.6 Hz), 4.05 (1H, dd, J = 9.0, 2.7 Hz), 4.02-3.87 (2H, m), 3.81 (3H, s), 3.68 (1H, s), 3.47 (3H, s), 2.25 (1H, d, J = 2.7 Hz), 2.01 (3H, s), 1.71-1.60 (2H, m), 1.28 (3H, s), 1.06 (3H, t, J = 7.4 Hz), 0.91 (3H, s)

(R)-7-[4-(2-ethoxycarbonyl-2-hydroxyethyl)oxy-2-methoxyphenyl]-8-(5-fluoro-2-methylphenoxymethyl)-1,3,3-trimethyl-3,4-dihydro-1H-quinoxalin-2-one (the compound 1-6)

TABLE 23

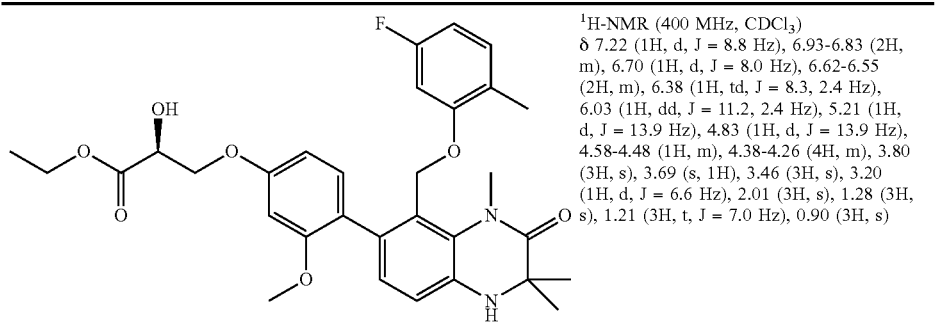

Compound 1-6

¹H-NMR (400 MHz, CDCl₃)
δ 7.22 (1H, d, J = 8.8 Hz), 6.93-6.83 (2H, m), 6.70 (1H, d, J = 8.0 Hz), 6.62-6.55 (2H, m), 6.38 (1H, td, J = 8.3, 2.4 Hz), 6.03 (1H, dd, J = 11.2, 2.4 Hz), 5.21 (1H, d, J = 13.9 Hz), 4.83 (1H, d, J = 13.9 Hz), 4.58-4.48 (1H, m), 4.38-4.26 (4H, m), 3.80 (3H, s), 3.69 (s, 1H), 3.46 (3H, s), 3.20 (1H, d, J = 6.6 Hz), 2.01 (3H, s), 1.28 (3H, s), 1.21 (3H, t, J = 7.0 Hz), 0.90 (3H, s)

Example 2

(S)-7-[4-(2,4-dihydroxybutyl)oxy-2-methoxyphenyl]-8-(5-fluoro-2-methyl-phenoxymethyl)-1,3,3-trimethyl-3,4-dihydro-1H-quinoxalin-2-one (the compound 2-1)

Palladium on carbon (50 mg) was added to a methanol (6 mL) solution of (S)-7-[4-(4-benzyloxy-2-hydroxybutyl)oxy-2-methoxyphenyl]-8-(5-fluoro-2-methyl-phenoxymethyl)-1,3,3-trimethyl-3,4-dihydro-1H-quinoxalin-2-one (the Reference Compound 3-1, 254 mg, 0.405 mmol), and the mixture was stirred under hydrogen atmosphere at room temperature overnight. The mixture was filtered, and the filtrate was concentrated under reduced pressure. The obtained residue was purified by silica gel column chromatography (hexane/ethyl acetate) to give the title compound (213 mg) as white amorphous (Yield: 98%).

TABLE 24

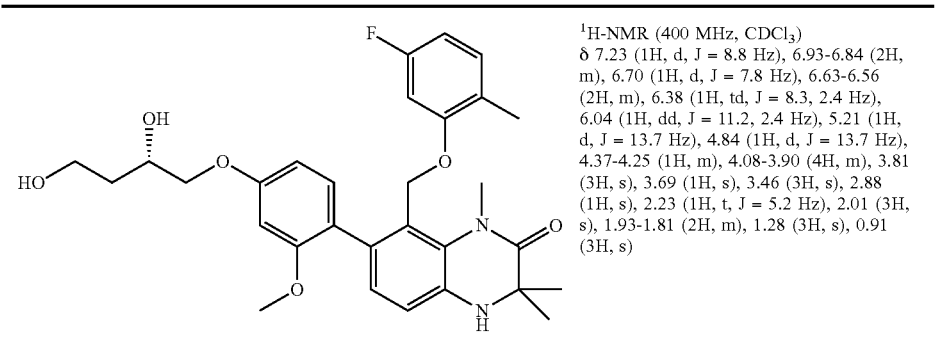

Compound 2-1

¹H-NMR (400 MHz, CDCl₃)
δ 7.23 (1H, d, J = 8.8 Hz), 6.93-6.84 (2H, m), 6.70 (1H, d, J = 7.8 Hz), 6.63-6.56 (2H, m), 6.38 (1H, td, J = 8.3, 2.4 Hz), 6.04 (1H, dd, J = 11.2, 2.4 Hz), 5.21 (1H, d, J = 13.7 Hz), 4.84 (1H, d, J = 13.7 Hz), 4.37-4.25 (1H, m), 4.08-3.90 (4H, m), 3.81 (3H, s), 3.69 (1H, s), 3.46 (3H, s), 2.88 (1H, s), 2.23 (1H, t, J = 5.2 Hz), 2.01 (3H, s), 1.93-1.81 (2H, m), 1.28 (3H, s), 0.91 (3H, s)

(R)-7-[4-(2,4-dihydroxybutyl)oxy-2-methoxyphenyl]-8-(5-fluoro-2-methyl-phenoxymethyl)-1,3,3-trimethyl-3,4-dihydro-1H-quinoxalin-2-one (the compound 2-2)

A mixture of 8-(5-fluoro-2-methylphenoxymethyl)-7-(4-hydroxy-2-methoxyphenyl)-1,3,3-trimethyl-3,4-dihydro-1H-quinoxalin-2-one (the compound A, 451 mg, 1.0 mmol), (R)-4-benzyloxy-1,2-epoxybutane (the Reference Compound 2-2, 267 mg, 1.5 mmol), cesium carbonate (828 mg, 2.5 mmol) and N,N-dimethylformamide (4.5 mL) was stirred at 70° C. overnight. After allowing to cool at room temperature, water (100 mL) was added to the mixture and the resulting mixture was extracted with ethyl acetate (100 mL). The organic layer was washed with an aqueous saturated ammonium chloride solution (100 mL) and a saturated saline solution (100 mL), dried over anhydrous magnesium sulfate, and filtered. The filtrate was concentrated under reduced pressure and the obtained residue was purified by silica gel column chromatography (hexane/ethyl acetate). The obtained intermediate ((R)-7-[4-(4-benzyloxy-2-hydroxybutyl)oxy-2-methoxyphenyl]-8-(5-fluoro-2-methyl-phenoxy-methyl)-1,3,3-trimethyl-3,4-dihydro-1H-quinoxalin-2-one) was dissolved in methanol (5.0 mL), palladium on carbon (30 mg) was added to the solution and the resulting mixture was stirred under hydrogen atmosphere at room temperature overnight. The mixture was filtered with methanol (30 mL) on celite. The filtrate was concentrated under reduced pressure and the obtained residue was purified by silica gel column chromatography (chloroform/methanol) to give the title compound (341 mg) as white amorphous (Yield: 63%).

TABLE 25

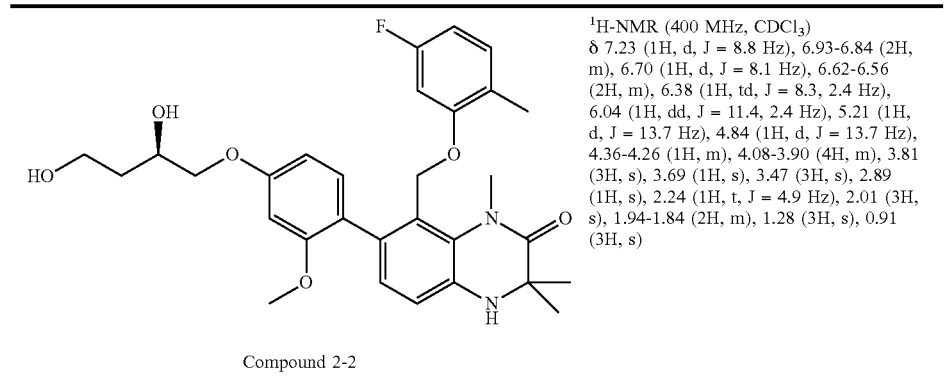

$^1$H-NMR (400 MHz, CDCl$_3$)
δ 7.23 (1H, d, J = 8.8 Hz), 6.93-6.84 (2H, m), 6.70 (1H, d, J = 8.1 Hz), 6.62-6.56 (2H, m), 6.38 (1H, td, J = 8.3, 2.4 Hz), 6.04 (1H, dd, J = 11.4, 2.4 Hz), 5.21 (1H, d, J = 13.7 Hz), 4.84 (1H, d, J = 13.7 Hz), 4.36-4.26 (1H, m), 4.08-3.90 (4H, m), 3.81 (3H, s), 3.69 (1H, s), 3.47 (3H, s), 2.89 (1H, s), 2.24 (1H, t, J = 4.9 Hz), 2.01 (3H, s), 1.94-1.84 (2H, m), 1.28 (3H, s), 0.91 (3H, s)

Compound 2-2

The compound 2-3 was obtained by using the reference compound 8-1 in accordance with the producing process of the compound 2-1.

(S)-8-(5-fluoro-2-methylphenoxymethyl)-7-[4-(2-hydroxyacetoxypropyl)oxy-2-methoxyphenyl]-1,3,3-trimethyl-3,4-dihydro-1H-quinoxalin-2-one (the compound 2-3)

TABLE 26

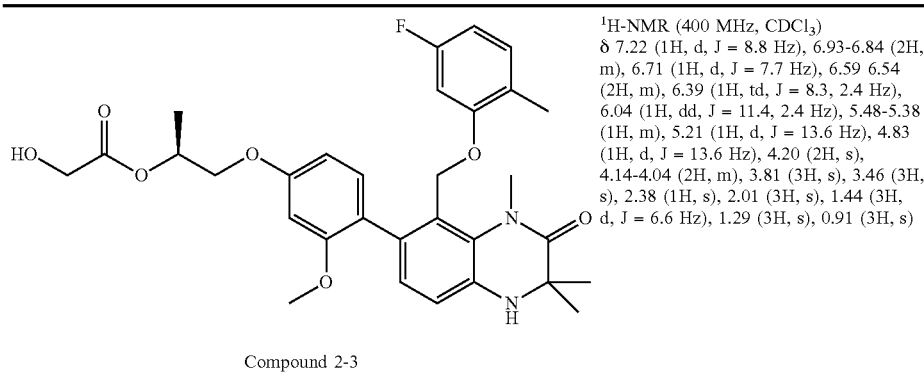

$^1$H-NMR (400 MHz, CDCl$_3$)
δ 7.22 (1H, d, J = 8.8 Hz), 6.93-6.84 (2H, m), 6.71 (1H, d, J = 7.7 Hz), 6.59 6.54 (2H, m), 6.39 (1H, td, J = 8.3, 2.4 Hz), 6.04 (1H, dd, J = 11.4, 2.4 Hz), 5.48-5.38 (1H, m), 5.21 (1H, d, J = 13.6 Hz), 4.83 (1H, d, J = 13.6 Hz), 4.20 (2H, s), 4.14-4.04 (2H, m), 3.81 (3H, s), 3.46 (3H, s), 2.38 (1H, s), 2.01 (3H, s), 1.44 (3H, d, J = 6.6 Hz), 1.29 (3H, s), 0.91 (3H, s)

Compound 2-3

Example 3

8-(5-fluoro-2-methylphenoxymethyl)-7-[4-(2-hydroxyethyl)oxy-2-methoxyphenyl]-1,3,3-trimethyl-3,4-dihydro-1H-quinoxalin-2-one (the compound 3-1)

1N hydrochloric acid (2.0 mL) was added to a tetrahydrofuran-methanol mixed solution (1:1, 4.0 mL) of 8-(5-fluoro-2-methylphenoxymethyl)-7-[4-(2-tetrahydropyran-2-yloxyethyl)oxy-2-methoxyphenyl]-1,3,3-trimethyl-3,4-dihydro-1H-quinoxalin-2-one (the reference compound 4-1, 130 mg, 0.22 mmol), and the resulting mixture was stirred at room temperature overnight. The mixture was diluted with ethyl acetate (20 mL), and the organic layer was washed with a saturated aqueous sodium hydrogen carbonate solution (20 mL) and a saturated saline solution (20 mL). The organic layer was dried over anhydrous magnesium sulfate, and filtered. The filtrate was concentrated under reduced pressure and the obtained residue was purified by silica gel column chromatography (hexane/ethyl acetate) to give the title compound (72 mg) as a colorless oily product (Yield: 65%).

TABLE 27

$^1$H-NMR (400 MHz, CDCl$_3$)
δ 7.23 (1H, d, J = 8.8 Hz), 6.93-6.84 (2H, m), 6.71 (1H, d, J = 8.0 Hz), 6.64-6.57 (2H, m), 6.38 (1H, td, J = 8.4, 2.4 Hz), 6.04 (1H, dd, J = 11.2, 2.4 Hz), 5.22 (1H, d, J = 13.7 Hz), 4.85 (1H, d, J = 13.7 Hz), 4.21-4.12 (2H, m), 4.05-3.97 (2H, m), 3.81 (3H, s), 3.69 (1H, s), 3.47 (3H, s), 2.02 (3H, s), 1.28 (3H, s), 0.91 (3H, s)

Compound 3-1

Example 4

7-[4-(2,3-dihydroxypropyl)oxy-2-methoxyphenyl]-8-(5-fluoro-2-methylphenoxymethyl)-1,3,3-trimethyl-3,4-dihydro-1H-quinoxalin-2-one (the compound 4-1)

Under ice-cooling, trifluoroacetic acid (4.0 mL) was added to a methylene chloride (20 mL) solution of 7-[4-(2,2-dimethyl-1,3-dioxolan-4-ylmethyl)oxy-2-methoxyphenyl]-8-(5-fluoro-2-methylphenoxymethyl)-1,3,3-trimethyl-3,4-dihydro-1H-quinoxalin-2-one (the reference compound 5-1, 685 mg, 1.2 mmol) and the resulting mixture was stirred at room temperature for 3 hours. Water (1.0 mL) was added to the mixture, and the resulting mixture was further stirred at room temperature for 1 hour. The mixture was concentrated under reduced pressure, and the obtained residue was diluted with ethyl acetate (150 mL). The organic layer was washed with a saturated aqueous sodium hydrogen carbonate solution (100 mL) and a saturated saline solution (100 mL), dried over anhydrous magnesium sulfate, and filtered. The filtrate was concentrated under reduced pressure and the obtained residue was purified by silica gel column chromatography (hexane/ethyl acetate) to give the title compound (556 mg) as white amorphous (Yield: 88%).

TABLE 28

$^1$H-NMR (400 MHz, CDCl$_3$)
δ 7.23 (1H, d, J = 8.5 Hz), 6.93-6.83 (2H, m), 6.71 (1H, d, J = 8.0 Hz), 6.63-6.57 (2H, m), 6.39 (1H, td, J = 8.3, 2.4 Hz), 6.04 (1H, dd, J = 11.2, 2.4 Hz), 5.20 (1H, d, J = 13.4 Hz), 4.83 (1H, d, J = 13.4 Hz), 4.20-4.08 (3H, m), 3.93-3.75 (2H, m), 3.81 (3H, s), 3.69 (1H, s), 3.46 (3H, s), 2.58 (1H, d, J = 4.1 Hz), 2.02 (3H, s), 1.98 (1H, t, J = 6.3 Hz), 1.28 (3H, s), 0.92 (3H, s)

Compound 4-1

The compounds 4-2 and 4-3 were obtained by using the reference compounds 5-1 and 5-2 in accordance with the producing process of the compound 4-1.

(S)-7-[4-(2,3-dihydroxypropyl)oxy-2-methoxyphenyl]-8-(5-fluoro-2-methylphenoxy-methyl)-1,3,3-trimethyl-3,4-dihydro-1H-quinoxalin-2-one (the compound 4-2)

TABLE 29

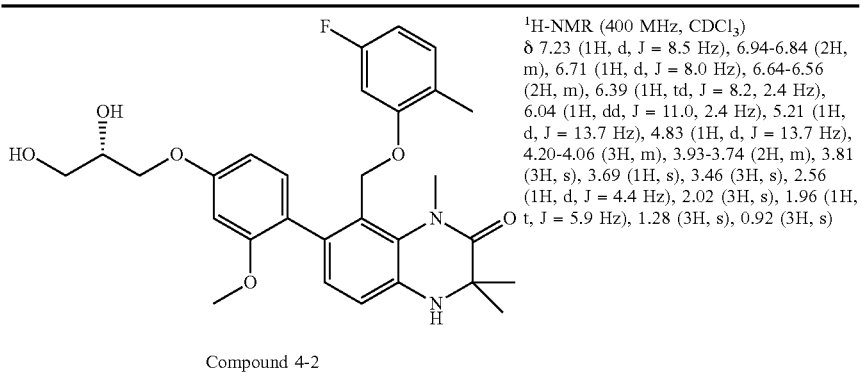

Compound 4-2

¹H-NMR (400 MHz, CDCl₃)
δ 7.23 (1H, d, J = 8.5 Hz), 6.94-6.84 (2H, m), 6.71 (1H, d, J = 8.0 Hz), 6.64-6.56 (2H, m), 6.39 (1H, td, J = 8.2, 2.4 Hz), 6.04 (1H, dd, J = 11.0, 2.4 Hz), 5.21 (1H, d, J = 13.7 Hz), 4.83 (1H, d, J = 13.7 Hz), 4.20-4.06 (3H, m), 3.93-3.74 (2H, m), 3.81 (3H, s), 3.69 (1H, s), 3.46 (3H, s), 2.56 (1H, d, J = 4.4 Hz), 2.02 (3H, s), 1.96 (1H, t, J = 5.9 Hz), 1.28 (3H, s), 0.92 (3H, s)

(R)-7-[4-(2,3-dihydroxypropyl)oxy-2-methoxyphenyl]-8-(5-fluoro-2-methylphenoxy-methyl)-1,3,3-trimethyl-3,4-dihydro-1H-quinoxalin-2-one (the compound 4-3)

TABLE 30

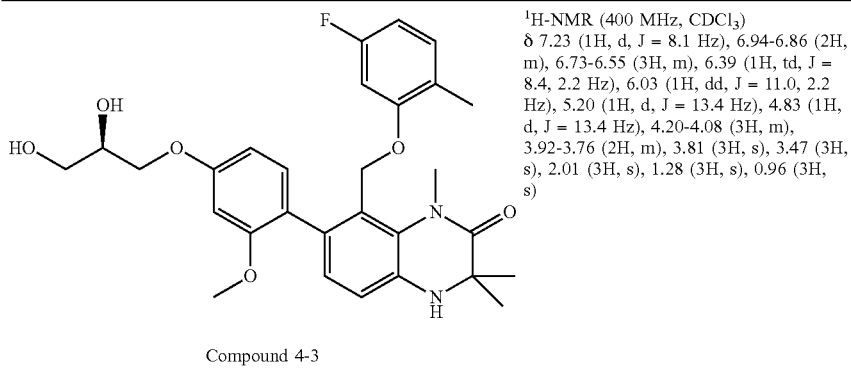

Compound 4-3

¹H-NMR (400 MHz, CDCl₃)
δ 7.23 (1H, d, J = 8.1 Hz), 6.94-6.86 (2H, m), 6.73-6.55 (3H, m), 6.39 (1H, td, J = 8.4, 2.2 Hz), 6.03 (1H, dd, J = 11.0, 2.2 Hz), 5.20 (1H, d, J = 13.4 Hz), 4.83 (1H, d, J = 13.4 Hz), 4.20-4.08 (3H, m), 3.92-3.76 (2H, m), 3.81 (3H, s), 3.47 (3H, s), 2.01 (3H, s), 1.28 (3H, s), 0.96 (3H, s)

Example 5

(R)-7-[4-(3-cyano-2-hydroxypropyl)oxy-2-methoxyphenyl]-8-(5-fluoro-2-methyl-phenoxymethyl)-1,3,3-trimethyl-3,4-dihydro-1H-quinoxalin-2-one (the compound 5-1)

A mixture of (R)-7-[4-(2,3-epoxypropyl)oxy-2-methoxyphenyl]-8-(5-fluoro-2-methylphenoxymethyl)-1,3,3-trimethyl-3,4-dihydro-1H-quinoxalin-2-one (the reference compound 5-4, 235 mg, 0.46 mmol), potassium cyanide (66 mg, 1.0 mmol), water (0.90 mL) and N,N-dimethylformamide (5.0 mL) was stirred at room temperature overnight. To the mixture was added a saturated saline solution (30 mL), and the resulting mixture was extracted with ethyl acetate (30 mL×3). The organic layer was washed with a saturated saline solution (40 mL), dried over anhydrous magnesium sulfate, and filtered. The filtrate was concentrated under reduced pressure and the obtained residue was purified by silica gel column chromatography (hexane/ethyl acetate) to give the title compound (208 mg) as white amorphous (Yield: 87%).

TABLE 31

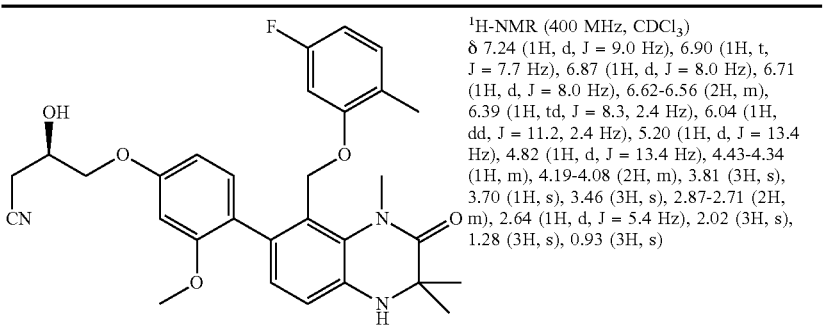

¹H-NMR (400 MHz, CDCl₃)
δ 7.24 (1H, d, J = 9.0 Hz), 6.90 (1H, t, J = 7.7 Hz), 6.87 (1H, d, J = 8.0 Hz), 6.71 (1H, d, J = 8.0 Hz), 6.62-6.56 (2H, m), 6.39 (1H, td, J = 8.3, 2.4 Hz), 6.04 (1H, dd, J = 11.2, 2.4 Hz), 5.20 (1H, d, J = 13.4 Hz), 4.82 (1H, d, J = 13.4 Hz), 4.43-4.34 (1H, m), 4.19-4.08 (2H, m), 3.81 (3H, s), 3.70 (1H, s), 3.46 (3H, s), 2.87-2.71 (2H, m), 2.64 (1H, d, J = 5.4 Hz), 2.02 (3H, s), 1.28 (3H, s), 0.93 (3H, s)

Compound 5-1

The compound 5-2 was obtained by using the reference compound 5-5 and a commercially available compound in accordance with the producing process of the compound 5-1.

(S)-7-[4-(3-cyano-2-hydroxypropyl)oxy-2-methoxyphenyl]-8-(5-fluoro-2-methyl-phenoxymethyl)-1,3,3-trimethyl-3,4-dihydro-1H-quinoxalin-2-one (the compound 5-2)

TABLE 32

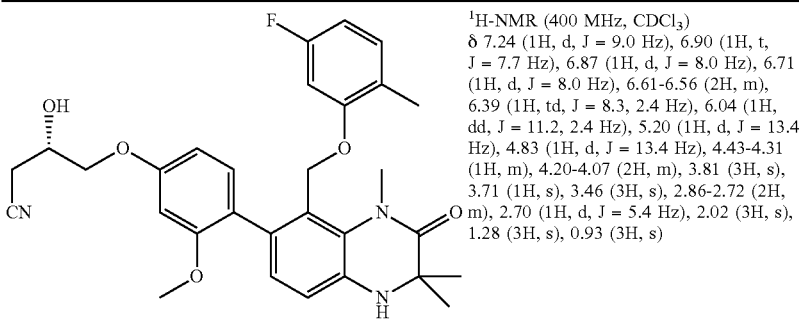

¹H-NMR (400 MHz, CDCl₃)
δ 7.24 (1H, d, J = 9.0 Hz), 6.90 (1H, t, J = 7.7 Hz), 6.87 (1H, d, J = 8.0 Hz), 6.71 (1H, d, J = 8.0 Hz), 6.61-6.56 (2H, m), 6.39 (1H, td, J = 8.3, 2.4 Hz), 6.04 (1H, dd, J = 11.2, 2.4 Hz), 5.20 (1H, d, J = 13.4 Hz), 4.83 (1H, d, J = 13.4 Hz), 4.43-4.31 (1H, m), 4.20-4.07 (2H, m), 3.81 (3H, s), 3.71 (1H, s), 3.46 (3H, s), 2.86-2.72 (2H, m), 2.70 (1H, d, J = 5.4 Hz), 2.02 (3H, s), 1.28 (3H, s), 0.93 (3H, s)

Compound 5-2

Example 6

7-[4-(3-fluoro-2-hydroxypropyl)oxy-2-methoxyphenyl]-8-(5-fluoro-2-methylphenoxy-methyl)-1,3,3-trimethyl-3,4-dihydro-1H-quinoxalin-2-one (the compound 6-1)

Under ice-cooling, N,N-diethylaminosulfur trifluoride (76 μL, 0.58 mmol) was added to a methylene chloride (4.0 mL) solution of 7-[4-(2,3-dihydroxypropyl)oxy-2-methoxyphenyl]-8-(5-fluoro-2-methylphenoxymethyl)-1,3,3-trimethyl-3,4-dihydro-1H-quinoxalin-2-one (the compound 4-1, 200 mg, 0.38 mmol) and the resulting mixture was stirred for 3 hours. The mixture was filtered using silica gel and the filtrate was washed with ethyl acetate (20 mL×3). The filtrate was concentrated under reduced pressure and the obtained residue was purified by silica gel column chromatography (hexane/ethyl acetate) to give the title compound (22 mg) as white amorphous (Yield: 11%).

TABLE 33

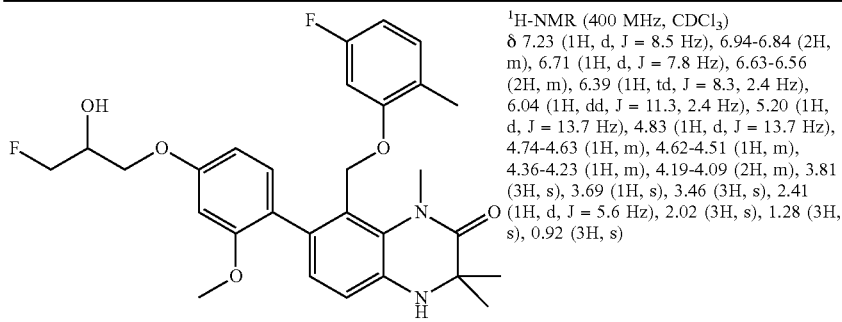

¹H-NMR (400 MHz, CDCl₃)
δ 7.23 (1H, d, J = 8.5 Hz), 6.94-6.84 (2H, m), 6.71 (1H, d, J = 7.8 Hz), 6.63-6.56 (2H, m), 6.39 (1H, td, J = 8.3, 2.4 Hz), 6.04 (1H, dd, J = 11.3, 2.4 Hz), 5.20 (1H, d, J = 13.7 Hz), 4.83 (1H, d, J = 13.7 Hz), 4.74-4.63 (1H, m), 4.62-4.51 (1H, m), 4.36-4.23 (1H, m), 4.19-4.09 (2H, m), 3.81 (3H, s), 3.69 (1H, s), 3.46 (3H, s), 2.41 (1H, d, J = 5.6 Hz), 2.02 (3H, s), 1.28 (3H, s), 0.92 (3H, s)

Compound 6-1

Example 7

7-[4-(3-ethoxycarbonyl-2-hydroxypropyl)oxy-2-methoxyphenyl]-8-(5-fluoro-2-methylphenoxymethyl)-1,3,3-trimethyl-3,4-dihydro-1H-quinoxalin-2-one (the compound 7-1)

Under argon gas atmosphere, an n-butyllithium 1.6M hexane solution (4.2 mL, 6.7 mmol) was added to a mixed solution of anhydrous tetrahydrofuran (8.0 mL) and N,N-diisopropylamine (0.95 mL, 6.8 mmol) under ice-cooling and the resulting mixture was stirred for 30 minutes. The mixture was cooled to −78° C., and ethyl acetate (0.66 mL, 6.8 mmol) was added thereto and the resulting mixture was stirred for 1 hour. To the mixture was added dropwise an anhydrous tetrahydrofuran (8 mL) solution of 8-(5-fluoro-2-methylphenoxymethyl)-7-[4-(methoxycarbonylmethyl)oxy-2-methoxyphenyl]-1,3,3-trimethyl-3,4-dihydro-1H-quinoxalin-2-one (the Reference Compound 6-1, 2.4 g, 4.6 mmol) over 5 minutes. The mixture was stirred accompanying with raising of the temperature for 2.5 hours, and 1N hydrochloric acid (15 mL) was added at −16° C. Water (50 mL) was added to the mixture and the resulting mixture was extracted with ethyl acetate (100 mL). The organic layer was washed with an aqueous saturated ammonium chloride solution (50 mL) and a saturated saline solution (50 mL). The organic layer was dried over anhydrous magnesium sulfate, and filtered. The filtrate was concentrated under reduced pressure, and the obtained intermediate (7-[4-(3-ethoxycarbonyl-2-oxopropyl)oxy-2-methoxyphenyl]-8-(5-fluoro-2-methylphenoxy-methyl)-1,3,3-trimethyl-3,4-dihydro-1H-quinoxalin-2-one) was dissolved in tetrahydrofuran (25 mL). Under ice-cooling, to the solution was added sodium borohydride (0.35 g, 9.3 mmol) and the mixture was stirred for 15 minutes. To the mixture were added water (50 mL) and 1N hydrochloric acid (15 mL), and the resulting mixture was extracted with ethyl acetate (100 mL). The organic layer was washed with an aqueous saturated ammonium chloride solution (50 mL) and a saturated saline solution (50 mL). The organic layer was concentrated under reduced pressure and the obtained residue was purified by silica gel column chromatography (hexane/ethyl acetate) to give the title compound (1.4 g) as white amorphous (Yield: 54%).

TABLE 34

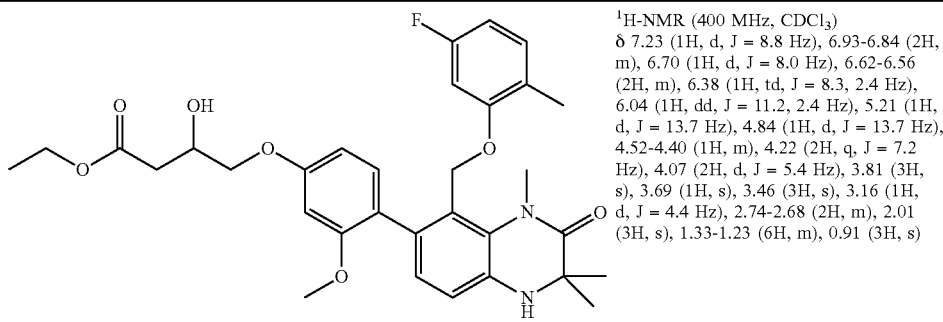

$^1$H-NMR (400 MHz, CDCl$_3$)
δ 7.23 (1H, d, J = 8.8 Hz), 6.93-6.84 (2H, m), 6.70 (1H, d, J = 8.0 Hz), 6.62-6.56 (2H, m), 6.38 (1H, td, J = 8.3, 2.4 Hz), 6.04 (1H, dd, J = 11.2, 2.4 Hz), 5.21 (1H, d, J = 13.7 Hz), 4.84 (1H, d, J = 13.7 Hz), 4.52-4.40 (1H, m), 4.22 (2H, q, J = 7.2 Hz), 4.07 (2H, d, J = 5.4 Hz), 3.81 (3H, s), 3.69 (1H, s), 3.46 (3H, s), 3.16 (1H, d, J = 4.4 Hz), 2.74-2.68 (2H, m), 2.01 (3H, s), 1.33-1.23 (6H, m), 0.91 (3H, s)

Compound 7-1

The compound 7-2 was obtained by using the reference compound 6-1 and a commercially available compound in accordance with the producing process of the compound 7-1.

7-[4-(3-t-butoxycarbonyl-2-hydroxypropyl)oxy-2-methoxyphenyl]-8-(5-fluoro-2-methylphenoxymethyl)-1,3,3-trimethyl-3,4-dihydro-1H-quinoxalin-2-one (the compound 7-2)

TABLE 35

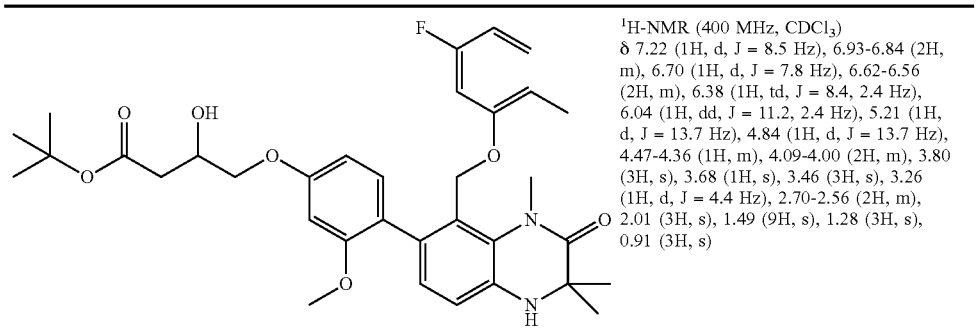

$^1$H-NMR (400 MHz, CDCl$_3$)
δ 7.22 (1H, d, J = 8.5 Hz), 6.93-6.84 (2H, m), 6.70 (1H, d, J = 7.8 Hz), 6.62-6.56 (2H, m), 6.38 (1H, td, J = 8.4, 2.4 Hz), 6.04 (1H, dd, J = 11.2, 2.4 Hz), 5.21 (1H, d, J = 13.7 Hz), 4.84 (1H, d, J = 13.7 Hz), 4.47-4.36 (1H, m), 4.09-4.00 (2H, m), 3.80 (3H, s), 3.68 (1H, s), 3.46 (3H, s), 3.26 (1H, d, J = 4.4 Hz), 2.70-2.56 (2H, m), 2.01 (3H, s), 1.49 (9H, s), 1.28 (3H, s), 0.91 (3H, s)

Compound 7-2

Example 8

7-[4-(3,3-dimethyl-2-hydroxybutyl)oxy-2-methoxyphenyl]-8-(5-fluoro-2-methylphenoxymethyl)-1,3,3-trimethyl-3,4-dihydro-1H-quinoxalin-2-one (the compound 8-1)

Under ice-cooling, sodium borohydride (9.0 mg, 0.24 mmol) was added to a methanol (1.0 mL) solution of 7-[4-(3,3-dimethyl-2-oxobutyl)oxy-2-methoxyphenyl]-8-(5-fluoro-2-methylphenoxymethyl)-1,3,3-trimethyl-3,4-dihydro-1H-quinoxalin-2-one (the reference compound 5-6, 55 mg, 0.10 mmol), and the resulting mixture was stirred for 1 hour. To the mixture was added 1N hydrochloric acid (20 mL), and the resulting mixture was extracted with ethyl acetate (15 mL×2). The organic layers were combined and washed with a saturated aqueous sodium hydrogen carbonate solution (20 mL) and a saturated saline solution (20 mL), dried over anhydrous magnesium sulfate, and filtered. The filtrate was concentrated under reduced pressure to give the title compound (51 mg) as pink amorphous (Yield: 92%).

TABLE 36

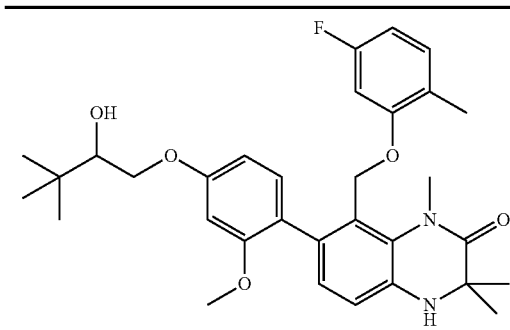

$^1$H-NMR (400 MHz, CDCl$_3$)
δ 7.23 (1H, d, J = 8.5 Hz), 6.93-6.84 (2H, m), 6.70 (1H, d, J = 8.0 Hz), 6.63-6.56 (2H, m), 6.38 (1H, td, J = 8.3, 2.4 Hz), 6.05 (1H, dd, J = 11.2, 2.4 Hz), 5.22 (1H, d, J = 13.7 Hz), 4.85 (1H, d, J = 13.7 Hz), 4.22-4.14 (1H, m), 3.93 (1H, t, J = 9.0 Hz), 3.81 (3H, s), 3.77-3.64 (2H, m), 3.47 (3H, s), 2.37 (1H, d, J = 2.9 Hz), 2.02 (3H, s), 1.28 (3H, s), 1.04 (9H, s), 0.91 (3H, s)

Compound 8-1

Example 9

7-[4-(3-Carboxy-2-hydroxypropyl)oxy-2-methoxyphenyl]-8-(5-fluoro-2-methylphenoxymethyl)-1,3,3-trimethyl-3,4-dihydro-1H-quinoxalin-2-one (the compound 9-1)

A mixture of 7-[4-(3-ethoxycarbonyl-2-hydroxypropyl)oxy-2-methoxyphenyl]-8-(5-fluoro-2-methylphenoxymethyl)-1,3,3-trimethyl-3,4-dihydro-1H-quinoxalin-2-one (the compound 7-1, 1.9 g, 3.3 mmol), 4N aqueous sodium hydroxide solution (10 mL) and methanol (15 mL) was stirred at 50° C. overnight. After allowing to cool at room temperature, 1N hydrochloric acid (45 mL) was added to the mixture. The precipitated solid was collected by filtration, and washed with water (50 mL). The obtained solid was dried under reduced pressure at 40° C. for 4 hours to give the title compound (1.6 g) as reddish brown solid (Yield: 88%).

TABLE 37

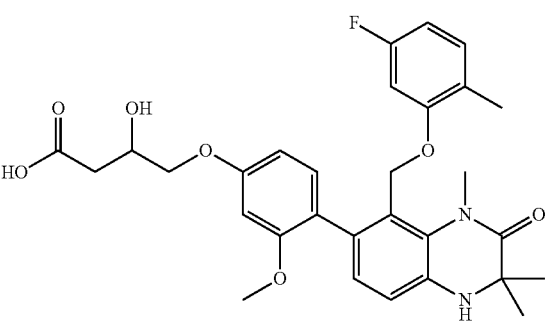

$^1$H-NMR (400 MHz, DMSO-d$_6$)
δ 12.19 (1H, s), 7.16 (1H, d, J = 8.4 Hz), 6.98 (1H, t, J = 7.7 Hz), 6.81-6.73 (2H, m), 6.68 (1H, d, J = 2.3 Hz), 6.64 (1H, dd, J = 8.3, 2.3 Hz), 6.48 (1H, td, J = 8.3, 2.3 Hz), 6.12-6.00 (2H, m), 5.31-5.13 (2H, m), 4.83 (1H, d, J = 13.9 Hz), 4.27-4.16 (1H, m), 3.97 (2H, d, J = 5.1 Hz), 3.79 (3H, s), 3.32 (3H, s), 2.62-2.34 (2H, m), 1.92 (3H, s), 1.07 (3H, s), 0.74 (3H, s)

Compound 9-1

Example 10

8-(5-fluoro-2-methylphenoxymethyl)-7-[4-[3-(N-pyrrolidylcarbonyl)-2-hydroxypropyl]oxy-2-methoxyphenyl]-1,3,3-trimethyl-3,4-dihydro-1H-quinoxalin-2-one (the compound 10-1)

A mixture of 7-[4-(3-carboxy-2-hydroxypropyl)oxy-2-methoxyphenyl]-8-(5-fluoro-2-methylphenoxymethyl)-1,3,3-trimethyl-3,4-dihydro-H-quinoxalin-2-one (the compound 9-1, 110 mg, 0.20 mmol), 1-hydroxybenzotriazole (48 mg, 0.31 mmol), 1-ethyl-3-(3-dimethylaminopropyl)carbodiimide hydrochloride (59 mg, 0.31 mmol), pyrrolidine (33 µL, 0.40 mmol), N-methylmorpholine (88 µL, 0.80 mmol) and N,N-dimethylformamide (2.0 mL) was stirred at room temperature overnight. A saturated saline solution (10 mL) was added to the mixture, and the resulting mixture was extracted with ethyl acetate (10 mL×2). The organic layer was washed with a saturated saline solution (20 mL), dried over anhydrous magnesium sulfate, and filtered. The filtrate was concentrated under reduced pressure and the obtained residue was purified by silica gel column chromatography (chloroform/methanol) to give the title compound (24 mg) as pale brown amorphous (Yield: 20%).

TABLE 38

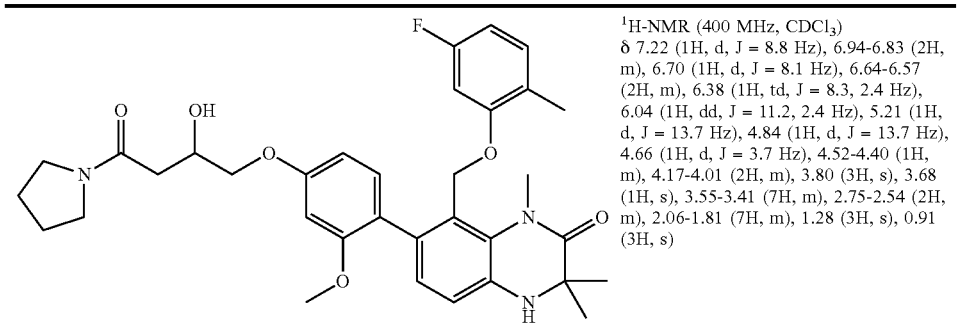

$^1$H-NMR (400 MHz, CDCl$_3$)
δ 7.22 (1H, d, J = 8.8 Hz), 6.94-6.83 (2H, m), 6.70 (1H, d, J = 8.1 Hz), 6.64-6.57 (2H, m), 6.38 (1H, td, J = 8.3, 2.4 Hz), 6.04 (1H, dd, J = 11.2, 2.4 Hz), 5.21 (1H, d, J = 13.7 Hz), 4.84 (1H, d, J = 13.7 Hz), 4.66 (1H, d, J = 3.7 Hz), 4.52-4.40 (1H, m), 4.17-4.01 (2H, m), 3.80 (3H, s), 3.68 (1H, s), 3.55-3.41 (7H, m), 2.75-2.54 (2H, m), 2.06-1.81 (7H, m), 1.28 (3H, s), 0.91 (3H, s)

Compound 10-1

The compounds 10-2 and 10-3 were obtained by using the compound 9-1 and a commercially available compound in accordance with the producing process of the compound 10-1.

8-(5-fluoro-2-methylphenoxymethyl)-7-[4-[3-(N-morpholino)carbonyl-2-hydroxypropyl]oxy-2-methoxyphenyl]-1,3,3-trimethyl-3,4-dihydro-1H-quinoxalin-2-one (the compound 10-2)

TABLE 39

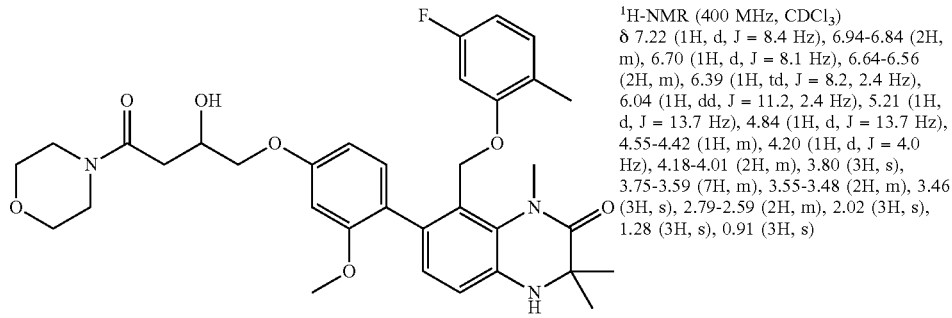

$^1$H-NMR (400 MHz, CDCl$_3$)
δ 7.22 (1H, d, J = 8.4 Hz), 6.94-6.84 (2H, m), 6.70 (1H, d, J = 8.1 Hz), 6.64-6.56 (2H, m), 6.39 (1H, td, J = 8.2, 2.4 Hz), 6.04 (1H, dd, J = 11.2, 2.4 Hz), 5.21 (1H, d, J = 13.7 Hz), 4.84 (1H, d, J = 13.7 Hz), 4.55-4.42 (1H, m), 4.20 (1H, d, J = 4.0 Hz), 4.18-4.01 (2H, m), 3.80 (3H, s), 3.75-3.59 (7H, m), 3.55-3.48 (2H, m), 3.46 (3H, s), 2.79-2.59 (2H, m), 2.02 (3H, s), 1.28 (3H, s), 0.91 (3H, s)

Compound 10-2

8-(5-fluoro-2-methylphenoxymethyl)-7-[4-[3-(N-piperidino)carbonyl-2-hydroxy-propyl]oxy-2-methoxyphenyl]-1,3,3-trimethyl-3,4-dihydro-1H-quinoxalin-2-one (the compound 10-3)

TABLE 40

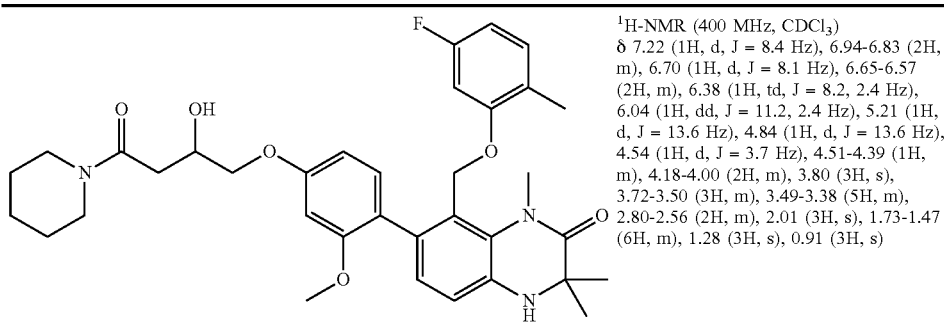

Compound 10-3

$^1$H-NMR (400 MHz, CDCl$_3$)
δ 7.22 (1H, d, J = 8.4 Hz), 6.94-6.83 (2H, m), 6.70 (1H, d, J = 8.1 Hz), 6.65-6.57 (2H, m), 6.38 (1H, td, J = 8.2, 2.4 Hz), 6.04 (1H, dd, J = 11.2, 2.4 Hz), 5.21 (1H, d, J = 13.6 Hz), 4.84 (1H, d, J = 13.6 Hz), 4.54 (1H, d, J = 3.7 Hz), 4.51-4.39 (1H, m), 4.18-4.00 (2H, m), 3.80 (3H, s), 3.72-3.50 (3H, m), 3.49-3.38 (5H, m), 2.80-2.56 (2H, m), 2.01 (3H, s), 1.73-1.47 (6H, m), 1.28 (3H, s), 0.91 (3H, s)

Example 11

(S)-7-[4-[2-(N,N-dimethylaminoacetoxy)propyl]oxy-2-methoxyphenyl]-8-(5-fluoro-2-methylphenoxymethyl)-1,3,3-trimethyl-3,4-dihydro-1H-quinoxalin-2-one (the compound 11-1)

To N,N-dimethylformamide-methylene chloride mixed solution (1:1, 12 mL) were added (S)-8-(5-fluoro-2-methylphenoxymethyl)-7-[4-(2-hydroxypropyl)oxy-2-methoxyphenyl]-1,3,3-trimethyl-3,4-dihydro-1H-quinoxalin-2-one (the compound 1-1, 509 mg, 1.00 mmol), N,N-dimethylglycine (207 mg, 2.01 mmol), 1-ethyl-3-(3-dimethylaminopropyl)carbodiimide hydrochloride (388 mg, 2.02 mmol) and 4-dimethylaminopyridine (10.6 mg, 0.087 mmol), and the mixture was stirred at 50° C. for 6 hours. After allowing to cool, the mixture was diluted with ethyl acetate (100 mL), and washed with a saturated aqueous sodium hydrogen carbonate solution (50 mL), an aqueous saturated ammonium chloride solution (50 mL) and a saturated saline solution (50 mL). The organic layer was concentrated under reduced pressure and the obtained residue was purified by silica gel column chromatography (hexane/ethyl acetate) to give the title compound (205 mg) as white amorphous (Yield: 35%).

8-(5-Fluoro-2-methylphenoxymethyl)-7-[4-[(2 S)-[(2 S)-pyrrolidylcarbonyloxy]-propyl]oxy-2-methoxyphenyl]-1,3,3-trimethyl-3,4-dihydro-1H-quinoxalin-2-one hydrochloride (the compound 11-2)

A mixture of (S)-8-(5-fluoro-2-methylphenoxymethyl)-7-[4-(2-hydroxy-propyl)oxy-2-methoxyphenyl]-1,3,3-trimethyl-3,4-dihydro-1H-quinoxalin-2-one (the compound 1-1, 306 mg, 0.60 mmol), N-t-butoxycarbonyl-L-proline (258 mg, 1.2 mmol), 1-ethyl-3-(3-dimethylaminopropyl)carbodiimide hydrochloride (234 mg, 1.2 mmol), 4-dimethylaminopyridine (9.9 mg, 0.081 mmol) and methylene chloride (6.0 mL) was stirred at room temperature overnight. The mixture was concentrated under reduced pressure, and the obtained residue was diluted by ethyl acetate (50 mL) and washed with water (50 mL). The organic layer was concentrated under reduced pressure and the obtained residue was puri-

TABLE 41

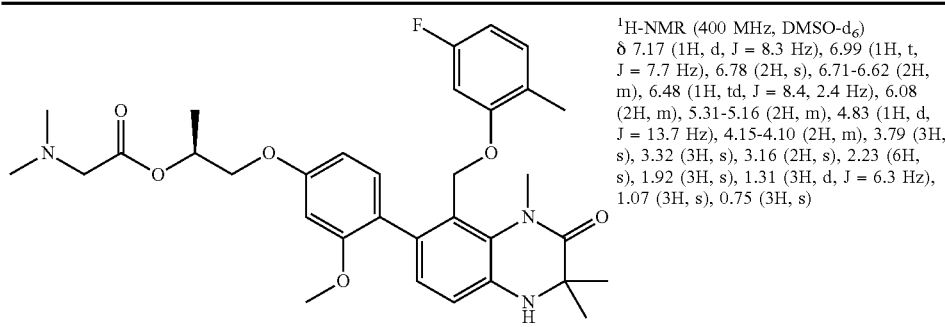

Compound 11-1

$^1$H-NMR (400 MHz, DMSO-d$_6$)
δ 7.17 (1H, d, J = 8.3 Hz), 6.99 (1H, t, J = 7.7 Hz), 6.78 (2H, s), 6.71-6.62 (2H, m), 6.48 (1H, td, J = 8.4, 2.4 Hz), 6.08 (2H, m), 5.31-5.16 (2H, m), 4.83 (1H, d, J = 13.7 Hz), 4.15-4.10 (2H, m), 3.79 (3H, s), 3.32 (3H, s), 3.16 (2H, s), 2.23 (6H, s), 1.92 (3H, s), 1.31 (3H, d, J = 6.3 Hz), 1.07 (3H, s), 0.75 (3H, s)

fied by silica gel column chromatography (hexane/ethyl acetate). A 4N hydrochloric acid-1,4-dioxane solution (8.0 mL) was added to the obtained intermediate (7-[4-[(2S)-[(S)-N-(t-butoxycarbonyl)pyrrolidin-2-ylcarbonyloxy]propyl]oxy-2-methoxyphenyl]-8-(5-fluoro-2-methylphenoxymethyl)-1,3,3-trimethyl-3,4-dihydro-1H-quinoxalin-2-one), and the resulting mixture was stirred at room temperature overnight. The mixture was concentrated under reduced pressure, and diethyl ether (10 mL) and ethyl acetate (10 mL) were added to the obtained residue. The precipitated solid was collected by filtration, and washed with ethyl acetate (10 mL). The obtained solid was dried under reduced pressure at 40° C. for 3.5 hours to give the title compound (284 mg) as a white solid (Yield: 74%).

TABLE 42

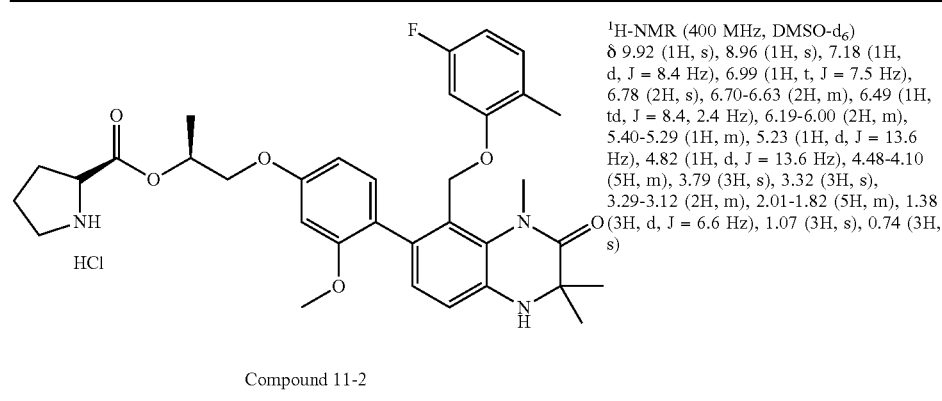

$^1$H-NMR (400 MHz, DMSO-d$_6$)
δ 9.92 (1H, s), 8.96 (1H, s), 7.18 (1H, d, J = 8.4 Hz), 6.99 (1H, t, J = 7.5 Hz), 6.78 (2H, s), 6.70-6.63 (2H, m), 6.49 (1H, td, J = 8.4, 2.4 Hz), 6.19-6.00 (2H, m), 5.40-5.29 (1H, m), 5.23 (1H, d, J = 13.6 Hz), 4.82 (1H, d, J = 13.6 Hz), 4.48-4.10 (5H, m), 3.79 (3H, s), 3.32 (3H, s), 3.29-3.12 (2H, m), 2.01-1.82 (5H, m), 1.38 (3H, d, J = 6.6 Hz), 1.07 (3H, s), 0.74 (3H, s)

Compound 11-2

The compounds 11-3 to 11-5 were obtained by using the compound 1-1 and a commercially available compound in accordance with the producing process of the compound 11-1 or 11-2.

(R)-7-[4-[2-(N,N-dimethylaminoacetoxy)propyl]oxy-2-methoxyphenyl]-8-(5-fluoro-2-methylphenoxymethyl)-1,3,3-trimethyl-3,4-dihydro-1H-quinoxalin-2-one (the compound 11-3)

TABLE 43

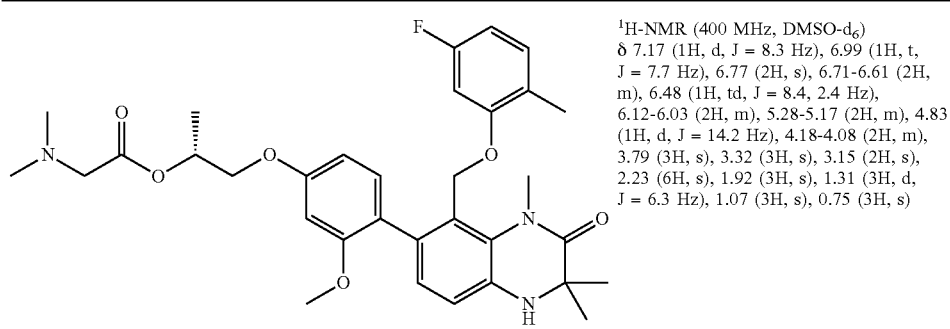

$^1$H-NMR (400 MHz, DMSO-d$_6$)
δ 7.17 (1H, d, J = 8.3 Hz), 6.99 (1H, t, J = 7.7 Hz), 6.77 (2H, s), 6.71-6.61 (2H, m), 6.48 (1H, td, J = 8.4, 2.4 Hz), 6.12-6.03 (2H, m), 5.28-5.17 (2H, m), 4.83 (1H, d, J = 14.2 Hz), 4.18-4.08 (2H, m), 3.79 (3H, s), 3.32 (3H, s), 3.15 (2H, s), 2.23 (6H, s), 1.92 (3H, s), 1.31 (3H, d, J = 6.3 Hz), 1.07 (3H, s), 0.75 (3H, s)

Compound 11-3

(S)-7-[4-(2-aminoacetoxypropyl)oxy-2-methoxyphenyl]-8-(5-fluoro-2-methylphenoxy-methyl)-1,3,3-trimethyl-3,4-dihydro-1H-quinoxalin-2-one hydrochloride (the compound 11-4)

TABLE 44

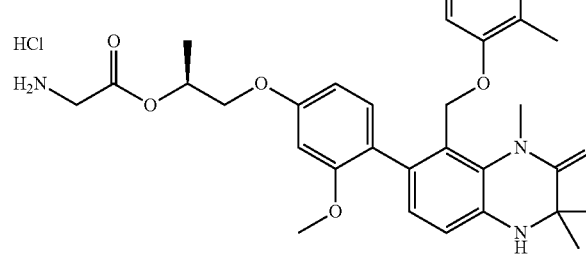

Compound 11-4

$^1$H-NMR (400 MHz, DMSO-d$_6$)
δ 8.33 (3H, s), 7.18 (1H, d, J = 8.3 Hz), 6.99 (1H, t, J = 7.7 Hz), 6.78 (2H, s), 6.71-6.63 (2H, m), 6.49 (1H, td, J = 8.4, 2.4 Hz), 6.17-6.01 (2H, m), 5.36-5.27 (1H, m), 5.22 (1H, d, J = 14.3 Hz), 4.81 (1H, d, J = 14.3 Hz), 4.22-4.11 (2H, m), 3.91-3.82 (2H, m), 3.80 (3H, s), 3.33 (3H, s), 1.92 (3H, s), 1.37 (3H, d, J = 6.3 Hz), 1.07 (3H, s), 0.75 (3H, s)

7-[4-[(2S)-[(2S)-amino-3-methylbutanoyloxy]propyl]oxy-2-methoxyphenyl]-8-(5-fluoro-2-methylphenoxymethyl)-1,3,3-trimethyl-3,4-dihydro-1H-quinoxalin-2-one hydrochloride (the compound 11-5)

TABLE 45

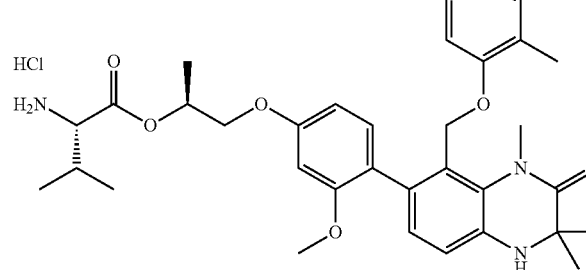

Compound 11-5

$^1$H-NMR (400 MHz, DMSO-d$_6$)
δ 8.46 (3H, s), 7.18 (1H, d, J = 9.0 Hz), 6.99 (1H, t, J = 7.7 Hz), 6.78 (2H, s), 6.68-6.59, (2H, m), 6.49 (1H, td, J = 8.5, 2.3 Hz), 6.18-6.01 (2H, m), 5.42-5.31 (1H, m), 5.22 (1H, d, J = 14.1 Hz), 4.81 (1H, d, J = 14.1 Hz), 4.29-4.20 (1H, m), 4.19-4.09 (1H, m), 3.98-3.89 (1H, m), 3.78 (3H, s), 3.32 (3H, s), 2.23-2.10 (1H, m), 1.92 (3H, s), 1.36 (3H, d, J = 6.6 Hz), 1.07 (3H, s), 1.02-0.92 (6H, m), 0.75 (3H, s)

Example 12

(S)-7-[4-[2-(3-carboxypropanoyloxy)propyl]oxy-2-methoxyphenyl]-8-(5-fluoro-2-methylphenoxymethyl)-1,3,3-trimethyl-3,4-dihydro-1H-quinoxalin-2-one (the compound 12-1)

A mixture of (S)-8-(5-fluoro-2-methylphenoxymethyl)-7-[4-(2-hydroxy-propyl)oxy-2-methoxyphenyl]-1,3,3-trimethyl-3,4-dihydro-1H-quinoxalin-2-one (the compound 1-1, 52 mg, 0.10 mmol), succinic anhydride (16 mg, 0.16 mmol), 4-dimethylaminopyridine (catalytic amount) and pyridine (0.5 mL) was stirred at room temperature overnight. Succinic anhydride (65 mg, 0.65 mmol) was additionally added and the mixture was further stirred overnight. The mixture was diluted with ethyl acetate (10 mL), and the organic layer was washed with 1N hydrochloric acid (15 mL×2) and a saturated saline solution (5 mL). The organic layer was dried over anhydrous magnesium sulfate, and filtered. The filtrate was concentrated under reduced pressure to give the title compound (58 mg) as white amorphous (quantitative).

TABLE 46

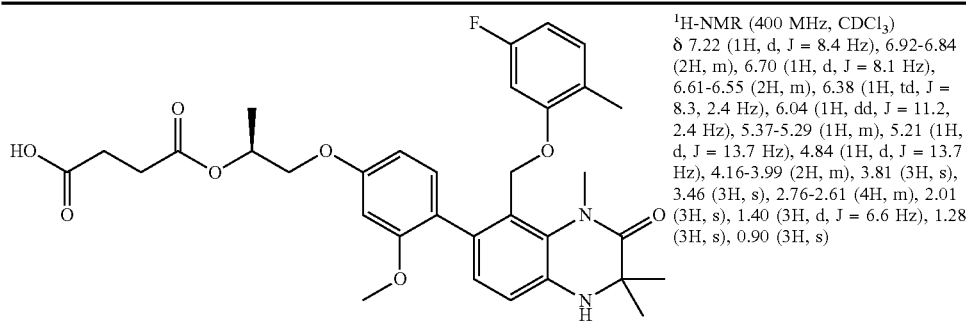

Compound 12-1

¹H-NMR (400 MHz, CDCl₃)
δ 7.22 (1H, d, J = 8.4 Hz), 6.92-6.84 (2H, m), 6.70 (1H, d, J = 8.1 Hz), 6.61-6.55 (2H, m), 6.38 (1H, td, J = 8.3, 2.4 Hz), 6.04 (1H, dd, J = 11.2, 2.4 Hz), 5.37-5.29 (1H, m), 5.21 (1H, d, J = 13.7 Hz), 4.84 (1H, d, J = 13.7 Hz), 4.16-3.99 (2H, m), 3.81 (3H, s), 3.46 (3H, s), 2.76-2.61 (4H, m), 2.01 (3H, s), 1.40 (3H, d, J = 6.6 Hz), 1.28 (3H, s), 0.90 (3H, s)

Example 13
(S)-7-[4-[2-(2,3-dihydroxypropanoyl)oxypropyl]oxy-2-methoxyphenyl]-8-(5-fluoro-2-methylphenoxymethyl)-1,3,3-trimethyl-3,4-dihydro-1H-quinoxalin-2-one (the compound 13-1)

A mixture of (S)-7-[4-[2-(2,2-dimethyl-1,3-dioxolan-4-ylcarbonyloxy)propyl]-oxy-2-methoxyphenyl]-8-(5-fluoro-2-methylphenoxymethyl)-1,3,3-trimethyl-3,4-dihydro-1H-quinoxalin-2-one (the Reference Compound 8-2, 70 mg, 0.11 mmol), 2N hydrochloric acid (1.0 mL) and methanol (4.0 mL) was stirred at 50° C. for 1 hour. After allowing to cool at room temperature, the mixture was concentrated under reduced pressure, and the obtained residue was purified by silica gel column chromatography (hexane/ethyl acetate) to give the title compound (35 mg) as a white solid (Yield: 54%)

TABLE 47

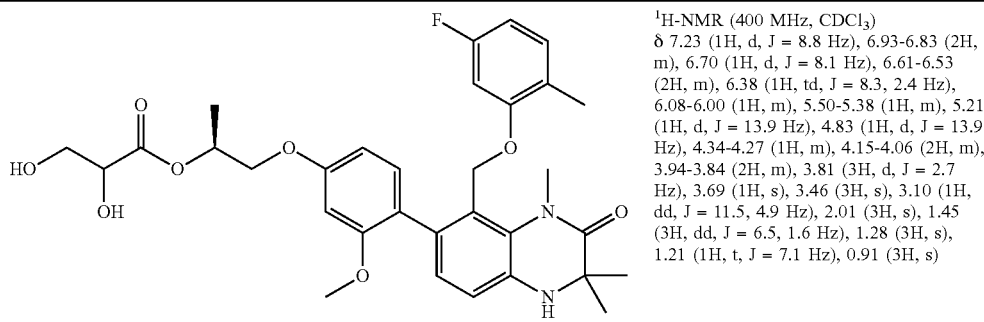

Compound 13-1

¹H-NMR (400 MHz, CDCl₃)
δ 7.23 (1H, d, J = 8.8 Hz), 6.93-6.83 (2H, m), 6.70 (1H, d, J = 8.1 Hz), 6.61-6.53 (2H, m), 6.38 (1H, td, J = 8.3, 2.4 Hz), 6.08-6.00 (1H, m), 5.50-5.38 (1H, m), 5.21 (1H, d, J = 13.9 Hz), 4.83 (1H, d, J = 13.9 Hz), 4.34-4.27 (1H, m), 4.15-4.06 (2H, m), 3.94-3.84 (2H, m), 3.81 (3H, d, J = 2.7 Hz), 3.69 (1H, s), 3.46 (3H, s), 3.10 (1H, dd, J = 11.5, 4.9 Hz), 2.01 (3H, s), 1.45 (3H, dd, J = 6.5, 1.6 Hz), 1.28 (3H, s), 1.21 (1H, t, J = 7.1 Hz), 0.91 (3H, s)

The compound 13-2 was obtained by using the reference compound 8-3 in accordance with the producing process of the compound 13-1.

7-[4-[(2S)-[(2S)-amino-3-hydroxypropanoyloxy]propyl]oxy-2-methoxyphenyl]-8-(5-fluoro-2-methylphenoxymethyl)-1,3,3-trimethyl-3,4-dihydro-1H-quinoxalin-2-one (the compound 13-2)

TABLE 48

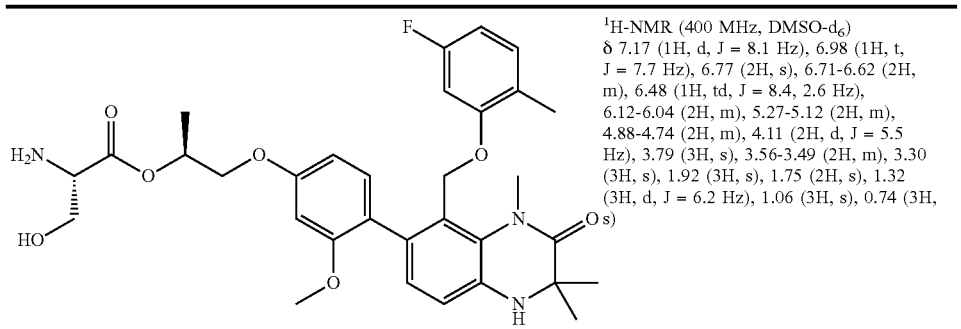

Compound 13-2

¹H-NMR (400 MHz, DMSO-d₆)
δ 7.17 (1H, d, J = 8.1 Hz), 6.98 (1H, t, J = 7.7 Hz), 6.77 (2H, s), 6.71-6.62 (2H, m), 6.48 (1H, td, J = 8.4, 2.6 Hz), 6.12-6.04 (2H, m), 5.27-5.12 (2H, m), 4.88-4.74 (2H, m), 4.11 (2H, d, J = 5.5 Hz), 3.79 (3H, s), 3.56-3.49 (2H, m), 3.30 (3H, s), 1.92 (3H, s), 1.75 (2H, s), 1.32 (3H, d, J = 6.2 Hz), 1.06 (3H, s), 0.74 (3H, s)

Example 14

(S)-8-(5-fluoro-2-methylphenoxymethyl)-7-[4-(2-phosphonohydroxypropyl)oxy-2-methoxyphenyl]-1,3,3-trimethyl-3,4-dihydro-1H-quinoxalin-2-one (the compound 14-1)

Under ice-cooling, a methylene chloride (3.0 mL) solution of m-chloro-perbenzoic acid (41 mg, 0.24 mmol) was added dropwise to an N,N-dimethylformamide (3.0 mL) solution of (S)-8-(5-fluoro-2-methylphenoxymethyl)-7-[4-(2-hydroxypropyl)-oxy-2-methoxyphenyl]-1,3,3-trimethyl-3,4-dihydro-1H-quinoxalin-2-one (the compound 1-1, 100 mg, 0.20 mmol), 1H-tetrazole (62 mg, 0.89 mmol) and di-t-butoxy(diisopropylamino)phosphine (0.19 mL, 0.60 mmol), and the mixture was stirred for 1 hour. To the mixture were added a saturated aqueous sodium hydrogen carbonate solution (5 mL) and water (50 mL), and the resulting mixture was extracted with ethyl acetate (50 mL×2). The organic layers were combined, washed with a saturated saline solution (50 mL), dried over anhydrous sodium sulfate, and filtered. The filtrate was concentrated under reduced pressure and the obtained residue was purified by silica gel column chromatography (hexane/ethyl acetate). The obtained intermediate ((S)-7-[4-[2-(di-t-butylphosphonohydroxy)propyl]oxy-2-methoxyphenyl]-8-(5-fluoro-2-methylphenoxymethyl)-1,3,3-trimethyl-3,4-dihydro-1H-quinoxalin-2-one) was dissolved in anhydrous methylene chloride (1 mL). Under ice-cooling, trifluoroacetic acid (1 mL) was added to the solution, and the resulting mixture was stirred at room temperature for 30 minutes. The mixture was concentrated under reduced pressure, and hexane-diethyl ether (1:1, 2 mL) was added to the obtained residue. The precipitated solid was collected by filtration, and washed with hexane-diethyl ether (1:1, 5 mL). The obtained solid was dried to give the title compound (49 mg) as a white solid (Yield: 42%).

TABLE 49

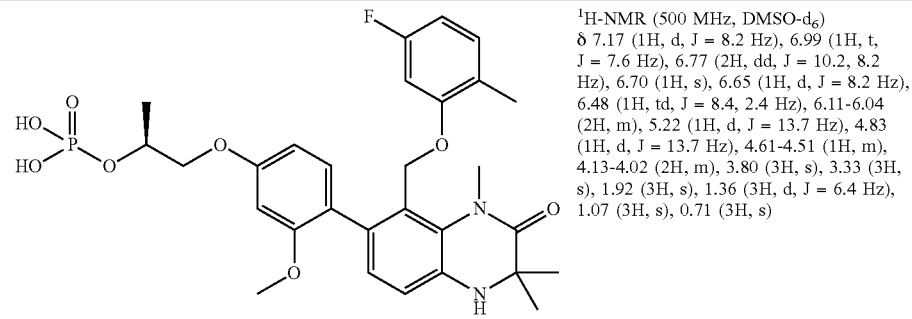

$^1$H-NMR (500 MHz, DMSO-$d_6$)
δ 7.17 (1H, d, J = 8.2 Hz), 6.99 (1H, t, J = 7.6 Hz), 6.77 (2H, dd, J = 10.2, 8.2 Hz), 6.70 (1H, s), 6.65 (1H, d, J = 8.2 Hz), 6.48 (1H, td, J = 8.4, 2.4 Hz), 6.11-6.04 (2H, m), 5.22 (1H, d, J = 13.7 Hz), 4.83 (1H, d, J = 13.7 Hz), 4.61-4.51 (1H, m), 4.13-4.02 (2H, m), 3.80 (3H, s), 3.33 (3H, s), 1.92 (3H, s), 1.36 (3H, d, J = 6.4 Hz), 1.07 (3H, s), 0.71 (3H, s)

Compound 14-1

The compounds 14-2 and 14-3 were obtained by using the compounds 1-5, 5-2 and a commercially available compound in accordance with the producing process of the compound 14-1.

(S)-8-(5-fluoro-2-methylphenoxymethyl)-7-[4-(2-phosphonohydroxybutyl)oxy-2-methoxyphenyl]-1,3,3-trimethyl-3,4-dihydro-1H-quinoxalin-2-one (the compound 14-2)

TABLE 50

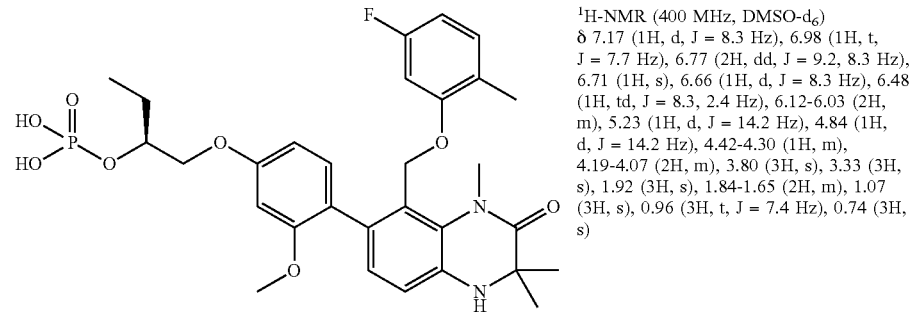

$^1$H-NMR (400 MHz, DMSO-$d_6$)
δ 7.17 (1H, d, J = 8.3 Hz), 6.98 (1H, t, J = 7.7 Hz), 6.77 (2H, dd, J = 9.2, 8.3 Hz), 6.71 (1H, s), 6.66 (1H, d, J = 8.3 Hz), 6.48 (1H, td, J = 8.3, 2.4 Hz), 6.12-6.03 (2H, m), 5.23 (1H, d, J = 14.2 Hz), 4.84 (1H, d, J = 14.2 Hz), 4.42-4.30 (1H, m), 4.19-4.07 (2H, m), 3.80 (3H, s), 3.33 (3H, s), 1.92 (3H, s), 1.84-1.65 (2H, m), 1.07 (3H, s), 0.96 (3H, t, J = 7.4 Hz), 0.74 (3H, s)

Compound 14-2

(S)-7-[4-(3-cyano-2-phosphonohydroxypropyl)oxy-2-methoxyphenyl]-8-(5-fluoro-2-methylphenoxymethyl)-1,3,3-trimethyl-3,4-dihydro-1H-quinoxalin-2-one (the compound 14-3)

TABLE 51

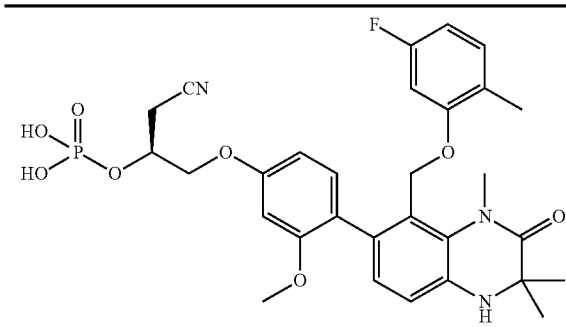

¹H-NMR (400 MHz, DMSO-d₆)
δ 7.22-7.12 (1H, m), 7.02-6.93 (1H, m), 6.81-6.65 (4H, m), 6.48 (1H, td, J = 8.2, 2.1 Hz), 6.13-6.03 (2H, m), 5.22 (1H, d, J = 13.4 Hz), 4.91-4.59 (2H, m), 4.29-4.17 (2H, m), 3.80 (3H, s), 3.33 (3H, s), 3.08-3.03 (2H, m), 1.92 (3H, s), 1.07 (3H, s), 0.75 (3H, s)

Compound 14-3

[Pharmacological Test]

For carrying out Pharmacological Test, the control compound B, the control compound C, the control compound D, the control compound E and the control compound F were prepared in accordance with the above-mentioned Patent Document 2 (JP 2008-74829A) for comparison with the effect of the present compound, and used in the test.

The control compound B is 8-(5-fluoro-2-methylphenoxymethyl)-7-(5-hydroxymethyl-2-methoxyphenyl)-1,3,3-trimethyl-3,4-dihydro-1H-quinoxalin-2-one having the following structure:

[Formula 12]

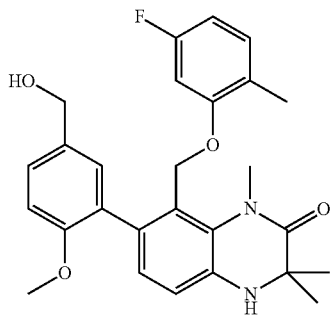

The control compound C is 8-(5-fluoro-2-methylphenoxymethyl)-7-(5-hydroxy-2-methoxyphenyl)-1,3,3-trimethyl-3,4-dihydro-1H-quinoxalin-2-one having the following structure:

[Formula 13]

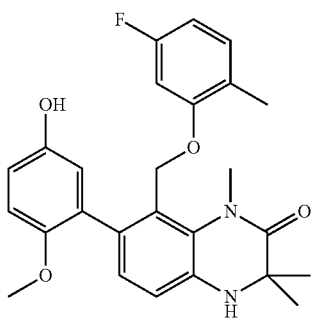

The control compound D is 7-(4-butyryloxy-2-methoxyphenyl)-8-(5-fluoro-2-methylphenoxymethyl)-1,3,3-trimethyl-3,4-dihydro-1H-quinoxalin-2-one having the following structure:

[Formula 14]

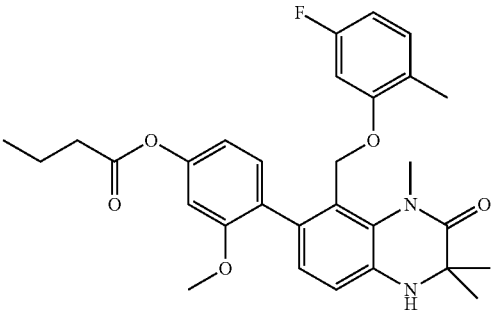 [SMILES: CC[C@H](O)COc1ccc(-c2ccc3c(c2COc2cc(F)ccc2C)N(C)C(=O)C(C)(C)N3)c(OC)c1]

The control compound E is 7-(2,4-dimethoxyphenyl)-8-(5-fluoro-2-methyl-phenoxymethyl)-1,3,3-trimethyl-3,4-dihydro-1H-quinoxalin-2-one having the following structure:

[Formula 15]

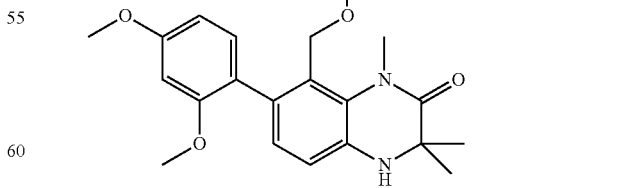

The control compound F is 8-(5-fluoro-2-methylphenoxymethyl)-7-(2-methoxy-4-methoxymethoxyphenyl)-1,3,3-trimethyl-3,4-dihydro-1H-quinoxalin-2-one having the following structure:

[Formula 16]

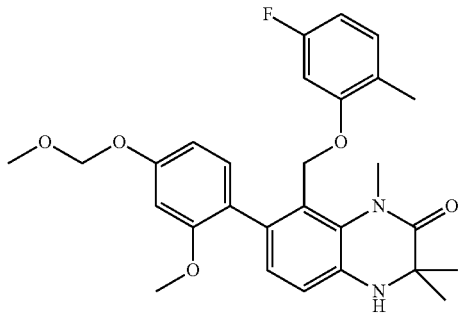

[Pharmacological Test]
1. GR Binding Activity Evaluation Test

In order to evaluate a binding activity of the present compound to GR, a GR receptor competitor assay was carried out by a fluorescence polarization method. In the assay, a GR competitive binding assay kit (manufactured by Invitrogen, cat No. P2816) was used for the assay, and a procedure was carried out according to the protocol attached to the kit. Hereinafter, the specific method will be described.
(Preparation of Reagents)

GR screening buffer: A buffer containing 10 mM of potassium phosphate (pH 7.4), 20 mM of sodium molybdate ($Na_2MoO_4$), 0.1 mM of ethylene diamine tetraacetic acid (EDTA), 5 mM of dithiothreitol (DTT), 0.1 mM of stabilizing peptide and 2% of dimethylsulfoxide was prepared.

4×GS1 solution: Fluormone™ GS1, which is a fluorescent glucocorticoid ligand, was diluted with GR screening buffer, whereby a 4 nM solution was prepared.

4×GR solution: Recombinant human GR was diluted with GR screening buffer, whereby a 16 nM solution was prepared.
(Preparation of Test Compound Solution and Dexamethasone (Hereinafter Also Referred to as "DEX".) Solution)

After a test compound was dissolved in dimethylsulfoxide, the resulting solution was diluted with GR screening buffer, whereby a 20 µM test compound solution was prepared. In addition, DEX was similarly dissolved, whereby a DEX solution with a 200 µM concentration was prepared, and the solution was diluted with GR screening buffer, whereby a 2 mM DEX solution was prepared. DEX was used as positive control.
(Test Method and Measurement Method)
1) The test compound solution was added in an amount of 10 µL into each well of a 384-well plate.
2) 4×GS1 solution and 4×GR solution were added in an amount of 5 µL into each well, respectively.
3) GR screening buffer was added in an amount of 10 µL/well into each well in place of the test compound solution, which was made a negative control.
4) A 2 mM of DEX was added in an amount of 10 µL/well into each well in place of the test compound solution, which was made a positive control.
5) The plate was incubated in a dark place at room temperature for 2 hours, and fluorescence polarization of each well was measured.
(Calculation Equation of GR Binding Ratio)

A GR binding ratio (%) was calculated from the following equation.

GR binding ratio (%)=100×{1−(fluorescence polarization of test compound solution−average value of fluorescence polarization of positive control solution)/(average value of fluorescence polarization of negative control solution−average value of fluorescence polarization of positive control solution)}

(Test Results and Discussion)

The GR binding rates (%) when the compound 1-1, the compound 1-3, the compound 1-4, the compound 1-6, the compound 2-1, the compound 2-2, the compound 3-1, the compound 4-1, the compound 4-2, the compound 4-3, the compound 5-1, the compound 5-2, the compound 7-1, the compound 7-2, the compound 9-1, the compound 10-1, the compound 10-2, the compound 10-3, the compound 11-1, the compound 11-5, the compound 14-1, the control compound B, the control compound C, the control compound D, the control compound E and the control compound F were used as the test compound are shown in Table I.

As a result of the GR binding activity evaluation test, the present compounds showed an excellent GR binding activity.

TABLE I

[Table 52]

| Test compound | GR binding rate (%) | Test compound | GR binding rate (%) |
|---|---|---|---|
| Compound 1-1 | >99 | Compound 7-2 | >99 |
| Compound 1-3 | 95 | Compound 9-1 | >99 |
| Compound 1-4 | >99 | Compound 10-1 | 94 |
| Compound 1-6 | 87 | Compound 10-2 | >99 |
| Compound 2-1 | >99 | Compound 10-3 | >99 |
| Compound 2-2 | 91 | Compound 11-1 | 99 |
| Compound 3-1 | >99 | Compound 11-5 | >99 |
| Compound 4-1 | >99 | Compound 14-1 | >99 |
| Compound 4-2 | >99 | Control compound B | >99 |
| Compound 4-3 | 88 | Control compound C | >99 |
| Compound 5-1 | 88 | Control compound D | 98 |
| Compound 5-2 | >99 | Control compound E | 98 |
| Compound 7-1 | >99 | Control compound F | 94 |

2. IL-6 Production Inhibitory Action Evaluation Test

To evaluate the action of the present compounds as a GR agonist, IL-6 production inhibitory action in human corneal epithelial cell line after LPS stimulation was examined The IL-6 production was measured by using the HTRF method (Cat No. 62IL6PEB manufactured by Cisbio Bioassays, Inc.) according to the attached protocol. The specific method is described below.
(Preparation of Reagent)

LPS solution: After dissolving LPS in PBS(−), the resulting solution was diluted with a culture solution, whereby an LPS solution with a 1 µg/mL concentration was prepared.
(Preparation of Test Compound Solution and DEX Solution)

After dissolving the test compound in dimethylsulfoxide, the solution was diluted with a 10% FBS-DMEM/Ham's F12 medium, whereby a 100 µM of the test compound solution was prepared. When the $IC_{50}$ value is to be calculated, the 100 µM solution was diluted with a 1% dimethylsulfoxide-containing 10% FBS-DMEM/Ham's F12 medium, whereby 10 µM, 3 µM, 1 µM, 0.3 µM, 0.1 µM and 0.01 µM of the test compound solutions were prepared, respectively. In addition, DEX was similarly dissolved, whereby a 100 µM concentration of the DEX solution was prepared, and an IL-6 production inhibitory ratio of DEX was measured, and used for calculation of Efficacy (% DEX).
(Used Cells and Culturing Method)

Used cells: human corneal epithelium cell line (HCE-T) (RIKEN, Institute of Physical and Chemical Research)
Culturing Method
1) HCE-T proliferated to a subconfluent state was washed with PBS(−), and the cells were detached by the trypsin-EDTA treatment.

2) SHEM medium (supplemented hormone epithelial medium: 15% FBS, 5 μg/mL of insulin, 10 ng/mL of human EGF, and 40 μg/mL of gentamicin-containing DMEM/Ham's F12) was added and trypsin was inactivated.
3) The above suspension was recovered, and centrifuged by 1,000 rpm for 5 minutes to give a cell sediment.
4) The cell sediment was suspended by an SHEM medium, seeded in a culture flask, and cultured in a $CO_2$ incubator (temperature: 37° C., $CO_2$ concentration: 5%). The cells continued to subculture according to this method were used for the test.

(Test Method and Measurement Method)
1) The subcultured HCE-T was recovered and the cells were seeded at $2.0\times10^4$ cells/0.1 mL/well in a 96-well flat bottom culture plate.
2) After culturing overnight, medium the medium was removed and each 80 μL/well of 10% FBS-DMEM/Ham's F12 medium was added.
3) Test compound solution was added with each 10 μL/well.
4) LPS solution was added with each 10 μL/well.
5) The sample to which 1% dimethylsulfoxide-containing 10% FBS-DMEM/Ham's F12 medium was added with each 10 μL/well in place of each test compound solution, and 10% FBS-DMEM/Ham's F12 medium was added in place of the LPS solution was made a negative control.
6) The sample in which 1% dimethylsulfoxide-containing 10% FBS-DMEM/Ham's F12 medium was added with each 10 μL/well in place of each test compound solution was made a positive control.
7) After completion of 4 hours cultivation, the supernatant was recovered and the amount of IL-6 released in the supernatant was measured by using an HTRF human IL-6 Kit.
8) The IL-6 production inhibitory ratio was calculated according to the following calculation formula.

(Calculation of IL-6 Production Inhibitory Ratio)
The IL-6 production inhibitory ratio (%) was calculated by the following formula.

IL-6 production inhibitory ratio (%)=100×{1−(IL-6 produced amount of each test compound solution−average value of IL-6 produced amount of negative control group)/(average value of IL-6 produced amount of positive control group−average value of IL-6 produced amount of negative control group)}(%)

Further, the IL-6 production inhibitory ratio (Efficacy (% DEX)) when the DEX treated group was made 100 was calculated.

Efficacy (% DEX)=100×{(average value of IL-6 production inhibitory ratio of each test compound solution)/(average value of IL-6 production inhibitory ratio of DEX treated group)}(%)

In addition, $IC_{50}$ was calculated according to a conventional method. IDBS XLfit4 was used for the calculation.

(Test Result and Consideration)
The IL-6 production inhibitory ratio (% DEX) and $IC_{50}$ (μM) when the compound 1-1, the compound 1-4, the compound 1-6, the compound 2-1, the compound 5-1, the compound 5-2, the compound 7-2, the compound 11-4, the compound 11-5, the control compound B, the control compound C, the control compound D, the control compound E and the control compound F were used as the test compounds are shown in Table II.

As a result of the IL-6 production inhibitory action evaluation test, the present compounds showed an excellent IL-6 production inhibitory action.

TABLE II

[Table 53]

| Test compound | IL-6 production inhibitory ratio (% DEX) | IC50 (μM) |
|---|---|---|
| Compound 1-1 | 86 | 0.033 |
| Compound 1-4 | 92 | 0.034 |
| Compound 1-6 | 89 | <0.001 |
| Compound 2-1 | 82 | 0.015 |
| Compound 5-1 | 98 | 0.014 |
| Compound 5-2 | >99 | 0.013 |
| Compound 7-2 | >99 | 0.083 |
| Compound 11-4 | 94 | Not measured |
| Compound 11-5 | 94 | Not measured |
| Control compound B | 62 | 0.123 |
| Control compound C | 71 | 0.093 |
| Control compound D | 69 | Not measured |
| Control compound E | 10 | Not measured |
| Control compound F | 62 | Not measured |

3. TNFα Production Inhibitory Action Evaluation Test

In order to evaluate an action of the present compound as a GR agonist, a TNFα production inhibitory action in rat whole blood after LPS stimulation ex vivo was investigated. For the measurement of the TNFα production amount, the ELISA method (manufactured by R&D Systems, Cat No. RTA00) was used, and a procedure was carried out according to the protocol attached thereto. Hereinafter, the specific method will be described.

(Preparation of Reagent)
LPS solution: LPS was dissolved in PBS(−) and diluted with RPMI 1640 to prepare an LPS solution with a concentration of 2 μg/mL.

(Preparation of Test Compound Solution and DEX Solution)
After the test compound was dissolved in dimethylsulfoxide, the solution was diluted with PBS(−) to prepare 200 μM of a test compound solution. In addition, DEX was similarly dissolved to prepare 200 μM of a DEX solution, and a TNFα production inhibitory ratio of DEX was measured, and used for calculation of Efficacy (% DEX).

(Test Method and Measurement Method)
1) Blood was collected from 3 to 5 rats using an injection syringe treated with heparin from the abdominal aorta under isoflurane anesthesia. The rats confirmed death after lething the whole blood.
2) The blood of 3 to 5 rats pooled in a 96-well round bottom culture plate was seeded at each 180 μL/well.
3) It was cultured (37° C., 5% $CO_2$, 95% air) for about 1 hour.
4) The test compound solution was added each 10 μL/well, and cultured for 1 hour.
5) LPS solution was added each 10 μL/well.
6) The sample in which 2% dimethylsulfoxide-containing PBS(−) was added with each 10 μL/well in place of each test compound solution, and RPMI 1640 was added with each 10 μL/well in place of the LPS solution was made a negative control.
7) The sample in which 2% dimethylsulfoxide-containing PBS(−) was added with each 10 μL/well in place of each test compound solution was made a positive control.
8) After completion of 20 hours cultivation, the supernatant was recovered and the amount of TNFα released in the supernatant was measured by using an ELISA Kit.
9) The TNFα production inhibitory ratio was calculated according to the following calculation formula.

(Calculation of TNFα Production Inhibitory Ratio)

TNFα production inhibitory ratio (%) was calculated according to the following formula.

TNFα production inhibitory ratio (%)=100×{1−(TNFα production amount of each test compound solution−average value of TNFα production amount of negative control group)/(average value of TNFα production amount of positive control group−average value of TNFα production amount of negative control group)}(%)

Further, a TNFα production inhibitory ratio (Efficacy (% DEX)) when the DEX treated group was made 100 was calculated.

Efficacy (% DEX)=100×{(average value of TNFα production inhibitory ratio of each test compound solution)/(average value of TNFα production inhibitory ratio of DEX treated group)} (%)

(Test Result and Consideration)

The TNFα production inhibitory ratios (Efficacy (% DEX)) when the compound 1-1, the compound 1-2, the compound 1-3, the compound 1-4, the compound 2-1, the compound 2-2, the compound 5-2, the compound 10-2, the compound 14-1, the control compound B, the control compound E and the control compound F were used as the test compound are shown in Table III.

As a result of the TNFα production inhibitory action evaluation test, the present compounds showed excellent TNFα production inhibitory action.

TABLE III

[Table 54]

| Test compound | TNFα production inhibitory ratio (% DEX) |
|---|---|
| Compound 1-1 | 81 |
| Compound 1-2 | 94 |
| Compound 1-3 | 93 |
| Compound 1-4 | 94 |
| Compound 2-1 | 97 |
| Compound 2-2 | 95 |
| Compound 5-2 | >99 |
| Compound 10-2 | >99 |
| Compound 14-1 | 86 |
| Control compound B | 77 |
| Control compound E | 0 |
| Control compound F | 69 |

4. IL-2 and IL-4 Production Inhibitory Actions Evaluation Test

In order to evaluate an action of the present compound as a GR agonist, IL-2 and IL-4 production inhibitory actions in a normal human CD4$^+$T cell after stimulation by an anti-CD3/CD28 antibody were investigated. For the measurement of the IL-2 and IL-4 production amounts, the ELISA method (manufactured by R&D Systems, Cat No. D2050, HS400) was used, and a procedure was carried out according to the protocol attached thereto. Hereinafter, the specific method will be described.

(Preparation of Reagent)

Dynabeads (Registered Trademark) Human T-Activator CD3/CD28 ($4 \times 10^7$ beads/mL) (Dynabeads) was used, and prepared according to the protocol attached thereto.

(Preparation of Test Compound Solution)

After the test compound was dissolved in dimethylsulfoxide, the solution was diluted with an RPMI medium to prepare 400 μM of a test compound solution. The solution was diluted with a 4% dimethylsulfoxide-containing RPMI medium to prepare 40 μM of a test compound solution.

(Used Cells and Culturing Method)

Used cells: normal peripheral blood human CD4$^+$T cell (human CD4$^+$T cell) (Lonza) Culturing method:

1) Frozen human CD4$^+$T cells were thawed in a warm water bath at 37° C., and added to an RPMI medium (RPMI 1640 containing 10% FBS, 100 U/mL of Penicillin, and 100 μg/mL of Streptomycin).
2) The above suspension was recovered and centrifuged at 900 rpm for 10 minutes to give a cell sediment.
3) The cell sediment was suspended in an RPMI medium and the operation of 2) was carried out.
4) The cell sediment was adjusted to $4 \times 10^5$ cells/mL with an RPMI medium.
5) The above suspension was cultured in a $CO_2$ incubator (temperature: 37° C., $CO_2$ concentration: 5%) for 1 hour or longer.

(Test Method and Measurement Method)

1) The cultured human CD4$^+$T cells were recovered and the cells were seeded in 96-well flat bottom culture plates at each $8.0 \times 10^4$ cells/0.2 mL/well.
2) The test compound solution was added with each 5 μL/well.
3) The prepared Dynabeads were added with each 2 μL/well.
4) The sample in which 4% dimethylsulfoxide-containing RPMI medium was added with each 5 μL/well in place of each test compound solution, and the RPMI medium was added with each 2 μL/well in place of the Dynabeads was made a negative control.
5) The sample in which 4% dimethylsulfoxide-containing RPMI medium was added with each 5 μL/well in place of each test compound solution was made a positive control.
6) After completion of 24 hours cultivation, the supernatant was recovered and the amounts of IL-2 and IL-4 released in the supernatant was measured by using an ELISA Kit.
7) The IL-2 and IL-4 production inhibitory ratios were calculated according to the following calculation formula.

(Calculation of IL-2 and IL-4 Production Inhibitory Ratios)

The IL-2 and IL-4 production inhibitory ratios (%) were calculated by the following formula, respectively.

IL-2 or IL-4 production inhibitory ratio (%)=100×{1−(IL-2 or IL-4 production amounts of each test compound solution−average value of IL-2 or IL-4 production amount of negative control group)/(average value of IL-2 or IL-4 production amount of positive control group−average value of IL-2 or IL-4 production amount of negative control group)}(%)

(Test Result and Consideration)

The IL-2 and IL-4 production inhibitory ratios (% of 1 μM) when the compound 1-1, the compound 2-1, the compound 11-1, the control compound B, the control compound C, the control compound D, the control compound E and the control compound F were used as the test compounds are shown in Table IV.

As a result of the IL-2 and IL-4 production inhibitory action evaluation test, the present compounds showed excellent IL-2 and IL-4 production inhibitory actions.

TABLE IV

[Table 55]

| Test compound | IL-2 production inhibitory ratio (% of 1 μM) | IL-4 production inhibitory ratio (% of 1 μM) |
|---|---|---|
| Compound 1-1 | 73 | 91 |
| Compound 2-1 | 79 | 83 |

TABLE IV-continued

[Table 55]

| Test compound | IL-2 production inhibitory ratio (% of 1 μM) | IL-4 production inhibitory ratio (% of 1 μM) |
|---|---|---|
| Compound 11-1 | 72 | 87 |
| Control compound B | 35 | 51 |
| Control compound C | 26 | 56 |
| Control compound D | <0 | 46 |
| Control compound E | <0 | 32 |
| Control compound F | <0 | 29 |

5. MCP-1 Production Inhibitory Action Evaluation Test

In order to evaluate an action of the present compound as a GR agonist, an MCP-1 production inhibitory action in human monocyte cell after stimulation by LPS was investigated. For the measurement of the MCP-1 production amount in the sample, the ELISA method (manufactured by R&D Systems, Cat No. DCPOO) was used, and a procedure was carried out according to the protocol attached thereto. Hereinafter, the specific method will be described.

(Preparation of Reagent)

LPS solution: After LPS was dissolved in PBS(-), the solution was diluted with 10% FBS-containing RPMI 1640 to prepare an LPS solution with a 40 μg/mL concentration.

(Preparation of Test Compound Solution)

After the test compound was dissolved in dimethylsulfoxide, the solution was diluted with an RPMI medium to prepare 400 μM of a test compound solution. The solution was diluted with a 4% dimethylsulfoxide-containing RPMI 1640 medium to prepare 40 μM of a test compound solution.

(Used Cells and Culturing Method)

Used cells: human monocyte cell (THP-1) (ATCC)
Culturing Method
1) Subcultured THP-1 was recovered and centrifuged at 1,100 rpm for 5 minutes to give a cell sediment.
2) An RPMI medium (RPMI 1640 containing 10% FBS, 100 U/mL of penicillin, 100 μg/mL of streptomycin, 55 μM of 2-Mercaptoethanol, 10 ng/mL of human EGF, and 40 μg/mL of gentamicin) was added.
3) The above suspension was seeded in a culture flask and cultured in a $CO_2$ incubator (temperature: 37° C., $CO_2$ concentration: 5%). The cells continued to subculture according to this method were used for the test.

(Test Method and Measurement Method)
1) The subcultured THP-1 was recovered and the cells were each seeded at $1.9 \times 10^5$ cells/0.19 mL/well in a 96-well round bottom culture plate.
2) The test compound solution was added with each 5 μL/well and cultured for 2 hours.
3) LPS solution was added with each 5 μL/well.
4) The sample to which 4% dimethylsulfoxide-containing RPMI medium was added with each 5 μL/well in place of each test compound solution, and 10% FBS-RPMI 1640 was added with each 5 μL/well in place of the LPS solution was made a negative control.
5) The sample to 4% dimethylsulfoxide-containing RPMI medium was added with each 5 μL/well in place of each test compound solution was made a positive control.
6) After completion of 18 hours cultivation, the supernatant was recovered and the amount of MCP-1 released in the supernatant was measured by using an ELISA Kit.
7) The MCP-1 production inhibitory ratio was calculated according to the following calculation formula.

(Calculation of MCP-1 Production Inhibitory Ratio)

MCP-1 production inhibitory ratio (%) was calculated by the following formula.

MCP-1 production inhibitory ratio (%)=100×{1−(MCP-1 production amount of each test compound solution−average value of MCP-1 production amount of negative control group)/(average value of MCP-1 production amount of positive control group−average value of MCP-1 production amount of negative control group)} (%)

(Test Result and Consideration)

The MCP-1 production inhibitory ratios (% of 1 μM) when the compound 1-1, the compound 2-1, the compound 11-1, the control compound B, the control compound C, the control compound E and the control compound F were used as the test compounds are shown in Table V.

As a result of the MCP-1 production inhibitory action evaluation test, the present compounds showed an excellent MCP-1 production inhibitory action.

TABLE V

[Table 56]

| Test compound | MCP-1 production inhibitory ratio (% of 1 μM) |
|---|---|
| Compound 1-1 | 86 |
| Compound 2-1 | 91 |
| Compound 11-1 | 88 |
| Control compound B | 65 |
| Control compound C | 65 |
| Control compound E | 40 |
| Control compound F | 27 |

From the above results, the present compounds are confirmed to be useful as a GR agonist than the control compounds, and to be useful as a disease to which the GR agonist such as a steroid is effective, in particular, as a prophylactic or therapeutic agent for inflammatory diseases (bone and joint diseases, ocular inflammatory diseases, or the like).

6. Conjunctivitis Model Evaluation Test

In order to evaluate an anti-inflammatory action of the present compound to conjunctivitis, an inhibitory effect on edema formation in a carrageenin-caused conjunctivitis model of rats was investigated. Incidentally, this effect was evaluated by calculating an edema formation inhibitory ratio from a weight of the edema in a base agent administered group (control group) and a weight of the edema in the test compound administered group.

(Preparation of Eye Drop Solution of Test Compound)

A base agent containing a general additive(s) was added to the test compound to prepare test compound suspensions with 0.001% (W/V), 0.003% (W/V), 0.01% (W/V) and 1% (W/V).

(Preparation of Carrageenin-Caused Conjunctivitis Model and Evaluation Method)

By using male Wistar/ST rats, a urethane solution was administered and general anesthesia was applied, then a physiological saline solution in which 1.0% (W/V) of carrageenan had been dissolved was injected into the upper palpebral conjunctiva with both eyes each in an amount of 50 μL/eye to induce inflammation.

The compound 1-1 was once eye dropped (instillation dose: 5 μL/time) to both eyes 30 minutes before induction. In the base agent administered group (control group), the base agent was similarly eye dropped. The control compounds B and C were eye dropped (instillation dose: 5

μL/time) five times in total from 1 hour before induction to 3 hours after induction with an interval of 1 hour. In the base agent administered group (control group), the base agent was similarly eye dropped.

Four hours after induction, rats under general anesthesia were sacrificed by decapitation method, conjunctival edema areas of both eyes were removed, and the weight of each was measured. The edema formation inhibitory ratio was calculated from the average value of the weight of the edema.
(Calculation of Inhibitory Ratio)

Based on the average value of the weight of the edema of the base agent administered group (control group), the edema formation inhibitory ratio of the test compound suspension eye drop group was calculated by the following calculation formula.

Edema formation inhibitory ratio (%)=100×{1−(average value of the weight of the edema in the test compound eye drop group)/(average value of the weight of the edema in the base agent administered group (control group))}(%)

(Test Result and Consideration)

The edema formation inhibitory ratios (%) when the compound 1-1, the control compound B, the control compound C, commercially available drug A (active ingredient: 0.5% loteprednol etabonate) and commercially available drug B (active ingredient: 0.1% fluorometholone) which are existing ophthalmic solutions were used as the test compounds are shown in Table VI. The average value of the weight of the edema is each 8 to 10 eyes (4 to 5 rats).

As a result of the conjunctivitis model evaluation test, the present compounds showed an excellent edema formation inhibitory effect.

TABLE VI

[Table 57]

| Test compound | Edema formation inhibitory ratio (%) |
|---|---|
| Compound 1-1 (0.001%) | 26 |
| Compound 1-1 (0.003%) | 30 |
| Compound 1-1 (0.01%) | 37 |
| Control compound B (1%) | 14 |
| Control compound C (1%) | 14 |
| Commercially available drug A (0.5%) | 33 |
| Commercially available drug B (0.1%) | 37 |

From the above results, the present compounds are confirmed to be useful as a treatment agent for anterior eye inflammatory diseases, in particular, as a prophylactic or therapeutic agent for ocular inflammatory diseases such as keratitis, keratoconjunctivitis, conjunctivitis, inflammation by blepharitis, or the like.

7. Anterior Eye Inflammation Model Evaluation Test

In order to evaluate an anti-inflammatory action of the present compound on anterior eye inflammation, an inhibitory effect on a number of infiltrated cells into aqueous humor in a paracentesis induced intraocular inflammation model of rabbits was investigated. Incidentally, this effect was evaluated by calculating an inhibitory ratio from a number of infiltrated cells into aqueous humor in the base agent administered group (control group) and a number of infiltrated cells into aqueous humor in the test compound administered group.
(Preparation of Eye Drop Solution of Test Compound)

A base agent containing a general additive(s) was added to the test compound to prepare a test compound suspension with 3% (W/V).

(Preparation of Paracentesis Induced Intraocular Inflammation Model and Evaluation Method)

1) Male JW rabbits underwent local anesthesia with 0.4% oxybuprocaine hydrochloride (trade name: Benoxil ophthalmic solution 0.4%), and about 0.1 mL of anterior aqueous humor was collected by using a syringe for tuberculin so as not to touch the iris to carry out primary puncture, whereby an inflammatory response was induced.

2) Thirty minutes before the primary puncture, heparin was intravenously administered so as to be about 50 unit/kg.

3) The test compound suspension was eye dropped (instillation dose: 50 μL/time) to both eyes in total four times, 210 minutes before, 60 minutes before, 15 minutes after, and 90 minutes after the primary puncture. To the base agent administered group (control group), the base agent was similarly eye dropped.

4) 120 minutes after the primary puncture, about 1.5 mL/kg of pentobarbital sodium (trade name: Somnopentyl) was intravenously administered from the rabbit ear vein. Thereafter, about 0.1 mL of anterior aqueous humor was collected by using a syringe for tuberculin, and the sample was stored in ice.

5) The number of infiltrated cells into the aqueous humor was measured using a TC10 full-automatic cell counter (Bio-Rad).

Inhibitory ratio (%) of infiltrated cells into aqueous humor in the test compound administered group=100×{1−(average value of the number of infiltrated cells into aqueous humor in the test compound eye drop group)/(average value of the number of infiltrated cells into aqueous humor in the base agent administered group (control group))}(%)　　　(Calculation Formula)

(Test Result and Discussion)

The inhibitory ratio (%) of the number of infiltrated cells into aqueous humor in the case where the compound 11-1 was used as the test compound showed 37%. Incidentally, the average value of the score is each 7 eyes (14 rabbits).

As a result of the anterior eye inflammation model evaluation test, the present compounds showed an excellent inhibitory effect on the number of infiltrated cells into aqueous humor.

From the above results, the present compounds are confirmed to be useful as a treatment agent for anterior eye inflammatory diseases, in particular, as a prophylactic or therapeutic agent for ocular inflammatory diseases such as uveitis, inflammation after surgery and inflammation due to rejection of ocular tissue transplantation, or the like.

8. Dry Eye Syndrome (Dry Eye) Model Evaluation Test

In order to evaluate the treatment effect of the present compounds on corneal disorder accompanied by dry eye syndrome (dry eye), a treatment effect on corneal disorder in an exorbital lacrimal gland-removed rat dry eye model was investigated. This model was prepared in accordance with the method of Fujihara, et al. (Invest. Ophthalmol. Vis. Sci., 42(1): 96-100 (2001)). Incidentally, this effect was scored according to the method of Murakami et al. (New Ophthalmologist 21(1): 87-90 (2004)), the extent of corneal disorder was scored and the improvement ratio was calculated from the corneal disorder score of the base agent administered group (control group), the corneal disorder score of the test compound administered group and the corneal disorder score of the normal rat.

(Preparation of Eye Drop Solution of Test Compound)

A base agent containing a general additive(s) was added to the test compound to prepare test compound suspensions with 0.03% (W/V) and 0.1% (W/V). In addition, a base agent was added to the commercially available drug A to prepare a diluted solution with 0.05% (V/V).

(Preparation of Exorbital Lacrimal Gland-Removed Dry Eye Model and Evaluation Method)

1) By using male SD rats, somnopentyl was administered to the rats to apply them general anesthesia, exorbital lacrimal glands were removed, and corneal disorder was induced over 8 weeks thereafter.

2) The test compound suspension was eye-dropped (instillation dose: 5 μL/time) to both eyes four times a day for 14 days. Incidentally, the base agent was similarly eye-dropped to the administered group (control group), and the commercially available drug A and its diluted solution were similarly eye-dropped.

3) Fourteen days after the start of eye dropping, the cornea was stained with fluorescein. For each of the upper part, the middle part and the lower part of the cornea, scores of the degree of staining with fluorescein were determined according to the following criteria, and an average value of the total of the scores was calculated. Incidentally, 0.5 was set as an intermediate value between each score of 0, 1, 2 and 3.

<<Judgement Standard>>

0: not dyed

1: Dyeing is sparse, and the dyed portions of each dot are separated

2: Dyeing is a middle degree and part of the dotted dyed portions is adjacent

3: Dyeing is dense, and the dyed portions of each point are almost adjacent

Corneal disorder improvement ratio (%) of the test compound administered group=$(Ao-Ax)/(Ao-An)\times 100$    (Calculation Formula)

Ao: Average value of corneal disorder score of the base agent administered group (control group)

Ax: Average value of corneal disorder score of the test compound administered group An: Average value of corneal disorder score of normal rat (Test Result and Consideration)

The corneal disorder improvement ratios (%) when the compound 1-1, the compound 2-1, the compound 11-1, the compound 12-1, the compound 13-1, the commercially available drug A (active ingredient: 0.5% loteprednol etabonate) which is existing ophthalmic solution and a diluted solution of the commercially available drug A were used as the test compounds are shown in Table VII. Incidentally, the average value of the score is each 8 eyes (4 rats).

As a result of the dry eye syndrome (dry eye) model evaluation test, the present compounds showed an excellent corneal disorder improvement ratio.

TABLE VII

[Table 58]

| Test compound | Corneal disorder improvement ratio (%) After 7 days eye dropping | Corneal disorder improvement ratio (%) After 14 days eye dropping |
|---|---|---|
| Compound 1-1 (0.03%) | 22 | 41 |
| Compound 1-1 (0.1%) | 36 | 61 |
| Compound 2-1 (0.1%) | 40 | 45 |
| Compound 11-1 (0.03%) | 35 | 33 |
| Compound 11-1 (0.1%) | 44 | 64 |
| Compound 12-1 (0.03%) | 33 | 48 |
| Compound 12-1 (0.1%) | 42 | 58 |
| Compound 13-1 (0.1%) | 38 | 46 |
| Commercially available drug A diluted solution (0.05%) | 21 | 38 |
| Commercially available drug A (0.5%) | 54 | 54 |

From the above results, the present compounds are confirmed to be useful as a treatment agent for anterior eye inflammatory diseases, in particular, as a prophylactic or therapeutic agent for ocular inflammatory diseases such as keratitis, keratoconjunctivitis, conjunctivitis, blepharitis, dry eye syndrome (dry eye), or the like.

9. Allergic Conjunctivitis Model Evaluation Test

In order to evaluate an anti-allergic action of the present compounds on allergic conjunctivitis, an inhibitory effect on hyperemia in an ovalbumin actively sensitized allergic conjunctivitis model of rabbits was investigated. Incidentally, this effect was evaluated by calculating an inhibitory ratio from the score of the base agent administered group (control group) and the score of the test compound administered group.

(Preparation of Eye Drop Solution of Test Compound)

A base agent containing a general additive(s) was added to the test compound to prepare test compound suspensions with 1% (W/V) and 3% (W/V).

(Preparation of Ovalbumin Actively Sensitized Allergic Conjunctivitis Model and Evaluation Method)

By using male JW rabbits, ovalbumin (200 μg/mL/physiological saline solution) adsorbed on aluminum hydroxide gel was injected 200 μL per eye into bulbar conjunctiva of both eyes of rabbits, respectively, to perform active sensitization.

After 14 days from sensitization or later, the test compound suspension was eye-dropped four times a day for 4 days, and then, at the next day, it was eye-dropped (instillation dose: 50 μL/time) once to both eyes. Incidentally, the base agent was similarly eye-dropped to the base agent administered group (control group).

One hour after the final eye dropping of the test compound suspension, a physiological saline solution containing 0.02% (W/V) of ovalbumin was administered from rabbit ear vein at a dose of 1.5 mL per 1 kg of rabbit to induce allergic conjunctivitis.

After 0.5 hour of the challenge, the degree of hyperemia symptoms of both ocular conjunctiva of rabbits was evaluated according to the following criteria, and the average value of the total of these scores was calculated.

<<Judgement Standard>>

0: No findings

1: A state in which several expanded blood vessels are observed in part of the superior rectus muscle of the eyeball or the corneal limbus 2: A state in which many expanded blood vessels are observed in the superior rectus muscle of the eyeball, or a state in which several expanded blood vessels are observed in the superior rectus muscle of the eyeball and expansions of several blood vessels are observed in part of the corneal limbus 3: A state in which a large number of expanded blood vessels are observed the superior rectus muscle of the eyeball and in part of the corneal limbus 4: A state in which a large number of expanded blood vessels are observed the superior rectus muscle of the eyeball and all around the corneal limbus 5: A state in which expanded blood vessels are observed on the superior rectus muscle of the eyeball, the entire circumference of the corneal limbus, and on the other ocular conjunctiva Inhibitory ratio (%) of hyperemia of the test compound administered group=$\{(Ao-Ap1)-(Ax-Ap2)\}/(Ao-Ap1)\times 100$    (Calculation Formula)

Ao: Average value of hyperemia score of the base agent administered group (control group)
Ax: Average value of hyperemia score of the test compound administered group
Ap1: Average value of hyperemia score before challenge of the base agent administered group
Ap2: Average value of hyperemia score before challenge of the test compound administered group (Test Result and Consideration)

The hyperemia inhibitory ratios (%) when the compound 1-1, the compound 2-1, the compound 5-2, the compound 11-1 and the compound 14-1 were used as the test compounds are shown in Table VIII. Incidentally, the average value of the score is each 8 eyes (8 rabbits).

As a result of the allergic conjunctivitis model evaluation test, the present compounds showed an excellent hyperemia inhibitory effect.

TABLE VIII

[Table 59]

| Test compound | Eye congestion inhibitory ratio (%) |
|---|---|
| Compound 1-1 (1%) | 35 |
| Compound 2-1 (1%) | 29 |
| Compound 5-2 (3%) | 35 |
| Compound 11-1 (1%) | 44 |
| Compound 14-1 (1%) | 22 |

From the above results, the present compounds are confirmed to be useful as a treatment agent for anterior eye inflammatory diseases, in particular, as a prophylactic or therapeutic agent for ocular inflammatory diseases such as keratitis, keratoconjunctivitis, conjunctivitis, blepharitis, dry eye syndrome (dry eye), allergic conjunctivitis, or the like.

10. Retinal Vascular Permeability Model Evaluation Test

In order to evaluate the inhibitory effect of the present compounds on VEGF-induced retinal vascular permeability, the inhibitory effect of the present compound on retinal vascular permeability in a VEGF-induced retinal elevated vascular permeability model of rabbits was evaluated. Incidentally, this effect was evaluated by calculating a leaked amount of the fluorescent dye of the base agent administered group (non-induced group), a leaked amount of the fluorescent dye of the base agent administered group (control group) and a leaked amount of the fluorescent dye of the test compound administered group.

(Preparation of Test Compound Suspension or Test Compound Solution)

To the test compound was added 0.01% Polysorbate 80/0.5% sodium carboxymethyl cellulose/PBS (hereinafter referred to as "base agent A".), whereby 2% (W/V) or 8% (W/V) of the test compound suspension was prepared. Or else, to the test compound was added PEG400 (hereinafter referred to as "base agent B".), whereby 6% (W/W) of the test compound solution was prepared.

(Preparation of Reagent)

VEGF solution: humanVEGF165 was dissolved in PBS to prepare 50 µg/mL of VEGF solution.

(Preparation of VEGF-Induced Retinal Vascular Permeability Model and Evaluation Method)

1) A mixed solution (1 mL/kg) of 5% ketamine hydrochloride injection solution and 2% xylazine hydrochloride injection solution with the ratio of 7:1 was intramuscularly administered to rabbits (Dutch male rabbits), and the rabbits were anesthetized.

2) Tropicamide-phenylephrine hydrochloride ophthalmic solution (trade name: Midlin P) was eye dropped to maintain pupillary mydriasis, and then, the VEGF solution was intravitreally administered. Incidentally, PBS was intravitreally administered to the base agent administration group (non-induced group).

3) Fluorescein was intravenously administered 2 days after intravitreal administration of VEGF. Two hours after the intravenous administration of fluorescein, an amount of the leaked fluorescent dye in the vitreous body was measured by using a fluorophotometer.

(Test Method)

1) One week before or 4 weeks before VEGF-induction, 50 µL of the test compound suspension (prepared by the base agent A) was intravitreally administered once, or 5 µL of the test compound solution (prepared by the base agent B) was intravitreally administered once. Incidentally, in the base agent administered group (non-induced group) and the base agent administered group (control group), the base agent A was used in place of the test compound suspension, or the base agent B was used in place of the test compound solution.

2) Inhibition ratio of elevated retinal vascular permeability was calculated according to the following calculation formula.

Inhibitory ratio (%) on elevated retinal vascular permeability of the test compound administered group=100×{1−(average value of a leaked fluorescent dye amount in the test compound administered group−average value of a leaked fluorescent dye amount in the base agent administered group (non-induced group))/(average value of a leaked fluorescent dye amount in the base agent administered group (control group)−average value of a leaked fluorescent dye amount of the base agent administered group (non-induced group))}   (Calculation Formula)

(Test Result and Consideration)

The inhibitory ratios (%) on elevated retinal vascular permeability when the compound 1-1, the compound 2-1, the compound 5-2, the compound 11-2, the compound 14-3, the control compound B, the control compound D and the control compound E were used as the test compounds are shown in Table IX. Incidentally, the average value of the leaked fluorescent dye amount is each 4 to 6 eyes (2 to 3 rabbits).

As a result of the retinal vascular permeability model evaluation test, the present compounds showed an excellent inhibitory effect on elevated retinal vascular permeability.

TABLE IX

[Table 60]

| Test compound | Administration dose/base agent | Term from administration of test compound to induction | Inhibitory ratio (%) on elevated vascular permeability |
|---|---|---|---|
| Compound 1-1 | 6% 5 µL/B | 4 weeks | 80 |
| Compound 2-1 | 2% 50 µL/A | 1 week | >99 |
| Compound 2-1 | 2% 50 µL/A | 4 weeks | 91 |
| Compound 5-2 | 2% 50 µL/A | 1 week | 96 |
| Compound 5-2 | 2% 50 µL/A | 4 weeks | 91 |
| Compound 11-2 | 2% 50 µL/A | 4 weeks | 92 |
| Compound 14-3 | 8% 50 µL/A | 4 weeks | 89 |
| Control compound B | 2% 50 µL/A | 1 week | 36 |
| Control compound D | 2% 50 µL/A | 4 weeks | 38 |
| Control compound E | 2% 50 µL/A | 1 week | 47 |

From the above results, the present compounds are confirmed to be useful as a treatment agent for posterior eye inflammatory disease, in particular, as a prophylactic or therapeutic agent for age-related macular degeneration, diabetic macular edema, central retinal vein occlusion, branch retinal vein occlusion, or the like.

PREPARATION EXAMPLES

A general Preparation example of the present compound is shown below.

Preparation Example 1: Tablet

In 150 mg

| | |
|---|---|
| Present compound | 1 mg |
| Lactose | 100 mg |
| Corn starch | 40 mg |
| Calcium carboxymethyl cellulose | 4.5 mg |
| Hydroxypropyl cellulose | 4 mg |
| Magnesium stearate | 0.5 mg |

The tablet of the above-mentioned prescription was subjected to coating by using 3 mg of a coating agent (for example, a coating agent generally used such as hydroxypropylmethyl cellulose, macrogol, a silicone resin, or the like) to obtain the intended tablet. In addition, a desired tablet may also be obtained by optionally changing the present compound, the kind of the additives and/or the amount of the additives.

Preparation Example 2: Capsule

In 150 mg

| | |
|---|---|
| Present compound | 5 mg |
| Lactose | 135 mg |
| Calcium carboxymethyl cellulose | 4.5 mg |
| Hydroxypropyl cellulose | 4 mg |
| Magnesium stearate | 1.5 mg |

A desired capsule may also be obtained by optionally changing the present compound, the kind of the additives and/or the amount of the additives.

Preparation Example 3: Ophthalmic Agent

In 100 mL

| | |
|---|---|
| Present compound | 100 mg |
| Sodium chloride | 900 mg |
| Polysorbate 80 | 500 mg |
| Sodium hydroxide | q.s. |
| Hydrochloric acid | q.s. |
| Sterile purified water | q.s. |

Preparation Example 4: Intravitreal Administration Agent

In 100 mL

| | |
|---|---|
| Present compound | 100 mg |
| Polyethylene glycol 400 | q.s. |

A desired ophthalmic agent may also be obtained by optionally changing the present compound, the kind of the additives and/or the amount of the additives.

INDUSTRIAL APPLICABILITY

The novel [4-(1,3,3-trimethyl-2-oxo-3,4-dihydro-1H-quinoxalin-7-yl)-phenoxy]ethyloxy compound or a salt thereof according to the present invention has the glucocorticoid receptor agonist activity, and useful as a prophylactic or therapeutic agent of a disease, in particular, glucocorticoid receptor related disease, as a medicine.

The invention claimed is:

1. A compound of
   (S)-8-(5-fluoro-2-methylphenoxymethyl)-7-[4-(2-hydroxypropyl)oxy-2-methoxy-phenyl]-1,3,3-trimethyl-3,4-dihydro-1H-quinoxalin-2-one,
   or a pharmaceutically acceptable salt or a hydrate or a solvate thereof.

2. A compound of
   (R)-8-(5-fluoro-2-methylphenoxymethyl)-7-[4-(2-hydroxypropyl)oxy-2-methoxy-phenyl]-1,3,3-trimethyl-3,4-dihydro-1H-quinoxalin-2-one,
   or a pharmaceutically acceptable salt or a hydrate or a solvate thereof.

3. A compound of
   (R)-8-(5-fluoro-2-methylphenoxymethyl)-7-[4-(2-hydroxybutyl)oxy-2-methoxy-phenyl]-1,3,3-trimethyl-3,4-dihydro-1H-quinoxalin-2-one,
   or a pharmaceutically acceptable salt or a hydrate or a solvate thereof.

4. A compound of
   (S)-8-(5-fluoro-2-methylphenoxymethyl)-7-[4-(2-hydroxybutyl)oxy-2-methoxy-phenyl]-1,3,3-trimethyl-3,4-dihydro-1H-quinoxalin-2-one,
   or a pharmaceutically acceptable salt or a hydrate or a solvate thereof.

5. A compound of
   (S)-7-[4-(2,4-dihydroxybutyl)oxy-2-methoxyphenyl]-8-(5-fluoro-2-methylphenoxy-methyl)-1,3,3-trimethyl-3,4-dihydro-1H-quinoxalin-2-one,
   or a pharmaceutically acceptable salt or a hydrate or a solvate thereof.

6. A compound of
   (R)-7-[4-(2,4-dihydroxybutyl)oxy-2-methoxyphenyl]-8-(5-fluoro-2-methylphenoxy-methyl)-1,3,3-trimethyl-3,4-dihydro-1H-quinoxalin-2-one,
   or a pharmaceutically acceptable salt or a hydrate or a solvate thereof.

7. A compound of
   8-(5-fluoro-2-methylphenoxymethyl)-7-[4-(2-hydroxyethyl)oxy-2-methoxyphenyl]-1,3,3-trimethyl-3,4-dihydro-1H-quinoxalin-2-one,
   or a pharmaceutically acceptable salt or a hydrate or a solvate thereof.

8. A compound of
   (S)-7-[4-(2,3-dihydroxypropyl)oxy-2-methoxyphenyl]-8-(5-fluoro-2-methyl-phenoxymethyl)-1,3,3-trimethyl-3,4-dihydro-1H-quinoxalin-2-one,
   or a pharmaceutically acceptable salt or a hydrate or a solvate thereof.

9. A compound of
   (R)-7-[4-(2,3-dihydroxypropyl)oxy-2-methoxyphenyl]-8-(5-fluoro-2-methyl-phenoxymethyl)-1,3,3-trimethyl-3,4-dihydro-1H-quinoxalin-2-one,
   or a pharmaceutically acceptable salt or a hydrate or a solvate thereof.

* * * * *